US008560350B2

(12) United States Patent
Nadai

(10) Patent No.: US 8,560,350 B2
(45) Date of Patent: Oct. 15, 2013

(54) METHOD, SYSTEM AND COMPUTER PROGRAM PRODUCT FOR GENERATING AN ELECTRONIC BILL HAVING OPTIMIZED INSURANCE CLAIM ITEMS

(76) Inventor: Robert J. Nadai, Royal Oak, MI (US)

( * ) Notice: Subject to any disclaimer, the term of this patent is extended or adjusted under 35 U.S.C. 154(b) by 1492 days.

(21) Appl. No.: 11/285,579

(22) Filed: Nov. 22, 2005

(65) Prior Publication Data
US 2007/0118410 A1 May 24, 2007

(51) Int. Cl.
G06Q 40/00 (2012.01)
(52) U.S. Cl.
USPC .................. 705/4; 705/2; 705/3; 705/40
(58) Field of Classification Search
None
See application file for complete search history.

(56) References Cited

U.S. PATENT DOCUMENTS

| | | | |
|---|---|---|---|
| 5,842,175 A * | 11/1998 | Andros et al. ................ 705/3 |
| 5,876,611 A * | 3/1999 | Shettigar .................. 210/739 |
| 6,154,726 A | 11/2000 | Rensimer et al. |
| 6,223,164 B1 | 4/2001 | Seare et al. |
| 6,316,455 B1 * | 11/2001 | Griffin et al. ............ 514/266.3 |
| 6,347,329 B1 | 2/2002 | Evans |
| 6,381,576 B1 | 4/2002 | Gilbert |
| 6,595,362 B2 * | 7/2003 | Penney et al. ................ 206/364 |
| 6,655,583 B2 | 12/2003 | Walsh et al. |
| 2002/0022972 A1 | 2/2002 | Costello |
| 2002/0035484 A1 * | 3/2002 | McCormick .................. 705/2 |
| 2002/0077854 A1 | 6/2002 | Porterfield |
| 2002/0087358 A1 | 7/2002 | Gilbert |
| 2002/0091540 A1 | 7/2002 | Stumne et al. |
| 2002/0116219 A1 | 8/2002 | Ibok et al. |
| 2002/0120466 A1 | 8/2002 | Finn |
| 2002/0123907 A1 | 9/2002 | Strayer |
| 2002/0133460 A1 * | 9/2002 | Field ............................ 705/40 |
| 2003/0055687 A1 * | 3/2003 | Rudy ............................ 705/4 |
| 2003/0073971 A1 * | 4/2003 | Saker ........................ 604/403 |
| 2003/0074228 A1 | 4/2003 | Walsh |
| 2003/0083903 A1 | 5/2003 | Myers |
| 2003/0191669 A1 * | 10/2003 | Fitzgerald et al. ............. 705/2 |
| 2004/0128163 A1 | 7/2004 | Goodman |
| 2004/0153341 A1 * | 8/2004 | Brandt et al. .................. 705/2 |
| 2004/0199404 A1 | 10/2004 | Ripperger et al. |
| 2004/0204961 A1 | 10/2004 | Rensimer et al. |
| 2005/0205093 A1 * | 9/2005 | Jabour ..................... 128/204.23 |
| 2005/0240473 A1 * | 10/2005 | Ayers et al. ................... 705/14 |
| 2005/0286686 A1 * | 12/2005 | Krstulich .................. 379/32.01 |

(Continued)

OTHER PUBLICATIONS

Joel W. Hay and Michael J. Leahy; Competition Among Health Plans: Some Preliminary Evidence; Southern Economic Journal; vol. 50, No. 3, p. 831 (Jan. 1984).*

(Continued)

Primary Examiner — Virpi Kanervo
(74) Attorney, Agent, or Firm — Brooks Kushman P.C.

(57) ABSTRACT

A method, system and computer program product for generating an electronic bill having optimized insurance claim items based on an insurance carrier of a patient are provided. The method includes receiving insurance carrier data which identifies a patient's insurance carrier and patient data which identifies a patient. The method also includes receiving treatment data which identifies a drug administered to the patient and a procedure performed on the patient on a date of service. The treatment data is processed to obtain nurse documentation, such as treatment and/or flow sheets. An electronic bill is automatically generated having optimized reimbursable insurance claim items including predetermined codes based on the treatment data and the insurance carrier data to facilitate approval of the bill by the insurance carrier.

44 Claims, 79 Drawing Sheets

(56) References Cited

U.S. PATENT DOCUMENTS

| | | | |
|---|---|---|---|
| 2006/0031099 A1* | 2/2006 | Vitello et al. | 705/2 |
| 2006/0036472 A1* | 2/2006 | Crockett | 705/3 |
| 2006/0190350 A1* | 8/2006 | Maas | 705/26 |
| 2006/0212315 A1* | 9/2006 | Wiggins | 705/2 |
| 2006/0247947 A1* | 11/2006 | Suringa | 705/2 |
| 2007/0005402 A1* | 1/2007 | Kennedy et al. | 705/4 |

OTHER PUBLICATIONS

Maura Reynolds; Drug Panel Praises Treatment Programs; Los Angeles Times; p. 42, (Sep. 20, 1990).*

Frank E. James; Patient's Race May Affect Health Care, Study Suggests; Wall Street Journal; p. 1 (Jan. 13, 1989).*

* cited by examiner

Dr Maya Sandbox
SOS-Software Practice

Treatment Sheet for Mary Medicare    DOB: 10/17/1924   DOS: 9/21/2005

*Insurer:* Medicare                                  *Diagnosis:* CHRONIC LEUKEMA

| Cycle: 4 | Temp: 97.2 | Height: 5'2" | Fluids Inf time: | 0:00 |
| Day: D1 | Pulse: 65 | Weight: 192 lbs | Chemo Inf time: | 2:35 |
| | BP: 153/65 | BSA: 1.88 | Non-chemo Inf time: | 0:30 |

*Karnofsky Value:* 60 Requires occasional assistance, but able to care for most personal needs    *ECOG Value:* 2 Ambulatory and capable of all selfcare but unable to carry out any work activities LABS OK FOR CHEMO. IV STARTED IN LFA WITH A 22G JELCO. SITE CLEAR WITH GOOD FLASHBACK. POST LAB DRAW CHEMO GIVEN WITHOUT INCIDENT. IV SITE REMAINS CLEAR THROUGHOUT INFUSION WITH FREQUENT CHECKS. NEEDLE REMOVED AND BANDAID APPLIED. ENCOURAGED TO CALL THE OFFICE WITH ANY CONCERNS. DISCHARGED STABLE.

| Proc | Proc Name | Admin Type | Dosage | Waste | Inf Time | Inf Start | Inf Stop |
|---|---|---|---|---|---|---|---|
| J9310 | Rituxan 100 mg | Infusion | 675 | 25 | 1:35 | | |
| J9185 | Fludarbine 50 mg | Infusion | 45 | 5 | 1:00 | | |
| J1200 | Diphehydramine 50 mg | Infusion | 25 | 25 | 0:30 | | |
| J7040 | 0.9 Normal Saline 500 ml | Dilution | 500 | | | | |
| J7050 | 0.9 Normal Saline 250 ml | Dilution | 250 | | | | |
| J7040 | 0.9 Normal Saline 500 ml | Dilution | 500 | | | | |
| J1642 | Heplock Flush 10 units | | 10 | | | | |
| J7051 | Saline Sterile 5 cc | | | | | | |
| 85025 | Complete blood count | | | | | | |

FIGURE 21

G-Wizz-Patent Pending-[rptFlow]

File Window Help

Day: D1  Pulse: 65  Weight: 192 lbs  Chemo Inf time: 2:35
  BP: 153/65  BSA: 1.88  Non-chemo Inf time: 0:30

Karnofsky Value: 60 Requires occasional assistance, but able to care for most personal needs
ECOG Value: 2 Ambulatory and capable of all selfcare but unable to carry out any work activities LABS OK FOR CHEMO. IV STARTED IN LFA WITH A 22G JELCO. SITE CLEAR WITH GOOD FLASHBACK. POST LAB DRAW CHEMO GIVEN WITHOUT INCIDENT. IV SITE REMAINS CLEAR THROUGHOUT INFUSION WITH FREQUENT CHECKS. NEEDLE REMOVED AND BANDAID APPLIED. ENCOURAGED TO CALL THE OFFICE WITH ANY CONCERNS. DISCHARGED STABLE.

| Proc | Proc Name | Admin Type | Dosage | Waste | Inf Time | Inf Start | Inf Stop |
|---|---|---|---|---|---|---|---|
| J9310 | Rituxan 100 mg | Infusion | 675 | 25 | 1:35 | | |
| J9185 | Fludarbine 50 mg | Infusion | 45 | 5 | 1:00 | | |
| J1200 | Diphehydramine 50 mg | Infusion | 25 | 25 | 0:30 | | |
| J7040 | 0.9 Normal Saline 500 ml | Dilution | 500 | | | | |
| J7050 | 0.9 Normal Saline 250 ml | Dilution | 250 | | | | |
| J7040 | 0.9 Normal Saline 500 ml | Dilution | 500 | | | | |
| J1642 | Heplock Flush 10 units | | 500 | | | | |
| J7051 | Saline Sterile 5 cc | | 10 | | | | |
| 85025 | Complete blood count | | | | | | |
| G9031 | Quite a bit - Survey/Fatigue | | | | | | |
| G9026 | A little bit - Survey/Pain | | | | | | |
| G9021 | Not at all - Survey/Nausea | | | | | | |

Doctor: _____  Nurse: _____

G-Wiz - Patent Pending - [rptClaimsByDate]

File Window Help

Medicare, Mary
Insurance: Medicare

Dr Maya Sandbox

Claim # 1

| Date | Proc | | DX1 | DX2 | Mod | HCT | Qty | Charges |
|---|---|---|---|---|---|---|---|---|
| 9/21/2005 | G0359 | Chemo IV infusion, single/initial drug, 1st hour | 20810 | | | | 1 | $250.00 |
| 9/21/2005 | G0360 | Each additional hour of chemo infusion, up to 8 hours | 20810 | | | | 1 | $75.00 |
| 9/21/2005 | J9310 | Rituxan | 20810 | | | | 7 | $4,200.00 |
| 9/21/2005 | G9021 | Not at all - Survey/Nausea | 20810 | | | | 1 | $44.00 |
| 9/21/2005 | G9026 | A little bit - Survey/Pain | 20810 | | | | 1 | $44.00 |
| 9/21/2005 | G9031 | Quite a bit - Survey/Fatigue | 20810 | | | | 1 | $44.00 |

Claim charges: $4,657.00

Claim # 2

| Date | Proc | | DX1 | DX2 | Mod | HCT | Qty | Charges |
|---|---|---|---|---|---|---|---|---|
| 9/21/2005 | G0362 | Admin of each additional seq infused drug | 20810 | | | | 1 | $100.00 |
| 9/21/2005 | J9185 | Fludarbine | 20810 | | | | 1 | $400.00 |
| 9/21/2005 | G0349 | Admin of each additional seq infused drug, non-chemo | 20810 | | | | 1 | $55.00 |
| 9/21/2005 | J1200 | Diphehydramine | 20810 | 78701 | | | 1 | $5.00 |
| 9/21/2005 | J7040 | 0.9 Normal Saline | 20810 | | | | 2 | $30.00 |
| 9/21/2005 | J7050 | 0.9 Normal Saline | 20810 | | | | 1 | $7.00 |

Claim charges: $597.00

Claim # 3

FIGURE 27

Claim # 2

| Date | Proc | | DX1 | DX2 | Mod | HCT | Qty | Charges |
|---|---|---|---|---|---|---|---|---|
| 9/21/2005 | G0362 | Admin of each additional seq infused drug | 20810 | | | | 1 | $100.00 |
| 9/21/2005 | J9185 | Fludarbine | 20810 | | | | 1 | $400.00 |
| 9/21/2005 | G0349 | Admin of each additional seq infused drug, non-chemo | 20810 | | | | 1 | $55.00 |
| 9/21/2005 | J1200 | Diphehydramine | 20810 | 78701 | | | 1 | $5.00 |
| 9/21/2005 | J7040 | 0.9 Normal Saline | 20810 | | | | 2 | $30.00 |
| 9/21/2005 | J7050 | 0.9 Normal Saline | 20810 | | | | 1 | $7.00 |

*Claim charges:* $597.00

Claim # 3

| Date | Proc | | DX1 | DX2 | Mod | HCT | Qty | Charges |
|---|---|---|---|---|---|---|---|---|
| 9/21/2005 | 85025 | Complete blood count | 20810 | | | | 1 | $17.00 |

*Claim charges:* $17.00

*Bill Release Date:* 09/22/2005 22:40    *Original Release Date:*

*Bill charges:* $5,271.00

*Grand Total:* $5,271.00

FIGURE 28

Patient Bills for Mary Medicare   DOB: 10/17/1924

** To select an option for a bill, you must first position the cursor at that bill (date will be highlighted)
To edit or delete, Bill must be in 'Open' status.

| Bill DOS | Cycle | Day/Wk | Status | Original Release Date | Options | | | | | |
|---|---|---|---|---|---|---|---|---|---|---|
| 9/21/2005 | 4 | D1 | Billed 9/22/2005 10:40:08 PM | | Bill Treatment Sheet | Edit Edit | Print/View Print/View | Label | Copy Copy | Delete | Change Status |
| 9/19/2005 | | | Billed 9/19/2005 11:04:11 PM | | Bill Treatment Sheet | Edit Edit | Print/View Print/View | Label | Copy Copy | Delete | Change Status |

G-Wiz - Patent Pending - [rptClaimsByDate]

File  Window  Help

Close
Page Setup...
Print...  Ctrl+P
Exit

DXcodes | ProcsAndCodes | DoctorsAndFees | BillingReports | SurveyOnOff

Dr Maya Sandbox

*Claim #*   1

| Date | Proc | | DX1 | DX2 | Mod | HCT | Qty | Charges |
|---|---|---|---|---|---|---|---|---|
| 9/19/2005 | 36000 | Introduction of needle or intracatheter, vein | 2384 | | 59 | | 1 | $40.00 |
| 9/19/2005 | G0345 | Initial hour of hydration | 2384 | | | | 1 | $75.00 |
| 9/19/2005 | G0346 | Each additional hour of hydration, up to 8 | 2384 | | | | 1 | $30.00 |
| 9/19/2005 | J7040 | 0.9 Normal Saline (500 ml) | 2384 | 2765 | | | 1 | $15.00 |
| 9/19/2005 | 99195 | Phlebotomy | 2384 | | | | 1 | $80.00 |
| 9/19/2005 | 36415 | Venipuncture | 2384 | | | | 1 | $10.00 |

*Claim charges:*   $250.00

*Bill charges:*   $250.00

*Grand Total:*   $250.00

*Bill Release Date:*          *Original Release Date:*

G-Wiz - Patent Pending - [rptClaimsByDate]

Close
DXcodes | ProcsAndCodes | DoctorsAndFees | BillingReports | SurveyOnOff
File Window Help Cimetidine, Hydra
Insurance: PPOM Dr Maya Sandbox Claim # 1

| Date | Proc | | DX1 | DX2 | Mod | HCT | Qty | Charges |
|---|---|---|---|---|---|---|---|---|
| 7/5/2005 | G0347 | Initial hour IV infusion, non-chemo | 1622 | | | | 1 | $150.00 |
| 7/5/2005 | J2405 | Zofran | 1622 | 78701 | | | 32 | $320.00 |
| 7/5/2005 | G0349 | Admin of each additional seq infused drug, non-chemo | 1622 | | | | 1 | $55.00 |
| 7/5/2005 | J3490 | Cimetidine | 1622 | 78701 | | | 1 | $10.00 |

*** J3490 Cimetidine IV 300 mg

| 7/5/2005 | G0346 | Each additional hour of hydration, up to 8 | 1622 | | 59 | | 2 | $60.00 |
| 7/5/2005 | J7030 | 0.9 Normal Saline | 1622 | | | | 1 | $24.00 |

Claim charges: $619.00

Claim # 2

| Date | Proc | | DX1 | DX2 | Mod | HCT | Qty | Charges |
|---|---|---|---|---|---|---|---|---|
| 7/5/2005 | 85025 | Complete blood count | 1622 | | | | 1 | $17.00 |
| 7/5/2005 | 99070 | Chemo kit | 1622 | | | | 1 | $65.00 |

*** Chemo kit

| 7/5/2005 | 99211 | OV Brief | 1622 | | 25 | | 1 | $38.00 |

Claim charges: $120.00

Bill Release Date: 08/23/2005 16:01    Original Release Date: 07/05/2005 16:16    Bill charges: $739.00

Page: |◄| 1 |►|
Ready

Dr Maya Sandbox

Treatment Sheet for Teresa Taxotere    DOB: 9/18/1918    DOS: 9/21/2005

Insurer: Other    Diagnosis: Lung cancer - upper lobe

| | | | | | |
|---|---|---|---|---|---|
| Cycle: 1 | Temp: 98.7 | Height: "  | Fluids Inf time: | 0:00 | |
| Day: W2 | Pulse: 59 | Weight: lbs | Chemo Inf time: | 1:10 | |
| | BP: 153/58 | BSA: | Non-chemo Inf time: | 0:00 | |

Karnofsky Value: +02 Normal, no complaints; no evidence of disease    ECOG Value: 0 Fully active, able to carry on all pre-disease performance without restriction Medaport accessed with 20 guage, 1 inch huber needle. Excellent blood return. Chemo given with no complications. Huber needle flushed, then removed. No reddness or swelling at medaport site. Spent considerable time educating the patient.

| Proc | Proc Name | Admin Type | Dosage | Waste | Inf Time | Inf Start | Inf Stop |
|---|---|---|---|---|---|---|---|
| J7050 | 0.9 Normal Saline (250 ml) 250 ml | Dilution | 500 | | | | |
| J1626 | Kytril .1 mg | Push | 1 | | | | |
| J9170 | Docetaxel (Taxotere) 20 mg | Infusion | 42 | 18 | | 1:00 | |
| J9390 | Vinorelbine/Navelbine 10 mg | Infusion | 35 | 5 | | 0:10 | |
| J7051 | Saline Sterile (5 cc) 5 cc | | 20 | | | | |
| J1644 | Heparin 1000 units | | 500 | | | | |
| J0880 | Aranesp 5 ug | Injection | 300 | | | | |

FIGURE 62

G-Wiz - Patent Pending - [rptFlow]

Close

DXcodes | ProcsAndCodes | DoctorsAndFees | BillingReports | SurveyOnOff

File Window Help

Day: W2  Pulse: 59  Weight: lbs  Chemo Inf time: 1:10
  BP: 153/58  BSA:  Non-chemo Inf time: 0:00

Karnofsky Value: +02 Normal, no complaints; no evidence of disease   ECOG Value: 0 Fully active, able to carry on all pre-disease performance without restriction Medaport accessed with 20 guage, 1 inch huber needle. Excellent blood return. Chemo given with no complications. Huber needle flushed, then removed. No reddness or swelling at medaport site. Spent considerable time educating the patient.

| Proc | Proc Name | Admin Type | Dosage | Waste | Inf Time | Inf Start | Inf Stop |
|---|---|---|---|---|---|---|---|
| J7050 | 0.9 Normal Saline (250 ml) 250 ml | Dilution | 500 | | | | |
| J1626 | Kytril .1 mg | Push | 1 | | | | |
| J9170 | Docetaxel (Taxotere) 20 mg | Infusion | 42 | 18 | 1:00 | | |
| J9390 | Vinorelbine/Navelbine 10 mg | Infusion | 35 | 5 | 0:10 | | |
| J7051 | Saline Sterile (5 cc) 5 cc | | 20 | | | | |
| J1644 | Heparin 1000 units | | 500 | | | | |
| J0880 | Aranesp 5 ug | Injection | 300 | | | | |
| 85025 | Complete blood count | | | | | | |
| A4221 | Chemo kit ('Other' ins) | | | | | | |
| A4212 | Huber needle | | | | | | |
| S1016 | Heavy duty tubing | | | | | | |
| 99211 | OV Brief | | | | | | |

Doctor: _____  Nurse: _____

Page: |◄| ◄ | 1 | ► | ►|

Ready

FIGURE 63

Figure 64:
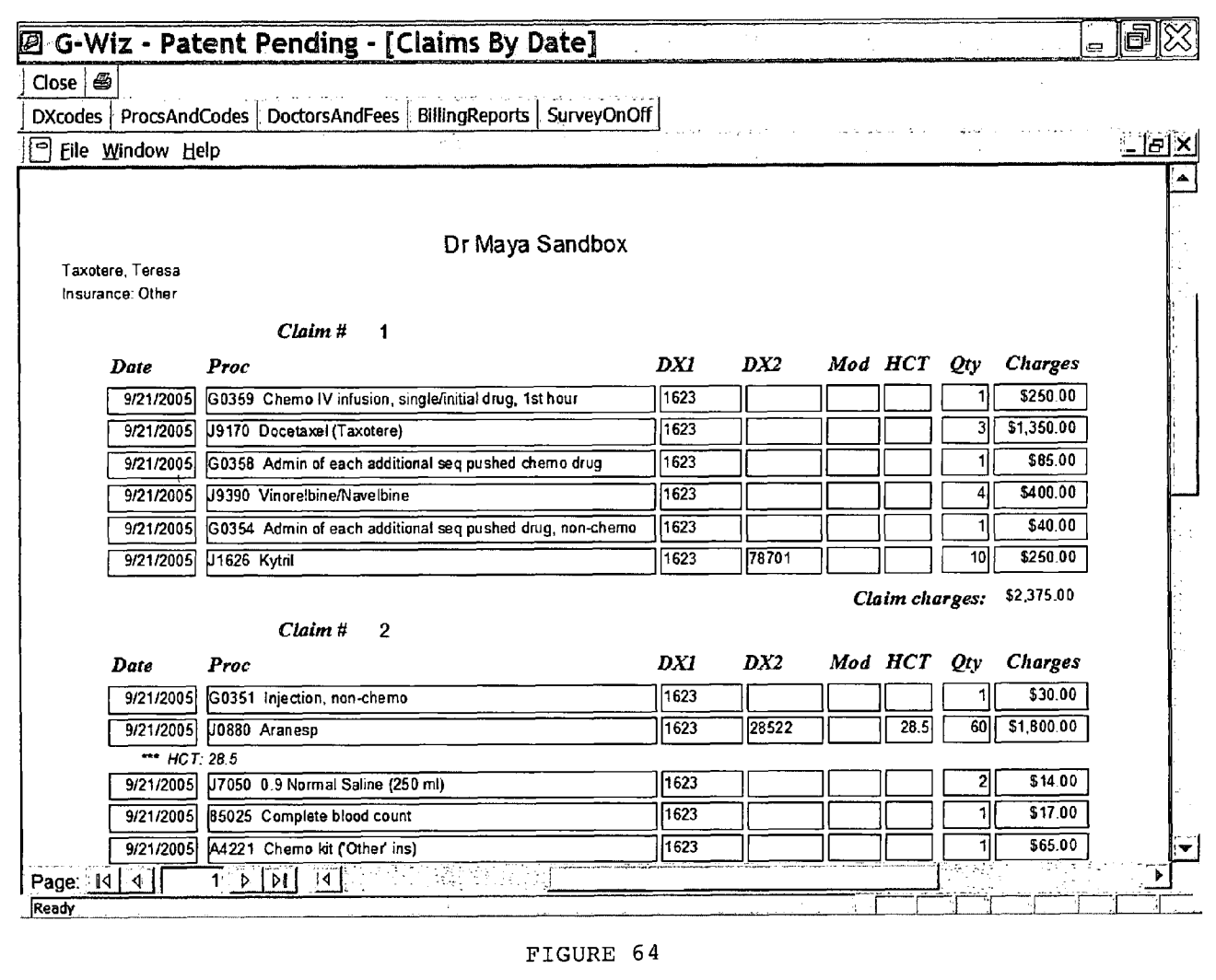

G-Wiz - Patent Pending - [Claims By Date]

Close

DXcodes | ProcsAndCodes | DoctorsAndFees | BillingReports | SurveyOnOff

File  Window  Help

Taxotere, Teresa
Insurance: Other

Dr Maya Sandbox

Claim # 1

| Date | Proc | | DX1 | DX2 | Mod | HCT | Qty | Charges |
|---|---|---|---|---|---|---|---|---|
| 9/21/2005 | G0359 | Chemo IV infusion, single/initial drug, 1st hour | 1623 | | | | 1 | $250.00 |
| 9/21/2005 | J9170 | Docetaxel (Taxotere) | 1623 | | | | 3 | $1,350.00 |
| 9/21/2005 | G0358 | Admin of each additional seq pushed chemo drug | 1623 | | | | 1 | $85.00 |
| 9/21/2005 | J9390 | Vinorelbine/Navelbine | 1623 | | | | 4 | $400.00 |
| 9/21/2005 | G0354 | Admin of each additional seq pushed drug, non-chemo | 1623 | | | | 1 | $40.00 |
| 9/21/2005 | J1626 | Kytril | 1623 | 78701 | | | 10 | $250.00 |

Claim charges: $2,375.00

Claim # 2

| Date | Proc | | DX1 | DX2 | Mod | HCT | Qty | Charges |
|---|---|---|---|---|---|---|---|---|
| 9/21/2005 | G0351 | Injection, non-chemo | 1623 | | | | 1 | $30.00 |
| 9/21/2005 | J0880 | Aranesp | 1623 | 28522 | | 28.5 | 60 | $1,800.00 |
| *** HCT: 28.5 | | | | | | | | |
| 9/21/2005 | J7050 | 0.9 Normal Saline (250 ml) | 1623 | | | | 2 | $14.00 |
| 9/21/2005 | 85025 | Complete blood count | 1623 | | | | 1 | $17.00 |
| 9/21/2005 | A4221 | Chemo kit ('Other' ins) | 1623 | | | | 1 | $65.00 |

Page:  1

Ready

G-Wiz - Patent Pending - [CLICK FOR: Pump, Conrad]

DXcodes | ProcsAndCodes | DoctorsAndFees | BillingReports | SurveyOnOff

File  Edit  Insert  Records  Window  Help

Close

Name: Conrad Pump    DOB: 7/15/1948    Age:: 57    *Dr Maya Sandbox*

Insurance: Blue Cross    DX1: Colon Cancer/Sigmoid

Last Date of Chemo: 9/28/2005    Referring Dr: Dr Clinton    DCS: 9/28/2005

Cycle: 3    Day/Week: D1    BSA:    Total Charge: $6866.00    View Treatment Sheet Treatment Sheet | Office Visits/Labs/Misc | Vitals/Progress Notes Start Time — End Time — Inf Time (hh:mm)

Reset Times | Auto Start | Auto Stop | Set Inf Time From Clock | Set Inf Time Manually

| Rx | | | Admin | Conc | Dosage | Waste | Qty | Fee | Charge | HCT | Inf Time |
|---|---|---|---|---|---|---|---|---|---|---|---|
| | 0.9 Norr | 0.9 Normal Saline (250 ml) 250 ml | Dilutic | | 750 ml | 0 | 3 | 7 | 21 | | 00:00 |
| | Avastin | Avastin 10 mg | Infusi | | 255 mg | | 40 | 80 | 3200 | | 02:00 |
| | Oxalipla | Oxaliplatin 0.5 mg | Infusi | | 140 mg | | 300 | 10 | 3000 | | 02:00 |
| | 5FU/50 | 5FU/500 MG 500 mg | Push | | 660 mg | 0 | 2 | 5 | 10 | | 00:00 |
| | 5FU/50 | 5FU/500 MG 500 mg | Pump | | 3960 mg | 0 | 8 | 5 | 40 | | 00:00 |
| | Aloxi | Aloxi 0.025 mg | Push | Sec | 0.25 mg | 0 | 10 | 50 | 500 | | 00:00 |
| | | | Infusi | Cor | 350 mg | 0 | 8 | 5 | 40 | | 00:00 |
| | | | | | | | | | | | 00:00 |
| | | | | | | | | | | | 00:00 |

Form View

G-Wiz – Patent Pending – [rptFlow]

Close

DXcodes | ProcsAndCodes | DoctorsAndFees | BillingReports | SurveyOnOff

File  Window  Help

Dr Maya Sandbox

Treatment Sheet for Conrad Pump

Insurer: Blue Cross

| Cycle: 3 | Temp: 98.8 | Height: | Fluids Inf time: | 0:00 |
|---|---|---|---|---|
| Day: D1 | Pulse: 72 | Weight: lbs | Chemo Inf time: | 4:00 |
| | BP: 142/86 | BSA: | Non-chemo Inf time: | 0:00 |

Diagnosis: Colon Cancer/Sigmoid

Karnofsky Value: +02 Normal, no complaints; no evidence of disease

ECOG Value: 0 Fully active, able to carry on all pre-disease performance without restriction Medaport accessed with 20g, 1 inch huber needle. Excellent blood return. Chemo given with no complications. Tegaderm dressing applied over secured huber needle. Patient connected to continuous infusion pump for next 46 hours.

| Proc | Proc Name | Admin Type | Dosage | Waste | Inf Time | Inf Start | Inf Stop |
|---|---|---|---|---|---|---|---|
| J7050 | 0.9 Normal Saline (250 ml) 250 ml | Dilution | 750 | | | | |
| J9035 | Avastin 10 mg | Infusion | 255 | 145 | | | |
| J9263 | Oxaliplatin .5 mg | Infusion | 140 | 10 | | 2:00 | |
| J9190 | 5FU/500 MG 500 mg | Push | 660 | | | | |
| J9190 | 5FU/500 MG 500 mg | Pump (initial) | 3960 | | | 2:00 | |
| J2469 | Aloxi .025 mg | Push | .25 | | | | |
| J0640 | Leucovorin 50 mg | Infusion (Conc) | 350 | 50 | | | |
| 85025 | Complete blood count | | | | | | |
| G0361 | Initial of prolonged chemo, more than 8 hours 1 | | | | | | |

Page: 1

Ready

FIGURE 71

G-Wiz – Patent Pending – [Claims By Date]

Close | DXcodes | ProcsAndCodes | DoctorsAndFees | BillingReports | SurveyOnOff

File  Window  Help

Dr Maya Sandbox

Pump, Conrad
Insurance: Blue Cross

Claim # 1

| Date | Proc | | DX1 | DX2 | Mod | HCT | Qty | Charges |
|---|---|---|---|---|---|---|---|---|
| 9/28/2005 | G0359 | Chemo IV infusion, single/initial drug, 1st hour | 1533 | | | | 1 | $250.00 |
| 9/28/2005 | G0360 | Each additional hour of chemo infusion, up to 8 hours | 1533 | | | | 2 | $150.00 |
| 9/28/2005 | J9035 | Avastin | 1533 | | | | 40 | $3,200.00 |
| 9/28/2005 | J7050 | 0.9 Normal Saline (250 ml) | 1533 | | | | 3 | $21.00 |
| 9/28/2005 | G0361 | Initial of prolonged chemo, more than 8 hours | 1533 | | | | 1 | $300.00 |

Claim charges: $3,921.00

Claim # 2

| Date | Proc | | DX1 | DX2 | Mod | HCT | Qty | Charges |
|---|---|---|---|---|---|---|---|---|
| 9/28/2005 | G0362 | Admin of each additional seq infused drug | 1533 | | | | 1 | $100.00 |
| 9/28/2005 | J9263 | Oxaliplatin | 1533 | | | | 300 | $3,000.00 |
| 9/28/2005 | G0358 | Admin of each additional seq pushed chemo drug | 1533 | | | | 1 | $85.00 |
| 9/28/2005 | J9190 | 5FU/500 MG | 1533 | | | | 10 | $50.00 |
| 9/28/2005 | G0350 | Admin of concurrently infused drug, non-chemo | 1533 | | | | 1 | $40.00 |
| 9/28/2005 | J0640 | Leucovorin | 1533 | | | | 8 | $40.00 |

Claim charges: $3,315.00

Claim # 3

Page: |◄| ◄| 1 |►| ►|

Ready

| Date | Proc | | DX1 | DX2 | Mod | HCT | Qty | Charges |
|---|---|---|---|---|---|---|---|---|
| | Claim # | 2 | | | | | | |
| 9/28/2005 | G0362 | Admin of each additional seq infused drug | 1533 | | | | 1 | $100.00 |
| 9/28/2005 | J9263 | Oxaliplatin | 1533 | | | | 300 | $3,000.00 |
| 9/28/2005 | G0358 | Admin of each additional seq pushed chemo drug | 1533 | | | | 1 | $85.00 |
| 9/28/2005 | J9190 | 5FU/500 MG | 1533 | | | | 10 | $50.00 |
| 9/28/2005 | G0350 | Admin of concurrently infused drug, non-chemo | 1533 | | | | 1 | $40.00 |
| 9/28/2005 | J0640 | Leucovorin | 1533 | | | | 8 | $40.00 |
| | | | | | | Claim charges: | | $3,315.00 |
| | Claim # | 3 | | | | | | |
| Date | Proc | | DX1 | DX2 | Mod | HCT | Qty | Charges |
| 9/28/2005 | G0354 | Admin of each additional seq pushed drug, non-chemo | 1533 | | | | 1 | $40.00 |
| 9/28/2005 | J2469 | Aloxi | 1533 | 78701 | | | 10 | $500.00 |
| 9/28/2005 | 85025 | Complete blood count | 1533 | | | | 1 | $17.00 |
| 9/28/2005 | 99211 | OV Brief | V672 | | | | 1 | $38.00 |
| | | | | | | Claim charges: | | $595.00 |

*** Last date of chemo: 9/16/2005

Bill Release Date:     Original Release Date: 09/30/2005 7:20     Bill charges: $7,831.00

Grand Total: $7,831.00

View/Print Flow Sheet

Select the DOS values for the flow sheet, then click on the View button. A maximum of eight visits can be shown on a sheet. To select a range of DOS values, click on the first DOS in the range, then hold the shift key and click on the last DOS in the range. To select DOS values that are not next to each other, click on the first DOS or range of DOS values, then hold the 'ctrl' key when you select the remaining DOS values. Selected dates will be highlighted.

Patient Name: Florence Flowseet

Dates:

| DOS | Cycle | Day/Wk |
|---|---|---|
| 9/27/2005 | C5 | D1 |
| 10/18/2005 | C6 | D1 |
| 11/8/2005 | C7 | D1 |

[View]

FIGURE 77

| G-Wiz - Patent Pending - [frmTreatment : Form] |
| --- |
| DXcodes | ProcsAndCodes | DoctorsAndFees | BillingReports | SurveyOnOff | Symptoms |
| File Edit View Insert Format Records Tools Window Help |

Close

View/Print Flow Sheet

Select the DOS values for the flow sheet, then click on the View button. A maximum of eight visits can be shown on a sheet. To select a range of DOS values, click on the first DOS in the range, then hold the shift key and click on the last DOS in the range. To select DOS values that are not next to each other, click on the first DOS or range of DOS values, then hold the 'ctrl' key when you select the remaining DOS values. Selected dates will be highlighted.

Patient Name:  Florence Flowseet

Dates:

| DOS | Cycle | Day/Wk |
| --- | --- | --- |
| 9/27/2005 | C5 | D1 |
| 10/18/2005 | C6 | D1 |
| 11/8/2005 | C7 | D1 |

View

Form View

FIGURE 78

| | 09/27/05 | 10/18/05 | 11/08/05 |
|---|---|---|---|
| Vitals | | | |
| Temp | 97.5 | 97.2 | 97.4 |
| Pulse | 84 | 88 | 91 |
| Respiration | | | |
| BP | 102/55 | 138/70 | 133/69 |
| Karnofsky | 100 | 100 | 100 |
| ECOG | 0 | 0 | 0 |
| Labs | | | |
| WBC | | | 14.1 |
| HGB | | | 12.7 |
| Platelets | | | 316 |
| HCT | | | 38.1 |
| Drugs | | | |
| Cycle # | C5/D1 | C6/D1 | C7/D1 |
| 0.9 Normal Saline (50 | 1000 ml | 1000 ml | 1000 ml |
| Alimta | 1000 mg | 1000 mg | 1000 mg |
| Aloxi | 0.25 mg | 0.25 mg | 0.25 mg |
| B-12 | 1000 mcg | 1000 mcg | 1000 mcg |
| IV Site | | | |
| Comment | | | |

Patient Name: Florence Flowseet  DOB: 5/29/1935  Account #: 3550
Diagnosis: Lung cancer - upper lobe  Allergies:
Dr. Maya Sandbox

FIGURE 79

METHOD, SYSTEM AND COMPUTER PROGRAM PRODUCT FOR GENERATING AN ELECTRONIC BILL HAVING OPTIMIZED INSURANCE CLAIM ITEMS

BACKGROUND OF THE INVENTION

1. Field of the Invention

The present invention relates to methods, systems and computer program products for generating an electronic bill having optimized insurance claim items.

2. Background Art

Currently, oncology physicians record the services for the treatment of a patient on a paper checklist. This paper is often called an: Encounter Form; a Superbill; or, in the case of hospital and office examination visits, a Face Sheet. These items are checked off and blanks are filled in to record the therapy and services provided during a patient visit. The sheets of paper tend to be incomplete and prone to errors. They are passed on to human medical billers specialized in oncology billing, who translate the information into a series of medical codes and billing quantities in order to obtain reimbursement from insurance carriers. The codes and requirements change frequently and vary significantly among the different carriers. The ordering of these codes obtain affects timely reimbursement.

The U.S. patent to Rensimer et al. (U.S. Pat. No. 6,154,726) discloses a system that allows the ability to record, transfer, or save medical data from a portable system to a database system. Also disclosed is a means of archiving patient information and generating clinical status codes that can be used for reimbursements from insurance companies.

The U.S. patent to Evans (U.S. Pat. No. 6,347,329) discloses a system comprising
a pen-based portable computer with wireless access to electronic patient records. The system may incorporate legacy files, such as paper files, from a patient's chart.

The U.S. patent to Gilbert (U.S. Pat. No. 6,381,576 B1) discloses a database program employing diagnostic and treatment information data structure that contains both clinical and financial information permitting effective filtering and analysis of Current Procedural Technology (CPT) codes as to accuracy and appropriateness.

The U.S. patent application publication to Porterfield (2002/0077854) discloses a system for determining the best possible billing scenario, in order to maximize reimbursements.

The U.S. patent application publication to Ibok et al. (2002/0116219) discloses a method for wireless accessing a medical record via a PDA, laptop, personal computer (PC) or other telephony device. Also disclosed is a method for secure information transmission using an authentication scheme. The system also includes an interface with existing legacy information.

U.S. patent application publication 2003/0074228 discloses an electronic medical record that is directed towards use in chemotherapy applications.

Electronic medical records in billing scenarios are shown by the following U.S. patents and publications: U.S. Pat. Nos. 6,223,164; 6,655,583; 2002/0091540; 2002/0120466; 2003/0083903; 2004/0204961; 2004/0199404; 2004/0128163; 2002/0123907; 2002/0087358; and 2002/0022972.

SUMMARY OF THE INVENTION

An object of the present invention is to provide an improved method, system and computer program product for generating an electronic bill having optimized insurance claim items.

In carrying out the above object and other objects of the present invention, a computerized method for generating an electronic bill having optimized insurance claim items based on an insurance carrier of a patient is provided. The method includes receiving insurance carrier data which identifies a patient's insurance carrier and patient data which identifies a patient. The method also includes receiving treatment data which identifies a drug administered to the patient and a procedure performed on the patient on a date of service. The treatment data is processed to obtain nurse documentation, such as treatment or flow sheets or drug inventory and reorder forms. An electronic bill is automatically generated having optimized reimbursable insurance claim items including predetermined codes based on the treatment data and the insurance carrier data to facilitate approval of the bill by the insurance carrier.

The treatment data may also identify at least one of: a drug dosage, time spent in administering the drug, and supplies used in administering the drug.

The treatment data may also identify at least one of:
whether the patient brought in a drug, drug name and route of administration;
oncology office visits (especially chemo follow-up visits);
other services (lab work, port flush, etc.);
patient answers to questions, comments and progress notes, ECOG and Karnofsky values;
patient vitals, blood work, and symptoms;
vial size used and actual waste quantities; and
date of service and cycle and day/week.

The treatment sheet may include at least one of: route taken to administer the drug, the names of the drugs in the same concurrent infusion, and time spent to administer the drug.

The treatment sheet may also include at least one of:
any of the treatment data items;
patient name, date of birth, total chemotherapy infusion time, total non-chemotherapy infusion time, signature lines for the doctor and nurse, insurance carrier, primary and secondary diagnosis; and
doctor name and practice.

The method may further include applying an appropriate modifier to at least one claim item on the bill. However, it is possible that a claim may not need any modifiers.

The method may further include adding at least one predetermined code required for reimbursement of the drug or the procedure. For example, both the J-Code and sometimes a DX2.

The method may further include verifying that HCT level is recorded and meets a minimum level required for reimbursement of the drug by the insurance carrier.

The method may further include generating remarks containing at least one of: a predetermined code, drug name, drug dosage, drug waste and route taken in administering the drug.

The method may further include generating remarks to document when the patient provides the administered drug to ensure reimbursement for administration of the patient-provided drug.

The drug may be a chemotherapy or non-chemotherapy drug administrated to the patient. The method may include issuing the appropriate code for the administration of the chemotherapy or non-chemotherapy drug.

The method may further include applying a predetermined code to distinguish between types of administrations and any concurrent infusions.

The method may further include determining a correct set of codes and respective quantity fields to bill the correct representation of infusion times, drug quantities, including waste and administration counts.

The method may further include disallowing multiple drug administrations unless a predetermined code is included on the bill.

The method may further include generating a claim item with an associated predetermined code. A total dosage of the drug may be substantially equal to a sum of the dosages of the multiple drugs.

The method may further include ordering the claims and sequencing the claim items of the claims in a manner to facilitate approval of the bill by the insurance carrier.

Related administered drugs and their respective predetermined codes may be grouped together in a single claim.

The method may further include tracking of chemo follow-up visits.

The method may further include precisely estimating drug waste.

The method may further include collecting and generating the appropriate documentation in the treatment sheet to corroborate the claim.

The method may further include suggesting charges via prompts.

The method may further include tracking of elapsed infusion times.

The method may further include tracking cycle-day/week and providing default dosages.

The method may further include generating various fee schedules to accommodate data entry into a billing software system and to facilitate financial analysis of patient encounters.

The method may further include the tracking of drug usage in order to maintain inventory and to automate the ordering of drugs for the practice.

Further in carrying out the above object and other objects of the present invention, a system for generating an electronic bill having optimized insurance claim items based on an insurance carrier of a patient is provided. The system includes a processor which is operable to execute computer program instructions. The system further includes a memory which is operable to store computer program instructions executable by the processor. Computer program instructions are stored in the memory. The computer program instructions receive insurance carrier data which identifies a patient's insurance carrier and patient data which identifies a patient. The computer program instructions receive treatment data which identifies a drug administered to the patient and a procedure performed on the patient on a date of service. The computer program instructions process the treatment data to obtain nurse documentation, such as treatment or flow sheets or drug inventory and reorder forms. The instructions automatically generate an electronic bill having optimized reimbursable insurance claim items including predetermined codes based on the treatment data and the insurance carrier data to facilitate approval of the bill by the insurance carrier.

The treatment data may also identify at least one of: a drug dosage, time spent in administering the drug and supplies used in administering the drug.

The treatment sheet may include at least one of: route taken to administer the drug, the names of the drugs in the same concurrent infusion and time spent to administer the drug.

The instructions may apply an appropriate modifier to at least one claim item on the bill.

The instructions may add a predetermined code required for reimbursement of the drug.

The instructions may verify that HCT level is recorded and meets a minimum level required for reimbursement of the drug by the insurance carrier.

The instructions may generate remarks containing at least one of: a predetermined code, drug name, drug dosage, drug waste and route taken in administering the drug.

The instructions may generate remarks to document when the patient provides the administered drug to ensure reimbursement for administration of the patient-provided drug.

The drug may be a chemotherapy drug administrated to the patient, and the instructions may issue the appropriate code for the administration of the chemotherapy drug.

The instructions may apply a predetermined code to distinguish between types of administrations and any concurrent infusions.

The instructions may determine a correct set of codes and respective quantity fields to bill the correct representation of infusion times and administration counts.

The instructions may disallow multiple drug administrations unless a predetermined code is included on the bill.

The instructions may generate a claim item with an associated predetermined code wherein a total dosage of the drug is substantially equal to a sum of the dosages of the multiple drugs.

The instructions may order the claims and sequence the claim items of the claims in a manner to facilitate approval of the bill by the insurance carrier.

Related administered drugs and their respective predetermined codes may be grouped together by the instructions in a single claim.

Still further in carrying out the above object and other objects of the present invention, a computer program product for generating an electronic bill having optimized insurance claim items based on an insurance carrier of a patient is provided. The computer program product includes a computer readable medium. The computer program product further includes computer program instructions recorded on the medium and executable by a processor to: receive insurance carrier data which identifies a patient's insurance carrier and patient data which identifies a patient; receive treatment data which identifies a drug administered to the patient and a procedure performed on the patient on a date of service; process the treatment data to obtain nurse documentation, such as treatment and/or flow sheets; and automatically generate an electronic bill having optimized reimbursable insurance claim items including predetermined codes based on the treatment data and the insurance carrier data to facilitate approval of the bill by the insurance carrier.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIGS. 1-79 are screenshots generated by a computer programmed with one embodiment of a computer program product of the present invention.

DETAILED DESCRIPTION OF THE PREFERRED EMBODIMENTS

Figure 1:
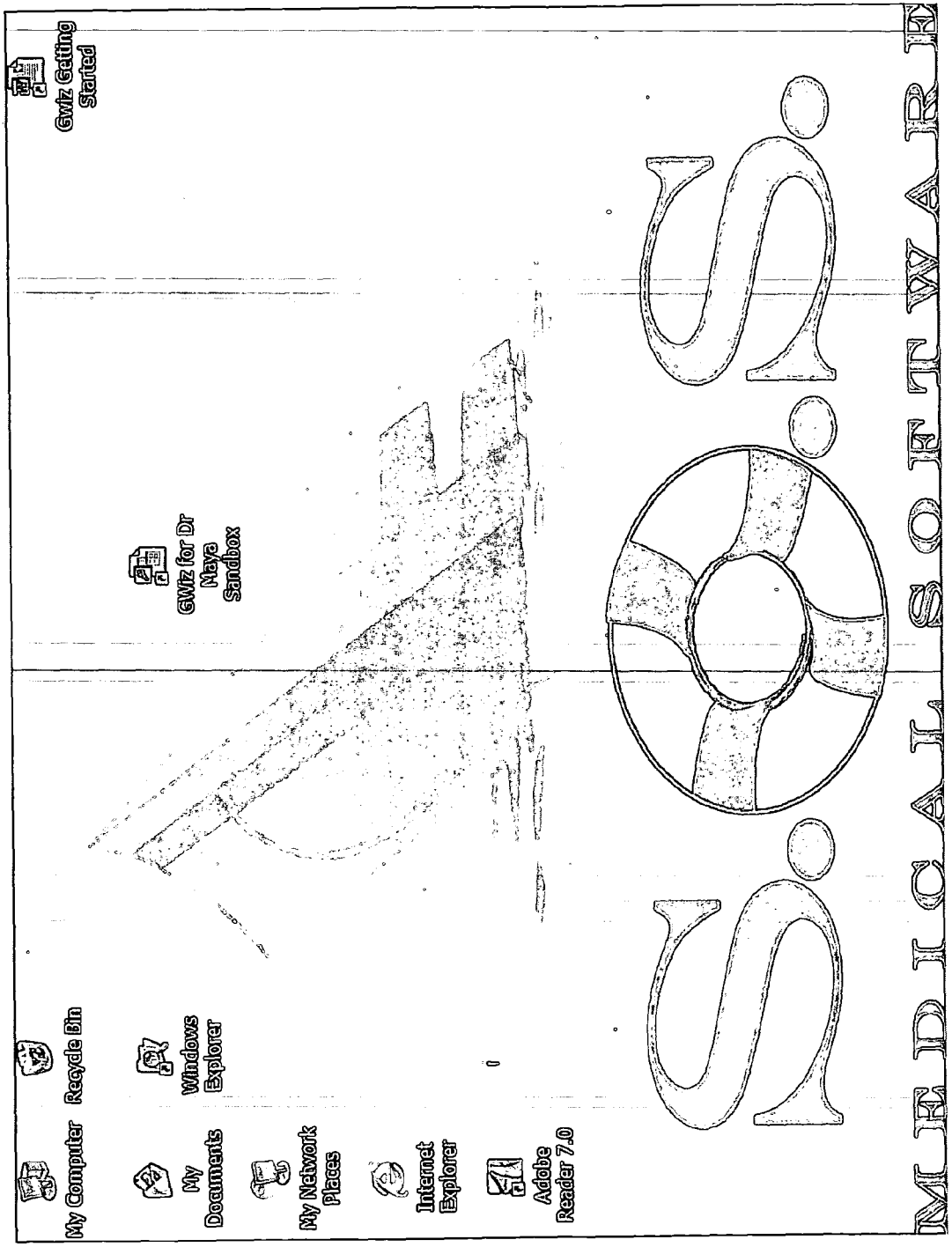

Improve Cash Flow by Expediting Claim Approval

An objective of the computer application is to increase cash flow. Two avenues pursue this: expediting claim approval and maximizing reimbursement. The first is by striving to obtain the approval of claims during an insurance adjudicator's initial review; thereby, avoiding additional intervention.

Namely: resubmissions, phone calls, and Statuses. The computer application pursues this by consistently:

1. Applying the appropriate Modifier to claim line items. A 25 Modifier is necessary for Office Visits on the same day as chemotherapy or non-chemotherapy, except if the insurance is Blue Cross. A 25 Modifier is also required for Level I Office Visits to Medicare when there are no other services provided on the same day. A 59 Modifier is required for Hydration unless it is the primary procedure for the day. Refilling and maintenance of portable pump (96520) and Introduction of needle or intracatheter, vein (36000) always require a 59 Modifier. Medicare requires a 59 Modifier for Phlebotomy, therapeutic (99195). A 76 Modifier is required for the reimbursement of Introduction of needle or intracatheter, vein (36000) to multiple sites.
2. Verifying the coding of the proper primary diagnosis code for certain procedures. For example, a Phlebotomy, therapeutic (99195) requires Hemochromatosis (2750) or Polycythemia Vera (2384).
3. Providing a secondary diagnosis code for certain procedures that demand one for reimbursement, e.g., Urinalysis (81000) in an oncology setting requires a secondary diagnosis code of 7910 (Proteinuria). The user defines this relationship in ProcsAndCodes.
4. Including a secondary diagnosis code, when it is required for the reimbursement of a drug. The application allows the user to optionally define one secondary diagnosis per drug (or procedure) in ProcAndCodes. Some drugs require a different secondary diagnosis codes depending upon the primary diagnosis of the patient, which the application accommodates through logic within the program code.

| Program Logic for Procrit (Q0136) and Aranesp (J0880) | | | |
|---|---|---|---|
| If DX1 | Description | DX2 | SECONDARY DIAGNOSIS |
| 1400 to 20497 | Cancer | 28522 | Anemia in Neoplastic Disease |
| 28529 | Anemia of Chronic Disease | 2859 | Anemia |
| 585 | Chronic Renal Failure | 2859 | Anemia |
| 2387 | Myelodysplastic Syndrome | 2859 | Anemia |

| Suggested Secondary Diagnosis Entries in ProcsAndCodes | | | |
|---|---|---|---|
| DRUG | J-CODE | DX2 | SECONDARY DIAGNOSIS |
| Cimetidine | J3490 | 78701 | Nausea with Vomiting |
| Atropine | J0460 | 78791 | Diarrhea |
| Prochlorperazine | J0780 | 78701 | Nausea with Vomiting |
| Dexamethasone | J1100 | 78701 | Nausea with Vomiting |
| Diphehydramine | J1200 | 78701 | Nausea with Vomiting |
| Anzemet | J1260 | 78701 | Nausea with Vomiting |
| Filgrastim/ Neupogen | J1440 | 2880 | Agranulocytosis |
| Filgrastim/ Neupogen | J1441 | 2880 | Agranulocytosis |
| Polygam/ Gammunex | J1563 | 27903 | Oth Selective Immunoglobulin Defic |
| Kytril | J1626 | 78701 | Nausea with Vomiting |
| Iron | J1750 | 2809 | Anemia/Iron Deficient |
| Mannitol 25% | J2150 | 59582 | Irradiation Cystitis |
| Sandastatin Lar | J2353 | 78791 | Diarrhea |
| Oprevelkin/ Neumega | J2355 | 2874 | Secondary Thrombocytopenia |
| Zofran | J2405 | 78701 | Nausea with Vomiting |
| Pamidronate/ Aredia | J2430 | 1985 | Malignant Neoplasm Bone & Bone Marrow |

| Suggested Secondary Diagnosis Entries in ProcsAndCodes | | | |
|---|---|---|---|
| DRUG | J-CODE | DX2 | SECONDARY DIAGNOSIS |
| Aloxi | J2469 | 78701 | Nausea with Vomiting |
| Neulasta | J2505 | 2880 | Agranulocytosis |
| Metocloropramide | J2765 | 78701 | Nausea with Vomiting |
| Solumedrol | J2930 | 78701 | Nausea with Vomiting |
| B-12 | J3420 | 2810 | Folate Deficiency Anemia |
| Zometa | J3487 | 1985 | Malignant Neoplasm Bone & Bone Marrow |
| Lupron | J9217 | 1985 | Malignant Neoplasm Bone & Bone Marrow |
| Faslodex | J9395 | 1985 | Malignant Neoplasm Bone & Bone Marrow |

5. Ensuring that the HCT Level is recorded and meets the required minimum level (38.5 or less), as necessitated for the reimbursement of certain drugs, such as: Procrit (Q0136) and Arenesp (J0880).
6. Creating Remarks containing J-Code, Drug Name, Amount Used (Dosage plus Waste), Route (Injection, IV, or Push), and NDC Number for drugs, which do not have their own unique J-Code assigned to them and now share J3490 or J9999 with other drugs.
7. Generating the necessary Remarks to document a patient bringing their own drug, assuring reimbursement for the administration of that drug. The computer application includes: J-Code, Dosage, and Route in the Remarks.
8. Issuing the appropriate G-Code for chemotherapy injections to distinguish between Hormonal and Non Hormonal Agents among the chemotherapy J-Codes. At this time, Faslodex, Lupron, and Zoladex comprise the set of Hormonal Chemotherapy Injections.
9. Applying the proper G-Code to distinguish between: Chemotherapy Injections, Pushes, and Infusions; and Non-Chemotherapy Injections, Pushes, Sequential Infusions, and Concurrent Infusions. Also, determining the correct set of G-Codes with their respective quantity fields to bill the correct representation of infusion times and administration counts.
10. Providing the proper coding for 5FU pump administration. To infuse the drug 5FU for more than eight hours, pumps are used. Usually, the patient receives a Push followed by either a Pump Refill or Pump Initiation procedure. Generally, Medicare only allows one administration code per drug per day of service, but pumps are an exception to this rule. The computer application disallows multiple 5FU administrations unless a pump administration code is included. Then the billing algorithm generates three claim lines: the code for Push, the code for the pump administration; and the J-Code for the 5FU with a total quantity representing the sum of both dosages. The application records both dosages next their respective routes in the Treatment Sheet for the patient's chart. The billing algorithm applies a 59 Modifier to Pump Refills.
11. Building claims and sequencing claim line items in a logical fashion to facilitate adjudication, accommodating the most restrictive format, the HFCA 1500 six-line claim. The application contains a billing algorithm, which subdivides a patient encounter into Units for Approval, exhibited to an insurance adjudicator as packets of claim lines. Each packet begins with one or more closely related procedure codes pertaining to the same specific administration and technique followed by the J-Codes of the drugs administered by that method.

Instead of a deluge of haphazard codes, the adjudicator views an orderly series of services separated into Chemotherapy Infusions, Pushes, Injections, Therapeutic/Diagnostic Infusions, Pushes, and Injections; as well as Hydrations and Pump Administrations. Immediately, after each of these techniques, follow the administered drugs. This assists the adjudicator by presenting coherent groups easily recognized as being complete and appropriate with all the necessary secondary diagnosis codes and modifiers. They appeal to the insurance adjudicator's need to easily decipher the required prerequisites, increasing the likelihood of approval. If rejected, the biller can more easily reprocess them, since they form distinct and cohesive subsets.

E.g., Hydration as: 36000 Introduction of needle or intracatheter, vein followed by G0346 Hydration followed by J7030 Saline. Note: For clarity, the algorithm places Introduction of needle or intracatheter, vein (36000) before the associated hydration, infusion, or push that flows through it.

E.g., A non-chemotherapy infusion as: G0348 Intravenous infusion, for therapy/diagnosis; each additional hour, up to eight hours with a quantity of three followed by Intravenous infusion, for therapy/diagnosis; G0349 Additional sequential infusion, up to one hour with a quantity of one followed by J2150 Mannitol.

E.g., Chemotherapy pushes as: G0358 Chemotherapy administration, intravenous; push technique with a quantity of three followed by J9040 Bleomycin, J9000 Adriamycin, and J9360 Vinblastine.

One could consider a Port Flush to be a Unit for Approval, but currently, there are no reimbursable J-Codes to accompany it. In addition, Office Visits and Lab Procedures do not have J-Codes associated with them. Since, these procedure codes have no contextual relationships with other claim lines, sequencing them is not important. They occupy the last lines of the last claims for the patient encounter. Likewise, the algorithm places saline (except when the insurance is Blue Cross) and other supplies among the final lines for the encounter.

The algorithm endeavors to present the Units for Approval on separate six-line HFCA 1500 formats for the sake of clarity to the adjudicator, but not at the expense of generating extra claims needlessly. For example: An Injection procedure code with its accompanying drug only consumes two claim lines, which would result in four blank HFCA 1500 lines. Another Unit for Approval could fit on the same claim.

For non-chemotherapy drugs, the billing algorithm insures that there are not more than three unique Secondary diagnosis codes on the claim. The HFCA 1500 Claim format has a limit of four unique diagnosis codes per claim. Since one must be primary, only three remain for use as unique secondary diagnosis codes.

The billing algorithm encodes the Units for Approval for a specific Date of Service constructing a series of packets packaged into claims. Each Unit of Approval is discernable as there are one or more procedure codes at the beginning followed by one or more J-Codes at the end, resulting in all drugs in proximity to their respective techniques and administration. Within the same claim, a G-Code always has at least one of its related J-Codes following it. However, because a procedure may administer many drugs, the algorithm may have to split some of the drugs to the beginning of the next six-line claim. The algorithm splits off the least expensive drugs in the packet.

Generally, all chemotherapy items would be on the first and second claims; followed by non-chemotherapy items flowing into additional claims and Laboratory, Office Visits, and Supplies would appear on the last claims. Together all of the claims represent the complete patient encounter for the Date of Service.

While this describes the overall strategy of the billing algorithm, the first claim for a patient encounter demands some specific tactical ordering of claim lines:

1) An Initial G-Code appears on the first line of the first Claim, except if there is an Introduction of needle or intracatheter, vein (36000). The procedure code 36000 always appears before the procedure using the needle or intracatheter. Thus, the Initial G-Code would appear on the second line.
2) If there are additional hours (G0360 or G0348), they appear next.
3) The most expensive drug administrated by the preceding G-Codes follows.
4) If the encounter warrants reimbursement for the Medicare Demonstration Project, then the three G90nn-Codes fill the remaining lines of the first claim.

At this point, an adjudicator should readily approve the Demonstration Project Codes for reimbursement. Answers to all three of survey questions are readily apparent, as they are together in one group. It is evident that the patient received chemotherapy by a Push or Infusion, since one of these chemotherapy administration G-Codes appears immediately before the administered chemotherapy drug.

All of this is determined by looking at only one claim. Because these line items make up such a simple claim (similar to boilerplate), the entire claim is almost certain to obtain immediate approval. Inclusion of the most expensive chemotherapy drug into this first claim makes good sense because the adjudicator should not find anything to doubt.

5) For claims to Blue Cross, there are no Demonstration Project Codes to bill. In their place, the billing algorithm generates claim lines for the Saline Supplies because Blue Cross requires them to be in the same claim with the Primary (Initial) Procedure Code.
6) If are at least two available lines remain and there are more procedures to bill, the algorithm generates another procedure code and drug(s). The algorithm never generates a procedure code without at least one J-Code following it. If there are still more J-Codes associated with the procedure, they spill onto the beginning lines of the second claim.
7) If there are no more procedures to bill, the algorithm fills the remaining lines of the first claim with supplies and/or Office Visits/Labs/Misc.
8) The billing algorithm then resumes its overall strategy of generating claims and claim lines for the remaining services.

The method described is subject to modification as better strategies become apparent or as reimbursement criteria changes, e.g., Medicare eliminates the Demonstration Project Codes.

Improve Cash Flow by Maximizing Reimbursement Revenue

The second avenue to improve cash flow is maximizing reimbursement revenue. The application accomplishes this by reminding the user of additional expense items eligible for reimbursement, that are not generally well known, often because they vary by insurance. For example:

1. Medicare currently pays for the Demonstration Project Codes, but only if the patient received chemotherapy administered by a Push or Infusion and answered all three of the Survey Questions. The doctor can insist that the application always bill for the Demonstration Project, which results in the computer application forcing the user to answer all three of the Survey Questions when the Date of Service qualifies for the reimbursement. The application does not force answers or bill the Demonstration Project Codes for patients that received chemotherapy by Injection or for patients that do not have a cancer diagnosis. For example, Multiple Sclerosis (340) patients receiving Mitoxantrone/Novantrone (J9293).

2. Carriers will reimburse for drug waste. The computer application provides a Waste field next to the dosage of each drug administered. If the treatment resulted in Waste, recorded by the nurse or estimated by the application, it is included as part of the reimbursement quantity. The application currently uses the HCPS Billing Quantity to provide a minimum estimate for Waste. However, it can under report much of the entire amount; Proper entry by the nurse is important. The application is able to store the actual vial sizes in ProcsAndCodes. By subtracting the entered dosage from the drug and vial size selected by the nurse, the application can obtain a precise Waste estimate; covering most instances involving Single-Use Vials.

3. Medicare will not provide for the reimbursement of 99211 (Level I Office Visit) on the same day that a patient receives chemotherapy or non-chemotherapy, but most insurance carriers will. When a patient receives chemotherapy or non-chemotherapy and the insurance will reimburse for an office visit on that same day, the computer application prompts the user for a Level I Office Visit (99211). The user can accept or deny this charge or issue a higher level of Office Visit. Hence, the application issues prompts offering 99211 for Blue Cross, Blue Care Network, Medicaid, Other Insurances, and PPOM, but not for Medicare. The Application strives to reduce the volume of Explanation Of Benefits (EOB) error messages to prevent important messages from being lost. Thus, the application blocks the user from billing a Nurse Charge to Medicare on Dates Of Service with chemotherapy or non-chemotherapy, thereby avoiding the denial messages.

4. Blue Cross will pay for up to three Chemotherapy Follow Up Visits within thirty days of the last date of chemotherapy with no co-payment to the patient. The application tracks these visits and notifies the user when the patient is eligible for reimbursement of a Chemo Follow Up Visit. If the user issues an Office Visit Charge and the computer application determines that this visit qualifies as a Chemo Follow Up, the computer application prompts the user for confirmation. If the user concurs, the billing algorithm generates the Office Visit Charge with a V672 secondary diagnosis code, preventing a co-payment bill to the patient. The billing algorithm ensures that a 25 Modifier is not present, since it would result in a rejection by Blue Cross.

5. Blue Cross will not pay for Saline Supplies unless they are in the same claim as the primary procedure code. Therefore, for Blue Cross, the billing algorithm places charges for Saline Supplies in first claim, since it always contains the Initial G-Code.

6. A Port Flush does not normally qualify for reimbursement, since the procedure and its supplies are almost always bundled with other services. If a nurse provides a port flush with no other procedures other than Labs on the same day, a Port Flush (G0363) is reimbursable. The supplies, i.e. Saline Sterile 5 cc and either Heparin or Heplock, are bundled into the Port Flush procedure. G0363 pays more than a Nurse Charge (99211) will, even if you include the fees for the Saline and either Heparin or Heplock, which are no longer reimbursable anyhow.

The computer application lists any Selected port flush supplies in the Patient Treatment Sheet, but never bills them because they are always bundled expenses. They are not reimbursable. They only result in adding to the volume of rejection messages in the EOB, making it more difficult to identify inappropriately denied revenue.

If the user selected a Port Flush and services other than Labs were performed, the application records the Port Flush in the Treatment Sheet, but does not bill it because it is not reimbursable.

If the user selected port flush supplies, i.e. Saline Sterile 5 cc and either Heparin or Heplock with no other services, except Labs and the user did not select G0363 (Port Flush), the application issues a prompt suggesting a Port Flush.

When the computer application identifies an encounter with port flush supplies along with a Nurse Visit (99211) and no other services, except for Labs, the computer application suggests the alternative charge.

7. For Blue Care Network, PPOM, and Other insurances (That is—not Blue Cross, Medicaid, or Medicare), if the Introduction of needle or intracatheter, vein occurred, the practice can receive additional reimbursement by billing procedure code 36000. The computer application queries for this procedure on every Infusion, Push, and Hydration. The application records the procedure in the Patient Treatment Sheet regardless of insurance, but only bills it to Blue Care Network, PPOM, and Other. For Blue Care Network, PPOM, and Other, the application queries for a second site. If there were two separate IV Sites for this patient, the application includes a 76 Modifier with the second 36000.

8. Blue Care Network, PPOM, and Other insurances will pay for Chemo Kits, when billed as 99070 for PPOM and A4221 for Blue Care Network and Other. Blue Cross, Medicaid, and Medicare insurances consider the kits to be bundled and will reject the charges. If the insurance is Blue Care Network, PPOM or Other and the patient received chemotherapy or non-chemotherapy by a Push or Infusion; the computer application offers the billing of 99070 or A4221. For PPOM, which requires Remarks accompanying the charge, the computer application generates a Remarks Field containing "Chemo Kit".

9. Drugs Etoposide (J9181 & J9182), Taxotere (J9170) and Taxol (J9265) require special Non-PVC Tubing (S1016). This is a Bundled Expense to Blue Cross, Medicaid, Medicare, and PPOM. Because Blue Care Network and Other commercial insurances will reimburse this as a separately expensed item, the computer application detects these drugs and when the insurance is Blue Care Network or Other, offers to bill for the tubing.

10. Huber Needles (A4212), used during Port Flushes, are a Bundled Expense to Blue Cross, Blue Care Network, Medicaid, Medicare, and PPOM. However, Other commercial insurances will reimburse this as a separately expensed item. The computer application monitors the use of 5 cc of Saline with either Heplock or Heparin. If the insurance is Other, the application prompts for the billing of a Huber Needle (A4212).

11. There are Pump Supplies (A4222) used in the Initiation or Refill of a Pump. Blue Cross, Medicaid, Medicare, and PPOM consider these expenses bundled. However, it is payable by Blue Care Network and Other insurances. Therefore, the computer application checks for pump administration codes and issues a prompt suggesting the billing of Pump Supplies (A4222) if the insurance is Blue Care Network or Other.

12. Allowable reimbursement items change over time and vary by region, which will result in changes to the application as needed.

Another endeavor of the computer application to maximize reimbursement revenue is to validate that the user has entered the proper amounts of drugs, supplies, and times into the computer application.

To ensure that the practice is obtaining full compensation for all of the infusion times, the computer application checks the actual infusion times against the expected infusion times. Actual times that are lower than expected would cause the computer application to query the user, asking if the entered time is indeed what was desired.

There is a tendency for nurses to record infusion time as the time stated in the Protocol. The Protocol specifies infusion times in quarter hour or half hour increments. Medicare billing units are to the nearest hour with 30 minutes or less to be 'rounded down'. In addition, Medicare defines Infusions of 15 minutes or less to be Short Infusions, requiring the biller to bill them as a Push. However, the Medicare billing units are for Actual time. It is very possible that the Actual time will differ from the stated Protocol time.

The computer application offers the user the option to enter the actual start and stop times from which the computer application can calculate the elapsed time. These serve as journal entries, logged in the Patient Treatment Sheet for supporting documentation. In addition, the user can use the application in real time for Hydration and Infusions. Auto Start and Auto End Buttons serve as a stopwatch.

For Infusions close to billing unit thresholds, the computer application alerts the user, notifying that a 'rounding down' of an Additional Hour of Infusion Time is about to occur or that an Infusion is going to be billed as a Push. This gives the user an opportunity to confirm that the correct Actual elapsed time has indeed been entered and allows the user to make corrections and to record specific time of day entries if desired.

The nurse must infuse a drug for more than 90 minutes in order to bill for an Additional Hour. The program notifies the user when it cannot generate an Additional Hour of Infusion Time because the infusion time is close to, but not greater than 90 minutes.

For "Short Infusions", the application notifies the user, with a message, Warning: Infusion times of 15 minutes or less will be billed as pushes. The application reports this as an Infusion on the Treatment Sheet, but bills it as a Push.

The computer application offers the user the option to enter Cycle-Day/Week for each patient chemotherapy encounter. The computer application provides a list of patient encounters with the Cycle-Day/Week. Omissions in the Cycle-Day/Week series are evidence of missing patient encounters. Perhaps, they were misplaced or forgotten. This would result in lost revenue if not discovered.

Because of the effort to remember every treatment item, the computer application offers the ability to select a previous patient encounter using Cycle-Day/Week as a guide and copy it with a new Date Of Service. This saves keystrokes, but also the listed drugs, supplies, and procedures serve to remind the user of what to bill. The application does not copy the patient Vitals and Comments, since they are likely to change.

This will be by deducting the error from a future claim, causing confusion for the billing department, and wasting more staff time.

To facilitate accurate data entry of individual claim lines into the billing software, the computer application generates a total dollar amount for each claim in the Superbill. The computer application assigns a dollar amount to each claim line according to the fee schedule established by the practice in ProcsAndCodes. It is highly recommend that these dollar amounts be identical to the fees in the billing software for the practice. Upon completion of data entry for a claim, most billing software products show a dollar total. If the fee schedule of the computer application is identical to the fee schedule in the billing software these totals should agree. Thus, the biller can conclude that the claim items have been transferred into the billing software accurately.

The computer application allows multiple fee schedules to be established. This allows the practice to maintain a fee schedule of allowed amounts for each carrier. The user can direct the computer application to apply different sets of fees to the Superbill. Hence, the practice can see the expected revenue for each patient encounter by insurance carrier. If the practice also creates a fee schedule with the practice's estimated cost of each claim line, the user can generate a 'variable cost' report. That is—a report showing the estimated variable cost for each encounter. When compared to the expected revenue for the encounter, an estimate of marginal profit per encounter can be determined.

The computer application tracks the usage of pre-mixed drug bags and drug vials in order to maintain inventory for the practice. In ProcsAndCodes, each drug has an associated: Items on Hand; a minimum and maximum threshold for ordering; and a reorder quantity. The application produces a report showing the usage of drugs during a date range. For practices that perform "just in time inventory controls", the usage of drugs by vial size during the previous week can be used to determine the anticipate order to be placed for the following week. The computer application provides for the update of number of Items on Hand as drug shipments are received.

Improve Office Productivity

The computer application instantly improves office productivity because it eliminates the necessity of a chemotherapy nurse to translate the patient's chart into a superbill by hand. The nurse does not have to learn medical reimbursement coding rules and procedures. The nurse merely records the patient treatment, as a matter of normal charting necessity.

However, the success of any computer application depends upon the accuracy and completeness of the data entered. Using a computer keyboard and mouse does require extra effort over hand written notes. The computer application makes every attempt to maximize the utility of the entered data by automating other tasks, normally performed by the nurse. The strategy is that the more the nurse is "rewarded" through the elimination of laborious and tedious tasks, the more conscientiously the nurse will embrace the use of the computer application.

Toward this end:

1. The computer application allows the nurse to enter the dosages only in the appropriate unit of measure for the patient's chart rather than the HCPS Billing Units that are required for billing.
   a. For example, the nurse will enter the Mannitol dosage in grams. The billing algorithm automatically converts it to HCPS Billing Units of 50 ml.
   b. The nurse will enter Aloxi in multiples of 0.25 mg. The billing algorithm converts the dosage to the equivalent HCPS Billing Units of 25 mcg, resulting in a Billing Quantity of 10 or multiples thereof.
   c. The nurse will enter Kytril as milligrams. The billing algorithm converts this into the HCPS Billing Units of 100 micrograms. Thus, a dosage entry of 1 mg results in a HCPS Billing Quantity of 10.

d. The nurse administers certain drugs and fluids (5FU, Mannitol, Mesna, Procrit, Saline, Vidaza) multiple times. If the drug's definition in ProcsAndCodes indicates Multiple entries allowed, the program permits the reporting of multiple drug entries. The application lists each entry in the Treatment Sheet in the sequence reported by the nurse. The billing algorithm generates a claim line with one J-Code, summing the multiple dosages to calculate the appropriate HCPS Quantity.

e. The nurse can select the package size of drugs or supplies, such as Saline, that have multiple J-Codes to designate different package sizes. The application reports the total dosage in the Treatment Sheet, but bills the multiple J-Codes with their respective HCPS Quantities.

2. In ProcAndCodes, the user can provide default dosages. This is especially useful for drugs that have the same dosage regardless of patient BSA. The application also provides a default dosage per BSA for certain drugs.

Suggested Default Dosages in ProcsAndCodes

| DRUG | J-CODE | DOSAGE | MEASURE |
| --- | --- | --- | --- |
| Anzemet | J1260 | 100 | mg |
| Neupogen | J1440 | 300 | ug |
| Neupogen | J1441 | 480 | ug |
| Kytril | J1626 | 1 | mg |
| Aloxi | J2469 | .25 | mg |
| Neulasta | J2505 | 6 | mg |

3. From ProcsAndCodes entries, the application knows which drugs are Single Use Vials. The application estimates the minimum Waste for Single Use Vials by subtracting the Dosage from the product of the HCPS Billing Quantity times the HCPS Billing Units. The application pre-fills the Waste field with this estimate, which is often close enough. The nurse modifies the estimate as necessary. (For Multiple-Dose Vials, the Waste field remains blank, until the nurse enters an amount.) The application also allows for the selection of different vial sizes for drugs that have multiple Single-Use Vial sizes, but only one J-Code. This allows the application to provide a precise Waste value, accurate in most cases, to relieve the nurse of calculating Waste with by hand.

4. The application generates a Treatment Sheet, which itemizes for a patient Date of Service: Drugs Administered, Dosages, Waste, Routes of Administration, and Times for both chemotherapy and non-chemotherapy Infusions. Also, included are the patient's name and primary diagnosis. For Medicare patients, the application also includes the answers to the Survey Questions. Blank signature lines for the nurse and doctor appear at the bottom. This comprises the beginning of an Electronic Medical Records (EMR) System to which the practice can augment additional patient chart entries. With the additional entries, the application holds a significant variety of patient data, capable of answering simple questions. Querying the application instead of searching and pulling patient charts saves the practice a significant amount of time. For example, the nurse can order drugs for next week's treatments solely by accessing the application without the pulling of individual patient charts. The more times the practice views each data item, the more they can attest to its accuracy.

5. If the patient received chemotherapy, the application prompts for Cycle-Day/Week, as optional input from the user. When entered, the application includes them in the Treatment Sheet. The application does not permit duplicate Cycle-Day/Week entries nor does it assign a Cycle-Day/Week to a Date of Service when there was no chemotherapy performed.

6. The computer application allows the user to enter Progress Notes for each patient encounter and patient Vitals (Blood Pressure, Temperature, Pulse, ECOG and Karnofsky Performance Status). In addition, the nurse can enter Height and Weight, from which the DuBois and Dubois Body Surface Area (BSA) is calculated. When provided, these are included in the patient Treatment Sheet. The nurse can place the Treatment Sheet into the patient's chart, eliminating the task of consolidating other notes and slips of paper. Sometimes carriers demand progress notes, which the application can store in its database. The nurse or biller can merely print them and avoid retrieving the patient's chart. This is especially valuable when the biller is off site. The application is able to store blood laboratory results and patient symptoms, including them as part of the Treatment Sheet. The application provides a Blood Work Tab and a Symptoms Tab for data entry. The application checks the blood work values for reasonableness, rejecting absurd values and highlighting abnormal values. The application provides the user with the ability to define a standard set of values for seven different symptoms (nausea/vomiting, diarrhea/constipation, pain, fatigue, numbness, shortness of breath, and mucositis). For example, the patient often describes pain values on a scale of one to ten.

7. The computer application generates Flow Sheets automatically. These are sheets of paper illustrating patient progress resulting from chemotherapy and the administration of therapeutic drugs. Essentially, this is a one-page summary of the drugs administered over a series of days to compare against subsequent blood results for the patient. For each Date of Service, this contains the Cycle-Day/Week and each drug administered with Dosage. Also, included for each day are the patient's Vitals, Symptoms, and Blood Work. The application allows the user to designate a series of individual Dates of Service from a list annotated with corresponding Cycle and Day/Week entries. The application prints the selected entries on the Flow Sheet. To accommodate the vast number of different blood tests, the application only prints results with non-blank values of the Flow Sheet.

8. Because many patients receive the same chemotherapy regimen, the computer application allows the user to copy the encounter of one patient to another patient. If the patient encounters are similar, the user avoids data entry time for most of the encounter. Again, the application copies the drugs and administrations, but not Infusion Times, or Vitals.

An objective of this application is to minimize the total number of rejection messages that appear on EOBs. Of significant concern are rejections that are superfluous, not requiring follow-up or rebilling. These typically result when a practice attempts to maximize revenue by billing for items that are not reimbursable in all instances. A practice might bill the Medicare Demonstration Project for every Medicare patient encounter, resulting in rejections for Dates of Service that do not qualify, i.e., patients that did not receive chemotherapy, patients that received chemotherapy by Injection or Multiple Sclerosis patients receiving chemotherapy.

It is difficult for the staff to remember the few exceptions as to when this charge is not appropriate; so, they bill it for all Medicare encounters. However, this results in legitimate rejection messages from Medicare. These additional rejections tend to obfuscate the truly important rejections that the biller needs to recognize as soon as possible for prompt follow-up. In addition, the Accounts Receivable becomes deceiving because the illegitimate expenses overstate the expected revenue stream. The biller must apply numerous Write-Offs to the billing software during the posting of payments, reconciling invalid charges. If Medicare mistakenly approves these charges, Medicare will later seek to reclaim the money. This will be by deducting the error from a future claim, causing confusion for the billing department, and wasting more staff time.

Operating Environment

Currently, the computer application runs as a Stand Alone Windows Application with no prerequisite software. It can run on Windows 98, Windows 2000, or Windows XP (Home or Professional). The user can install the software on any PC, but most will prefer to have the computer application located on a workstation located in the nurse's area. Because this area is usually quite small and cramped, we have found it advantageous to implement the computer application on a small laptop with a 12-inch screen. In order to reduce incidents of virus and spy ware corruption, it is also desirable for the workstation to be dedicated only to this computer application.

For these reasons, plus the desire to have a limited set of hardware/software operating system environments, SOS-Medical Software provides both the hardware and the software as part of the product package. At this time, the operating environment consists of a 12-inch screen laptop with a laser printer to be entirely dedicated to running the computer application. It may be desirable to have the work station connected to the internet or at least to a telephone line, so that a remote access program, such as PC Anywhere can allow remote maintenance and error correction.

For larger practices and clinics, a networked configuration will be required. Larger users will have several nurses performing treatment on any patient arriving for treatment. Therefore, each nurse will require each laptop to be able to access any of the patients. The simplest approach will be to establish one laptop as the server with the other laptops operating as clients.

While we are entertaining the possibility of 10-inch screens or even PDA devices, the small resolution somewhat prohibits these implementations. However, redesign of the screen layouts may eventually facilitate these options. A clinic that desires real time collection of treatment data at each patient chair would motivate this implementation. Each device would then be part of a network with a central server.

The current backup plan uses the hard drive, preformatted CD-R/W or DVD-R/W Discs, and a USB Jump Drive. The application initiates its own daily backup to the hard drive automatically, then mirroring a daily backup to the USB Jump Drive when it is present. Backups are archived after encryption and compression to the Discs. The user should place the Jump Drive in a safe that is both fireproof and waterproof each evening and reinserted at the beginning of each workday.

A Web environment is advantageous for the implementation of the application, since this would eliminate many of the logistical issues with software updates and back up complexities. The data for each doctor is stored and backed up at the remoter server. With updates only occurring at the server, the code and the database structures would always be current.

FIG. 1 shows the Icon the user will click to start the application. This document illustrates the implementation using the 12-inch laptop implementation.

The workstation is password protected by a Windows password. A password in the System BIOS, can add further security to the application.

The user merely double clicks on the Computer Application Icon near the middle of the screen to start the application. Returning to the desktop and double clicking on the computer application icon again can start subsequent instances of the application. This would be desirable if a nurse wanted to record information for multiple patients in real time.

The laptop facilitates privacy by closing the top of the laptop between sessions. When the user reopens the laptop, Windows requires the user to enter the password. After entering the password, the desktop reappears with the set of application windows that were present when the user closed the laptop.

Figure 2:
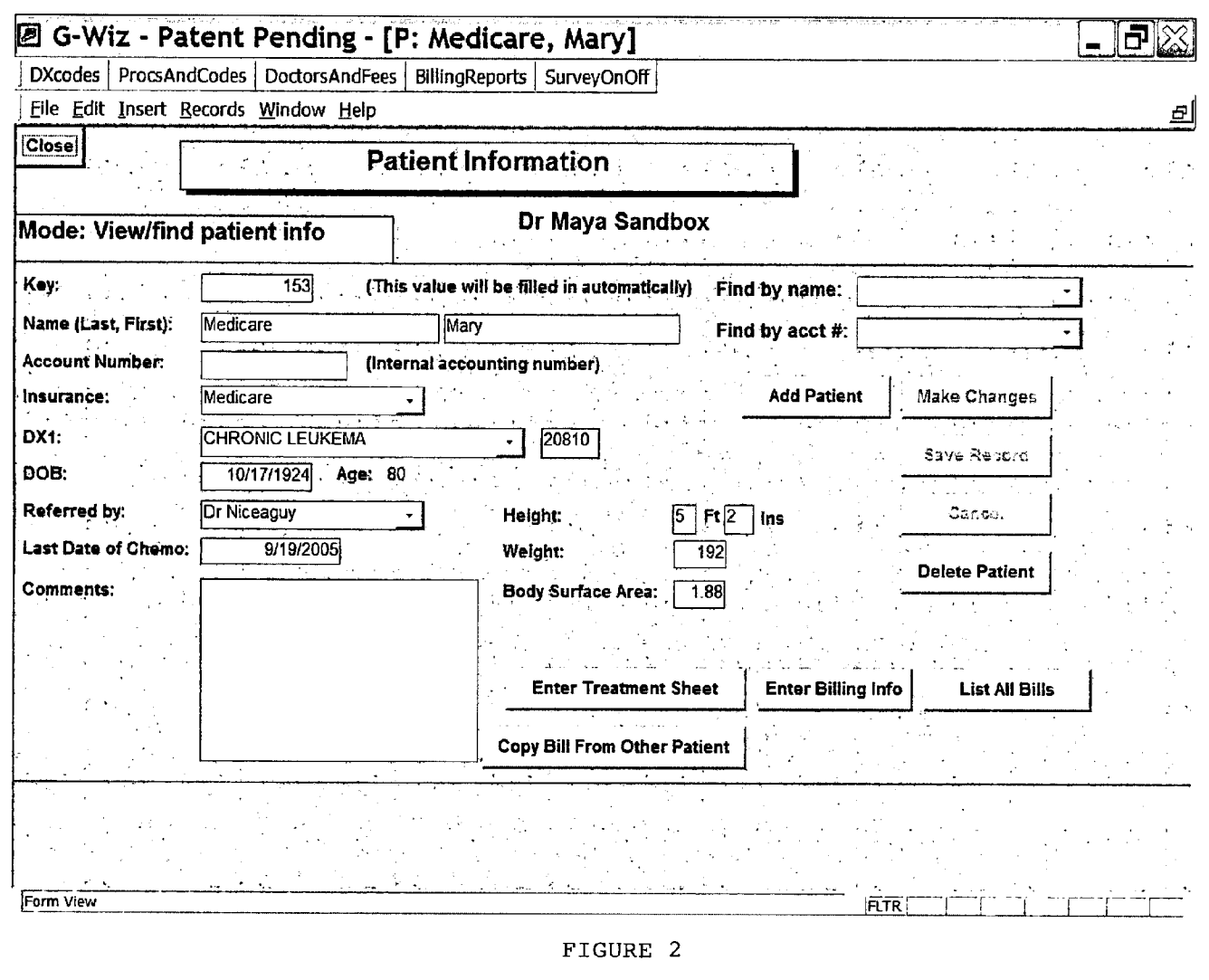

FIG. 2 is a screenshot of a Patient Information Window. This is the first window presented to the user, typically a chemotherapy nurse. It serves as the "Main Menu" for the application. At the top are buttons to maintain the supporting tables of the application: DXcodes; ProcsAndCodes; DoctorsAndFees; and BillingReports. The contents of these tables will become evident during the explanation of the main functions of the application.

Also, at the top is: SurveyOnOff. If there is a practice that does not want to bill for the Medicare Demonstration Project, this button allows the billing feature to be turned off. The button, BillingReport, leads to report functions of the application. In DoctorsAndFees, the user can enter or edit the Doctor Name and/or the Practice Name. The fee schedule for the practice is also loaded and updated here.

Find by name: allows the user to select a patient already in the application's database. The user Left clicks on Find by name: resulting in a drop down list of patients that exist in the database. The drop down list presents: Patient Last Name; Patient First Name; and Date of Birth. The user can scroll down and select the patient name or type the beginning letters of the last name. The application will present the first patient that matches the character string entered. When the desired patient is located, the application fills the fields to the left with the database contents for this patient.

An alternate selection method is available with Find by acct #: This allows the user to select a patient by the patient's account number that is used by the doctor's internal record keeping system; most likely the office's medical billing system. We have also found that some practices like to use this field to store the Social Security Number of the patient. Find by acct #: presents a drop down list with type ahead searching similar to that of Find by name:

After the user selects a patient, clicking on the Make Changes button allows modifications to the patient fields. There is also a button to Delete Patient. If the patient does not exist in the database, the Add Patient allows the user to enter a new patient.

When adding a patient to the database, the following fields are relevant:
1. Key is for internal use only by the application.
2. Patient Last Name and First Name are required.
3. Account Number is optional.
4. Insurance is required. A drop down box allows the user to select either:
    a. Blue Care Network.
    b. Blue Cross.
    c. Medicaid.
    d. Medicare.
    e. PPOM.
    f. Other.

g. Unknown. If Unknown is selected, the claims are not be generated because the application does not know what rules to apply. Unknown only serves as a 'place holder' allowing the entry of treatment data, while awaiting the correct insurance entry.

h. County Health Plan. These are patients with a 'promise' of obtaining Medicaid. Since, Medicaid is the anticipated insurance, Medicaid reimbursement rules are applied. The application suggests that the practice assign this insurance to these patients, so that a practice knows how exposed they are when Medicaid coverage is delayed. If the patient obtains Medicaid insurance, the practice should update the field to Medicaid.

5. DX1 is the Primary Diagnosis for the Patient. The user selects from a drop down list containing an alphabetical sequence of Diagnosis Codes and Descriptions defined by the user. Upon selection of a particular Diagnosis, the application displays the accompanying Diagnosis Code in the adjacent field to the right. If the Diagnosis is not in the list, the user can define a new Diagnosis Code with a Description "on the fly". Currently, the application uses the ICD-9-CM Codes, but will use the new international ICD-10 Codes, when they become required.

6. DOB is optional. This field differentiates patients that have the same name (e.g. Robert Smith). In order to abbreviate the amount of patient data that the user enters, the application does not require Social Security Number, which is the normal method to uniquely identify patients. The application calculates the patient's age, which it displays to the right to assist in identifying the patient. The computer application also includes a photographic image of the patient (not shown).

7. Referred by is optional.

8. Last Date of Chemo is sometimes required in the Remarks section of a claim; Chemo Follow Up Visits to Blue Cross being one example. The application automatically generates and updates this field. However, the biller can enter an initial value if this is an existing patient to the practice, but new to the application.

9. Comments for the patient are optional. Typically, this would pertain to insurance or billing information.

10. Height and Weight, when provided, allow the application to perform the Dubois and Dubois Body Surface Area (BSA) calculation.

Clicking the Save Record button commits these fields into the database. The Cancel button allows the user to abort any changes made or the addition of a new patient. The application presents both of these buttons during Add Patient and Make Changes.

After the user has added or selected a patient, they may proceed by clicking on Enter Treatment Sheet or Enter Billing Info. Both of these buttons proceed to allow the entry of treatment data for a particular Date of Service.

Enter Billing Info is oriented for billers working from a conventional paper superbill. A typical superbill lists various drug and administration codes under different sections of a preprinted form. The application provides a series of input screens as tabs attempting to match the most common layouts for superbills. Hence, a biller can tab quickly to Survey, Fluids, Non-Chemo, Chemo, or Office Visits/Labs/Misc. The application sequences the drugs in the drop down boxes by J-Codes, which billers are intimately familiar with, allowing the biller to quickly reach the drug they are looking for. Upon completion of input, the generated Superbill is directly viewable.

Enter Treatment Sheet is oriented for nurses. Instead of Fluids, Non-Chemo, and Chemo tabs, there is one Treatment Sheet tab. Within this tab, the nurse enters the services performed. Since, the application lists them in the Patient Treatment Sheet in the order of entry by the nurse, reporting the services in the actual administration sequence is preferred. Upon completion of input, a Treatment Sheet is directly viewable.

Nurses will typically enter data by way of the Enter Treatment Sheet button. Billers or Billing Agencies that use the standard paper superbills would enter data by way of the Enter Billing Info button.

List All Bills provides a list of patient encounters from which the user can view saved patient encounters for editing and printing purpose. In addition, it allows the user to copy a patient encounter to another Date of Service.

Copy Bill From Other Patient provides the ability to copy encounter data from one patient to another.

Figure 3:
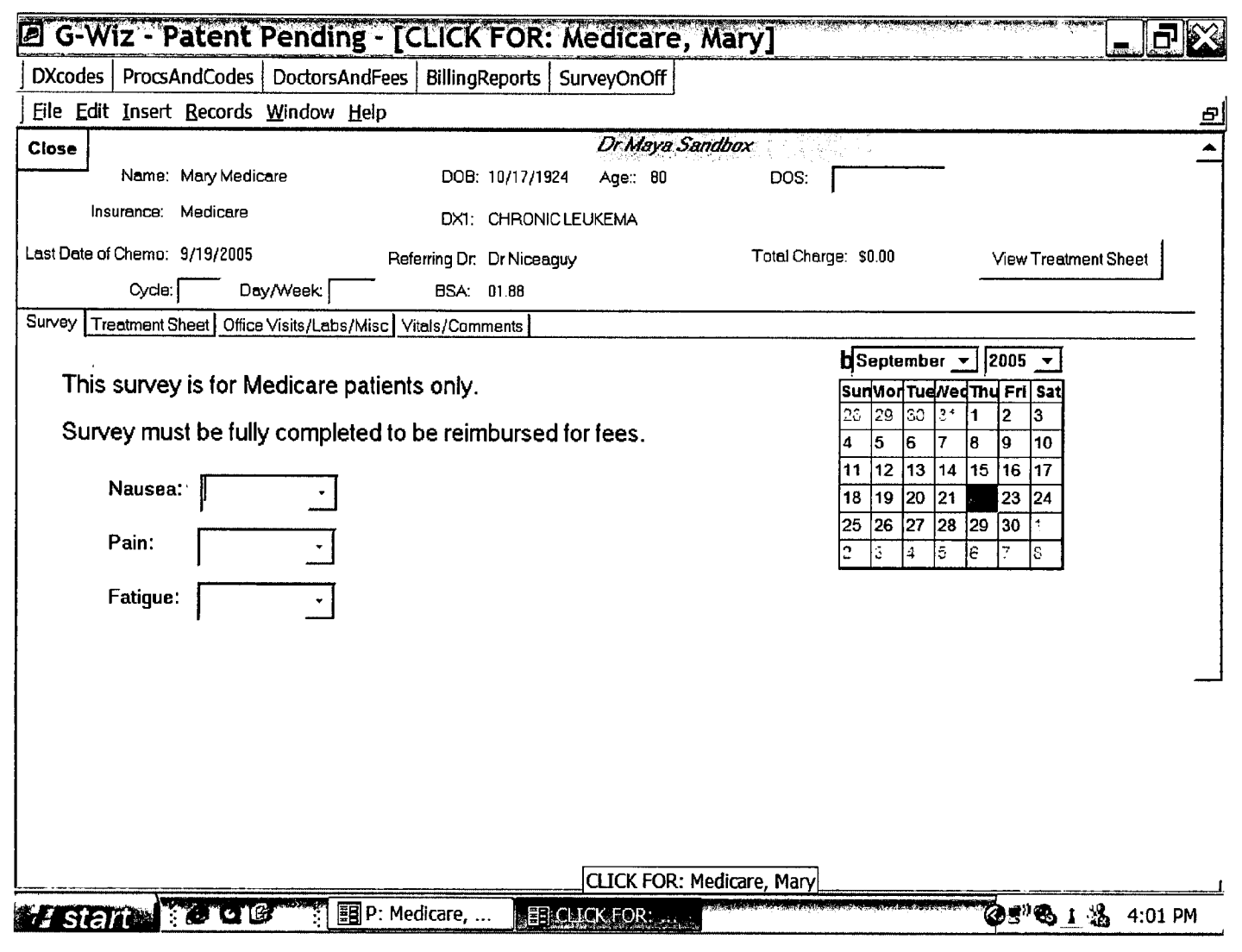

FIG. 3 is a screenshot illustrating the start of data entry for a Medicare patient. This window resulted from clicking on Enter Treatment Sheet from the Patient Information Window. The window has the text, 'CLICK FOR: [patient name]', in order to locate it on the Windows Task Bar at the bottom of the screen. As mentioned previously, the application has the capability to allow entry of patient treatment data in real time. To accommodate multiple patients in real time, users can start subsequent instances of the application. Each patient's window is readily located on the Windows Task Bar and clicked when it is time to enter real time data for a particular patient.

The top portion of the window repeats some of the identifying characteristics of the patient from the previous window. The application displays the patient's age to assist in identifying the patient. The computer application also accommodates a photographic image of the patient for further identification (not shown).

The bottom left of the upper section of the screen allows for Cycle-Day/Week entries, as optional input from the nurse. If the nurse recorded chemotherapy data, but did not enter Cycle-Day/Week, the application will issue a prompt, encouraging their entry, which the nurse may decline. The application prevents the entry of duplicate Cycle-Day/Week values for a patient. If the nurse entered values for these fields and there was no chemotherapy performed, the application will reject the values, as Cycle-Day/Week only applies to chemotherapy.

The application displays a calendar to the right of the window. The application does not allow the entry of future dates. The application highlights tomorrow's date to force the nurse to overtly select a date. Although the application can participate in a real time environment, where there is an advantage to default to the current day, most of the nurses seem to be using the application after the treatment has concluded. It is typical for the nurses in many practices to do their charting at the end of the week, increasing the likelihood for incorrect date entries. Hence, the application forces the nurse to select the Date of Service (DOS) on every encounter. If the nurse has not entered a date and clicks View Treatment Sheet, the application will issue a message stating, "You must enter a Date of Service".

After the user clicks the DOS, the application displays the DOS field at the top right of the window in mm/dd/yyyy format. Clicking on the date causes the calendar to reappear, which allows the date to be changed. If the DOS already exists in the database, the application issues: This patient already has a bill for this DOS will appear after clicking View Treatment Sheet.

The content of the upper portion of the window remains fixed throughout the selection of the various tabs. The user can change the contents of the modifiable fields (DOS and Cycle Day/Week) at any time.

The remainder of the window consists of a series of tabs containing logical groupings for patient treatment data. This window opened at the Survey Tab because Mary Medicare has Medicare insurance and the doctor's practice has elected to participate in the Medicare Demonstration Project. The nurse may enter the Survey answers at this point or click on one of the other tabs and return to this tab later. There is no required order for entry of any of the tabs and the entries do not have to be complete because the nurse can always return to a tab making additions, deletions, or changes to the data. The application is persistent in its quest to maximize reimbursements. If the nurse had forgotten to return to the Survey, the application will remind the nurse that the Survey is incomplete and force the nurse to return to the tab and complete the answers.

Figure 4:
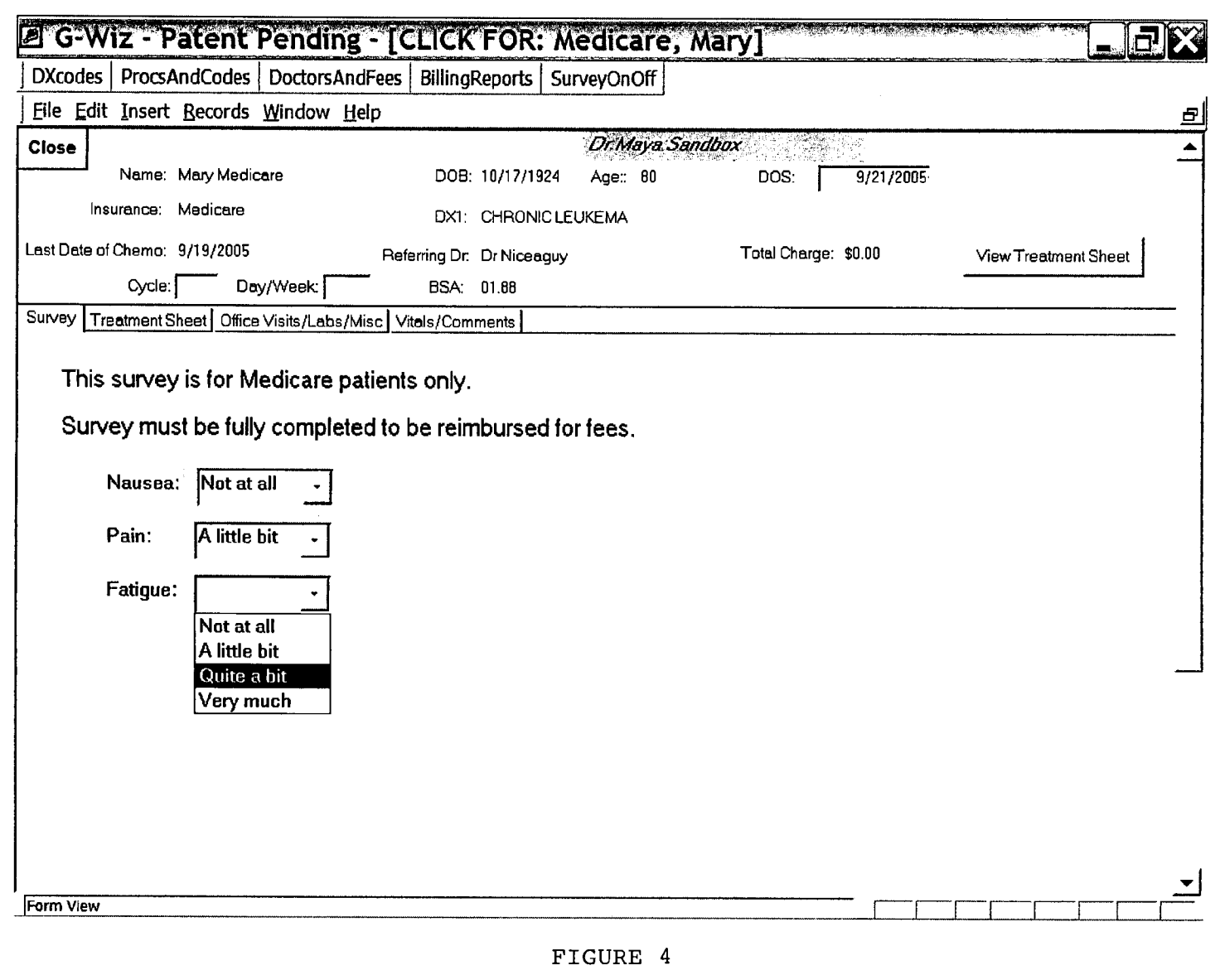

FIG. 4 is a screenshot of the Survey tab. Here you can see that the nurse selected a DOS of Sep. 21, 2005, since it appears to the right of DOS in the upper right corner of the window and the Calendar has disappeared. To change the date, the user clicks the DOS causing the Calendar to reappear.

At this point, the nurse may select the appropriate survey answers by selecting from the drop down box for each Survey question. The application checks to verify that there are answers to all three questions after the nurse clicks the View Treatment Sheet button. If the nurse did not answer all three questions, the application presents the Survey tab, instructing the nurse to complete the Survey. If for some reason, the nurse desires to waive the Survey, the nurse may deactivate the Survey by clicking on SurveyOnOff at the top of the window. Clicking SurveyOnOff a second time reactivates the Survey.

Figure 5:
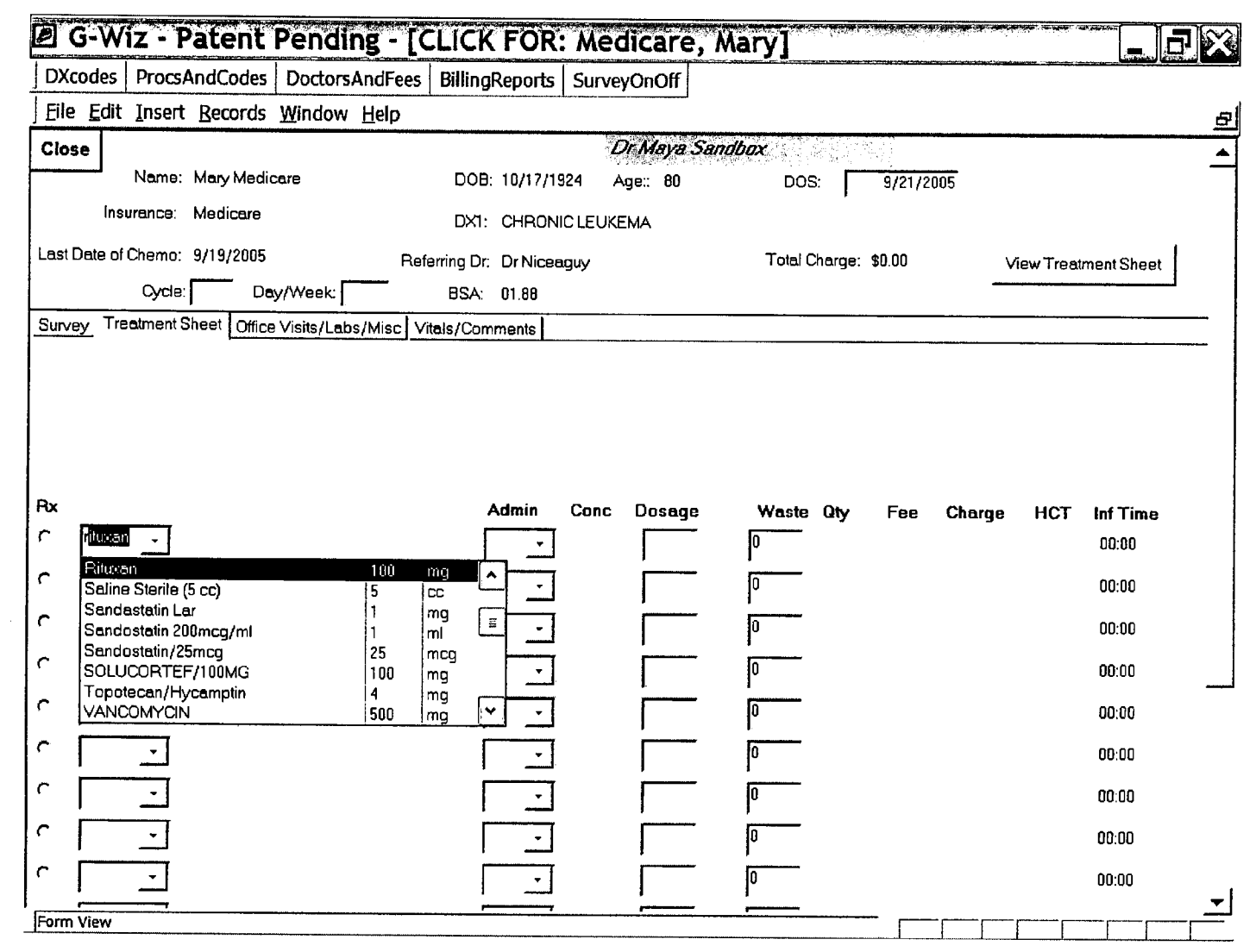

FIG. 5 illustrates entry of treatment data when selecting a drug or fluid. Here the nurse has selected the Treatment Sheet tab. At the left, the nurse can select from the drugs and fluids, predefined in ProcsAndCodes. Because they appear in alphabetic sequence by Drug Description, the drugs should be given names familiar to the nurse. In this case, entering the letter r, positioned the drop down to the first entry beginning with r, Rituxan.

Figure 6:
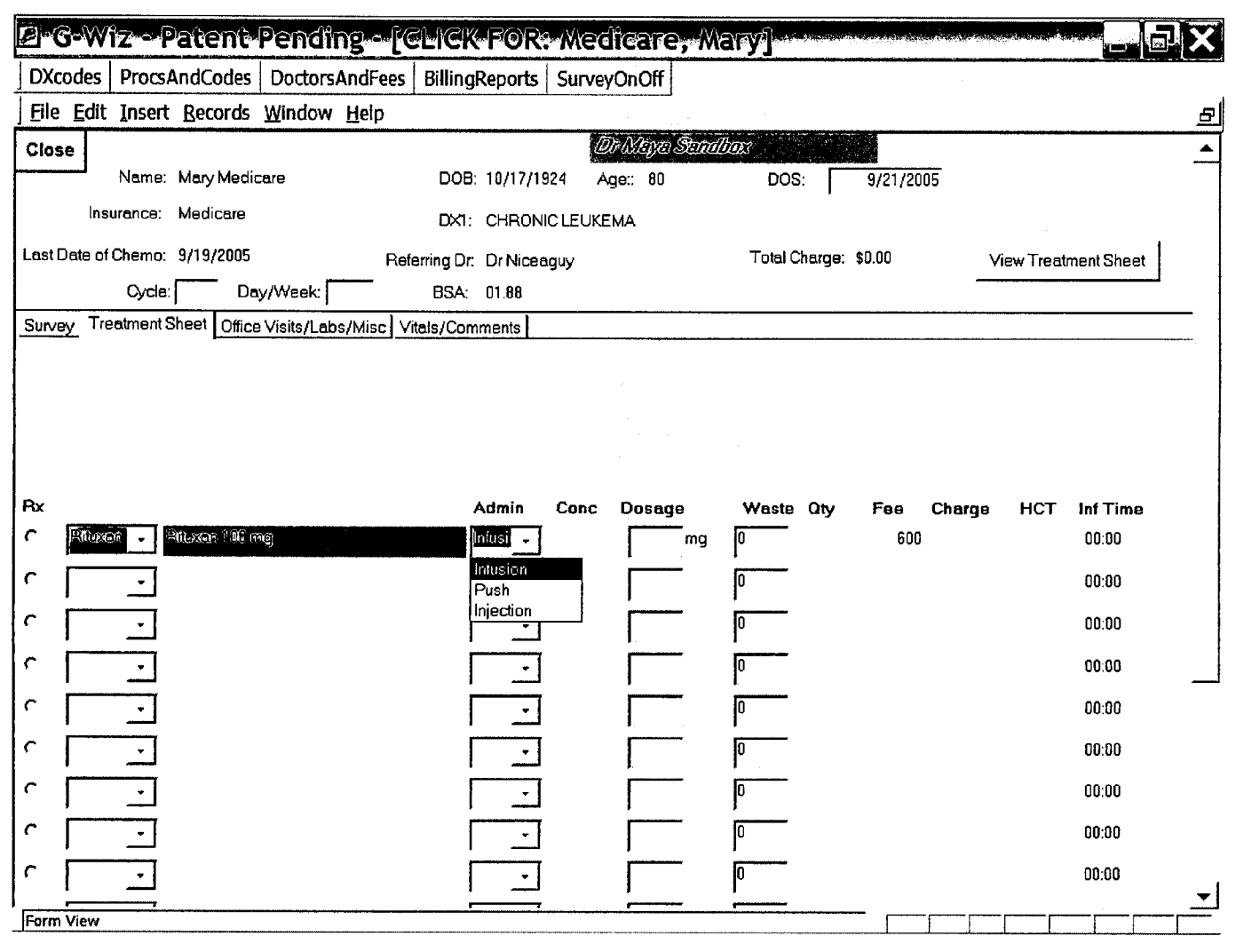

FIG. 6 illustrates entry of treatment data when selecting an administration. The patient is to receive Rituxan by Infusion. The drop down box shows the default Admin choices available for a drug. These choices can be limited per drug by settings in ProcsAndCodes. Some Drugs can only be administered by: (Push or Pump only); (Injection or Infusion only); (Injection only); (Push or Infusion only); (Push only); or (Infusion only). The default is (Infusion or Push or Injection).

Figure 7:
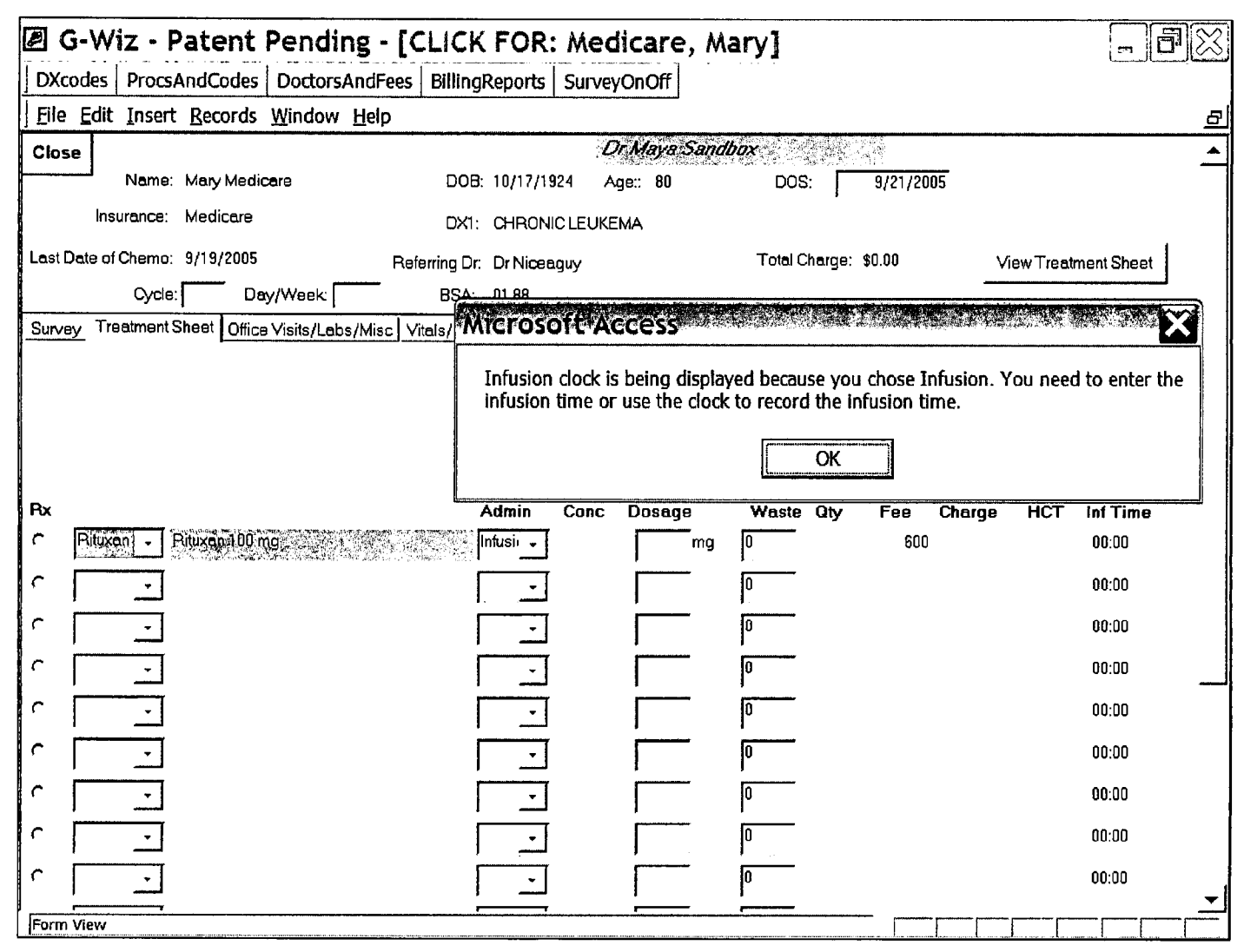

FIG. 7 illustrates entry of treatment data when selecting an infusion. Because the nurse selected Infusion, this prompt appears. The application is about to display an Infusion Clock for the nurse to establish the Infusion Time. The nurse proceeds by clicking on OK.

Figure 8:
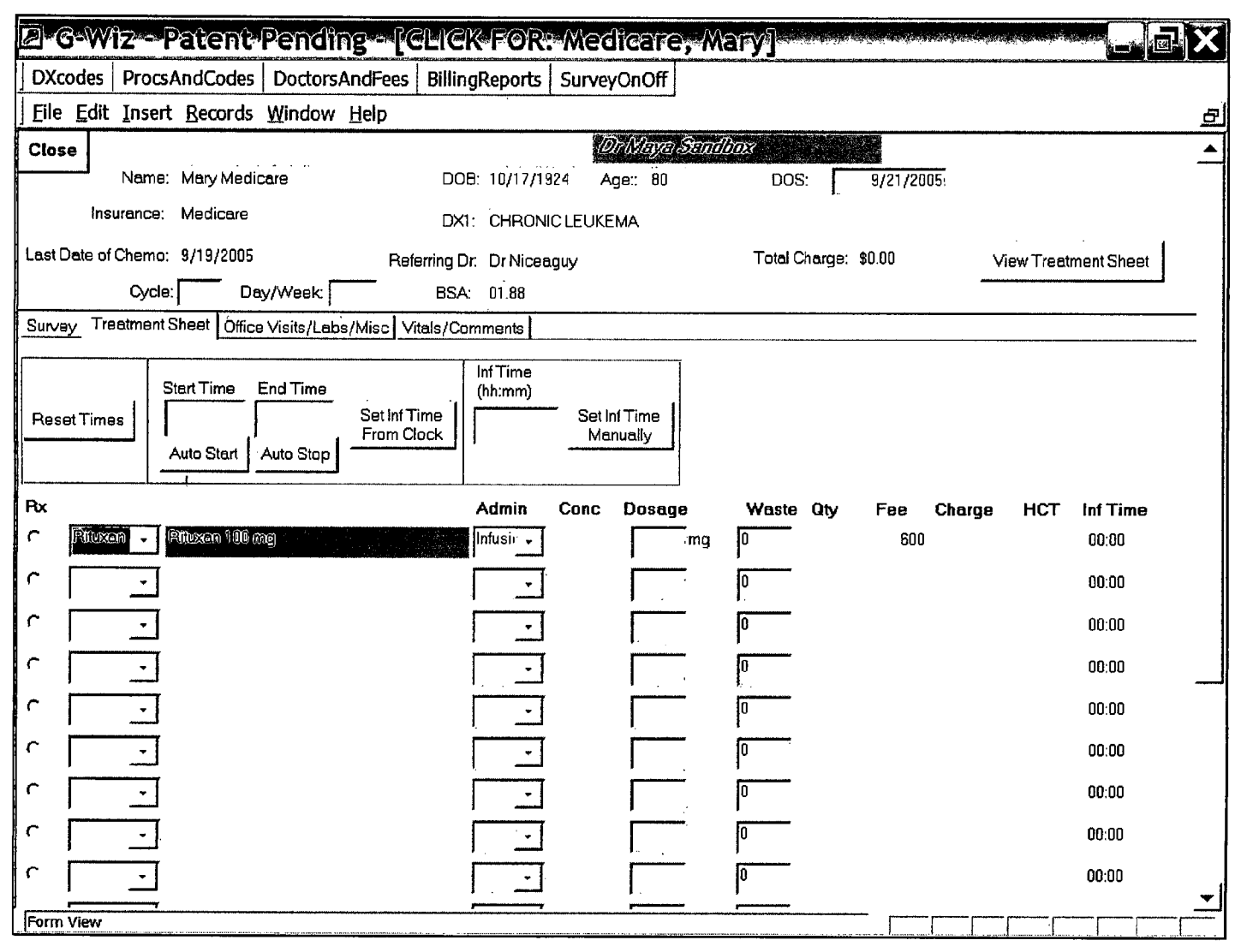

FIG. 8 shows a treatment screen with an Infusion Clock. The nurse has clicked the OK button, which displays the Infusion Clock. The nurse can click on Auto Start to start a stopwatch for real time recording of the infusion. When the infusion is completed, the nurse would click on Auto Stop. Then when the user clicks Set Inf Time From Clock, the elapsed time is calculated and recorded as the Inf Time for the Infusion.

As an alternative, the nurse can enter the Start Time and End Time in Military Time as log entries. Again, when the nurse clicks Set Inf Time From Clock, the elapsed time is calculated and recorded as the Inf Time for the Infusion.

The third alternative is for the nurse to enter Inf Time as hh:mm and Click on Set Inf Time Manually, resulting in hh:mm as the Inf Time for the Infusion.

Figure 9:
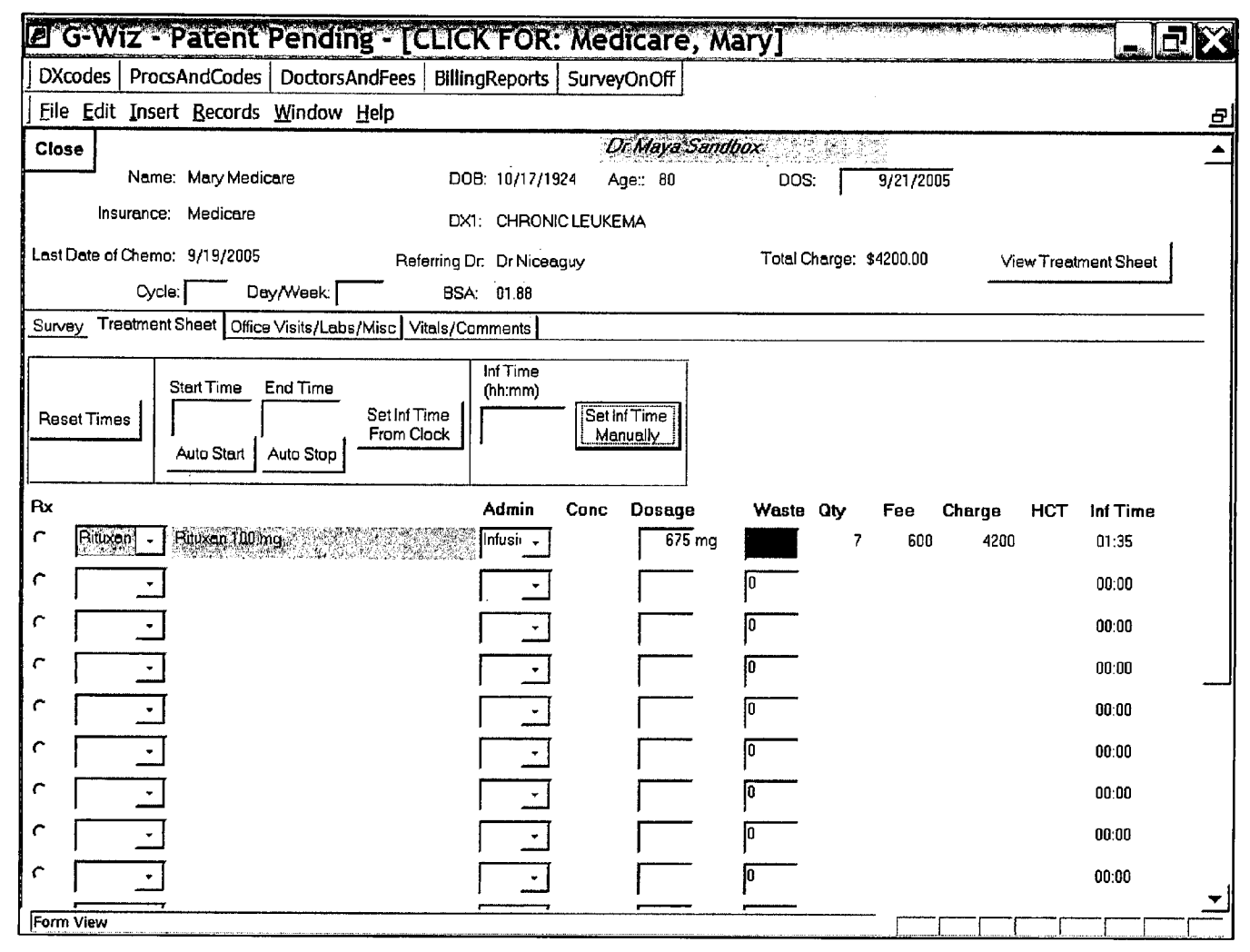

FIG. 9 shows a treatment screen with an Infusion Clock and waste for a Single Use Vial drug. The nurse has entered 1:35 in Inf Time (hh:mm) and clicked on Set Inf Time Manually. The application assigns the time of 01:35 to the Infusion for Rituxan, since it is the highlighted drug. The application transfers the 01:35 to the Rituxan line in the column Inf Time. The application clears the 01:35 in the Inf Time (hh:mm) box to accommodate the next Infusion or Hydration time entry.

Had the nurse entered 1:30, the application would have notified the nurse: Rounding Down additional hour of Infusion Time because Time is 1:30. Infusion time of 1:31 would Round Up. Rounding Down will be done for billing purpose only. The time you enter is still recorded as is. Confirm the Infusion Time is actual and accurate.

Rituxan comes in 100 mg and 500 mg Single Use Vials. The nurse cannot use any remaining portion on another patient or encounter. The remainder is reimbursable when included in the billing quantity. Both vial sizes have the same J-Code (J9310) with a HCPS Billing Unit of 100 mg. The application estimates the Waste by presuming the vial size is the same as the HCPS Billing Unit. In this case, the application has estimated seven vials to provide 675 mg, leaving 25 mg as Waste. Therefore, the total amount of drug expended is 700 mg. When dividing by the HCPS Billing Units of 100 mg, the billing algorithm determines a HCPS Billing Quantity of seven. The Fee Amount in DoctorsAndFees is $600 per HCPS Unit yielding a Charge of $4200.00. The application highlights the estimated Waste in red to catch the nurse's attention in case the nurse needs to modify the amount of waste.

However, if the vial size were actually 500, the Waste would be 325 mg, yielding a Charge of $6,000.00, a significant difference in reimbursement, illustrating how important it is for the nurse to monitor this field. To improve the estimate of Waste, the program application also provides the ability to select the drug by vial size.

At this point, you can see the Total Charge is $4200.00, as displayed in the upper right portion of the window. However, this does not include the administration fees because parsing of the applicable Medicare G-Codes has not taken place, yet. Nor should they be, because the entire encounter needs to be examined in its entirely before the Initial G-Code can be determined, which significantly affects the Total Charge.

Figure 10:
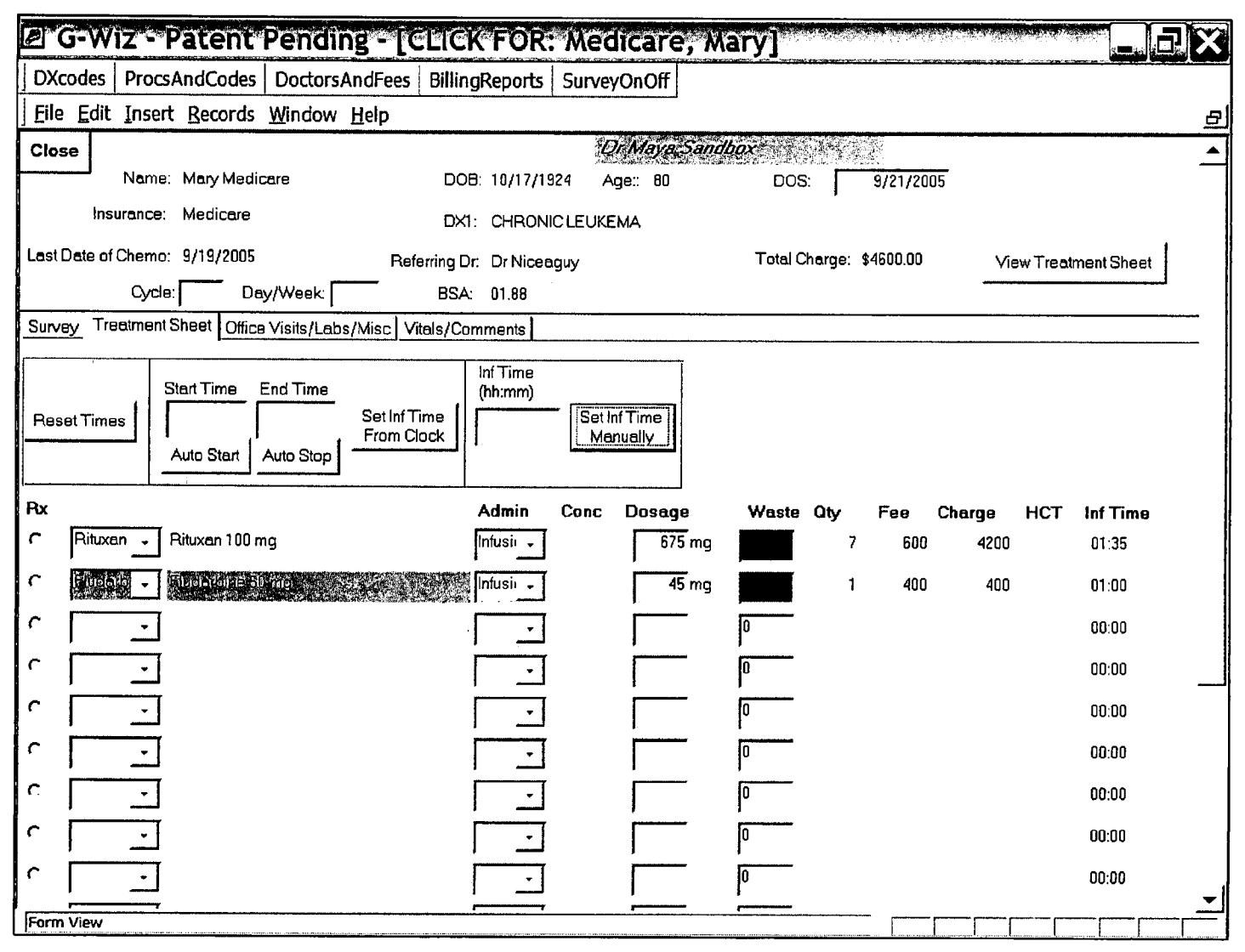

FIG. 10 shows a treatment screen with a subsequent chemotherapy drug and administration. The patent received 45 mg of Fludarbine by Infusion over a one-hour period. The nurse entered the appropriate quantity. Since the Infusion Clock was already in the window, the prompt stating: Infusion clock is being displayed . . . does not appear again. The application highlights Fludarbine after the nurse selects it. Therefore, any clock entries made will apply to this drug. If the nurse forgets to make the time entry and clicks View Treatment Sheet, the application issues an error message.

Fludarbine comes in a Single-Use Vial. There is only one vial size of 50 mg, which is equal to the HCPS Billing Unit. The application estimate of 5 mg is probably accurate, but the nurse can modify the Waste if necessary. Perhaps the nurse spilled the previous vial or the previous vial had expired and the manufacturer will not provide for an exchange.

Notice that the Fee for Fludarbine is $400.00 and Total Charge is now $4600.00. Remember Admin Fees will not be determined until the nurse clicks View Treatment Sheet.

Figure 11:
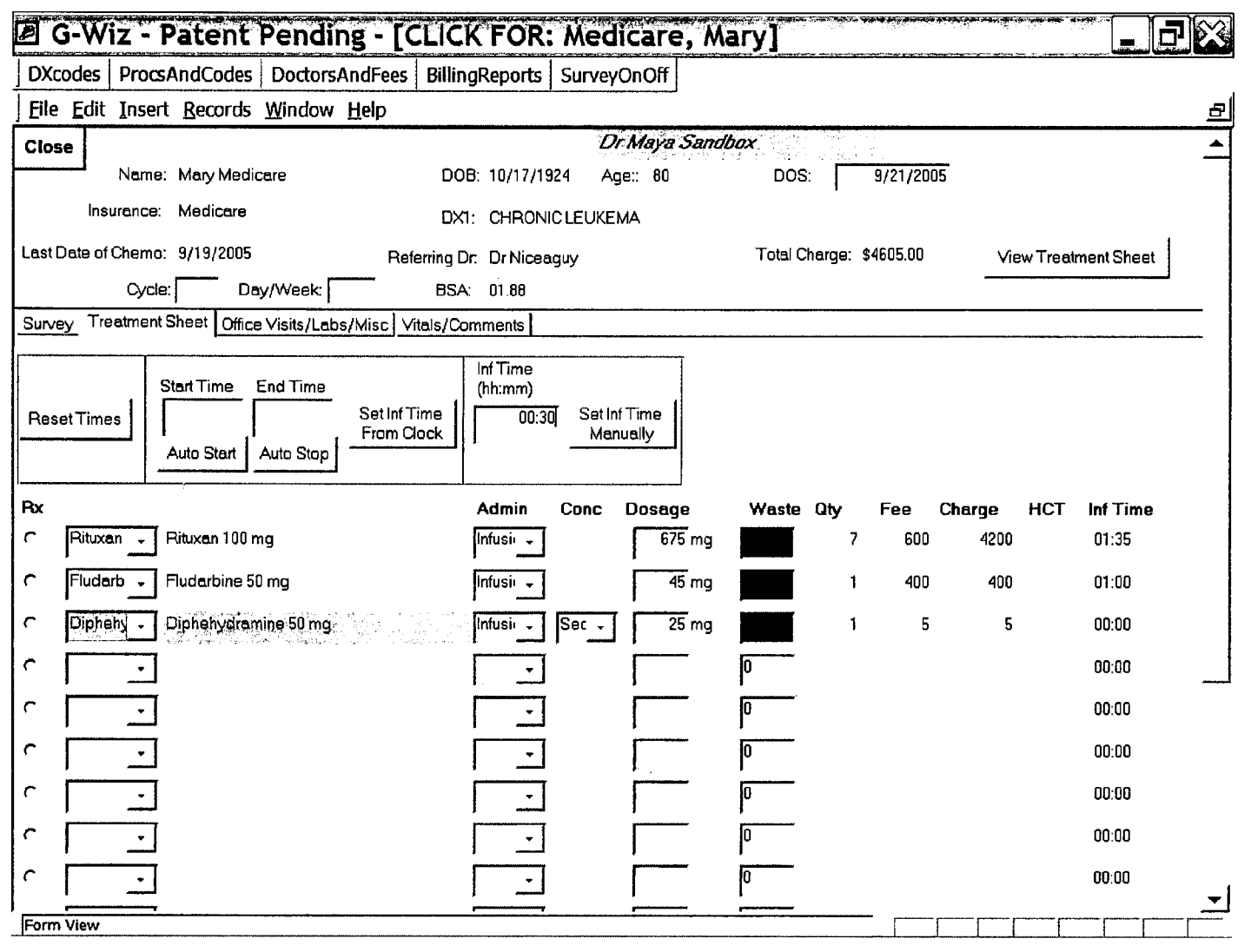

FIG. 11 shows a treatment screen with a non-chemotherapy drug and administration. The nurse reported that the patient received 25 mg of Diphehydramine by Infusion. It occurred over a 30-minute period. Hence, the nurse entered 00:30 into the Inf Time (hh:mm) box. Clicking on Set Inf Time Manually would transfer it to the Diphehydramine line.

Note: Medicare defines an Infusion Time of 15 minutes or less as a Short Infusion and requires the practice to bill it as a Push. When this is about to occur, the application will inform the nurse: Infusion times of 15 minutes or less will be billed as Pushes.

Diphehydramine comes in a Single-Use Vial. There is only one vial size of 50 mg, which is equal to the HCPS Billing Unit. Therefore, the application estimate of 25 mg is probably correct, but the nurse could modify the Waste. Notice the Total Charge increased by $5 to $4605.00.

Had the patient brought in his own drug and had it administered, the nurse would have clicked the Rx radio button, indicating that the application should not bill the J-Code representing the drug charge to Medicare. Common examples are: J1750 (Iron); Q0136 (Procrit); J3487 (Zometa); and J2505 (Neulasta).

In the column labeled Conc is a drop down list that defaults to Sequential, but the user can select Concurrent. The Medicare G-Code system requires a different administration code for a non-chemotherapy drug when it is infused simultaneously with another drug, i.e., Concurrent with any other chemotherapy or non-chemotherapy infusion. The field only appears when a non-chemotherapy Infusion is being reported. Here, the nurse has reported that the patient was administered Diphehydramine as a sequential infusion.

Figure 12:
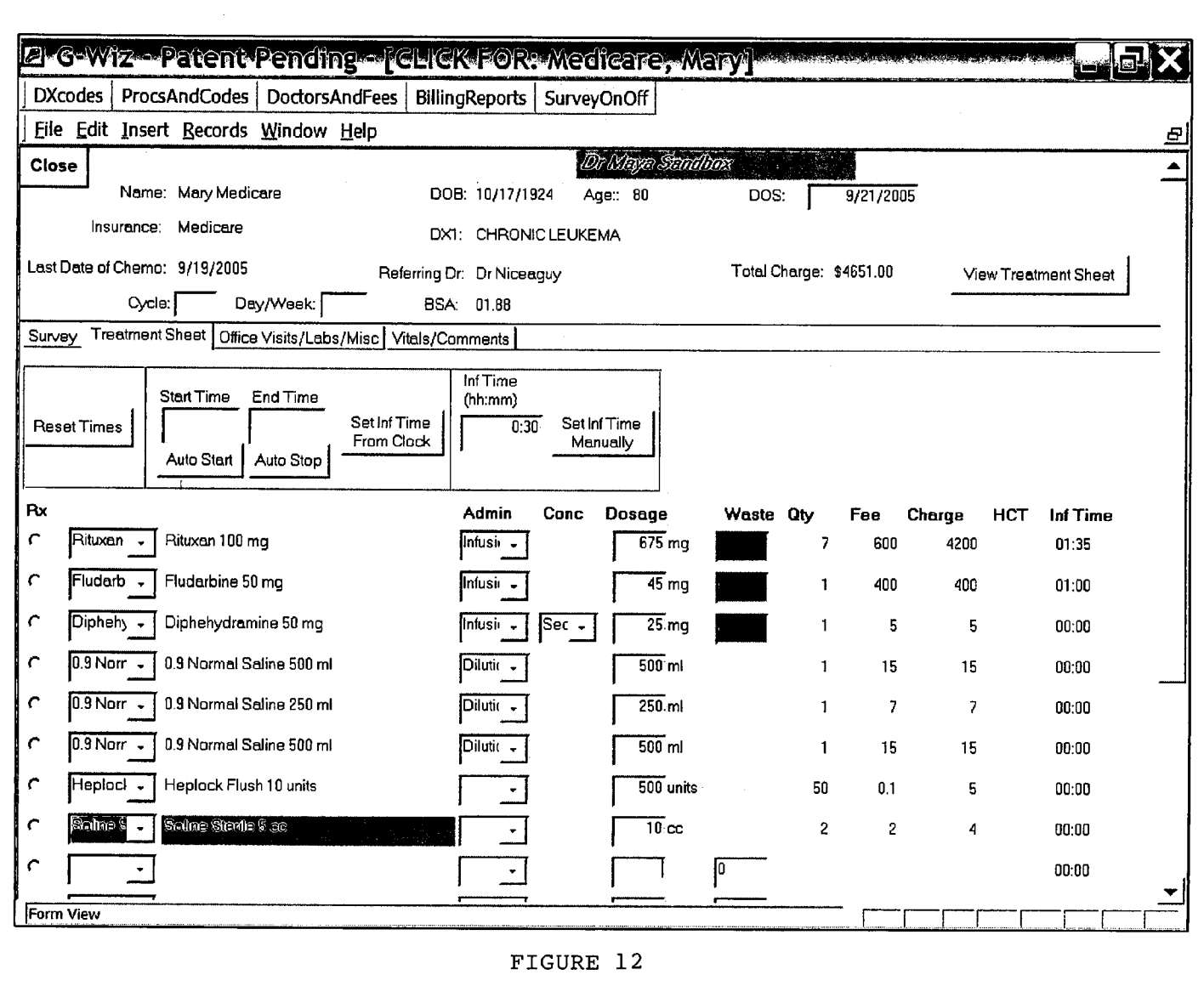

FIG. 12 is a treatment screen with fluids. The nurse reported the bags of Saline used during the chemotherapy session. The nurse administered 500 ml of Normal Saline to the patient followed by 250 ml and then another 500 ml. Both bags served as a Dilutant to the administered drugs. The application reports each bag on the Treatment Sheet in the order administered. The billing algorithm bills the two 500 ml bags as one J7040 with a quantity of two.

Dilutant is the default Admin for bags of Saline. The other value is Hydration; described in detail later. The application's billing algorithm will not generate G-Codes for the Saline because there is no reimbursement for its administration, except during Hydration. The application tallies the Fees for the Saline itself in the Charge column.

The Port was flushed with a dosage of 500 units of Heplock. Since the HCPS Quantity is in units of 10, the billable HCPS Quantity is 50. In DoctorsAndFees, the Fee to be charged was defined to be $0.10 per HCPS Quantity resulting in a line item charge of $5.

Insurance carriers do not provide reimbursement for Heplock, Heparin, or the 5 cc of Saline. These supplies are bundled. The application reports them in the patient's Treatment Sheet, but does not bill for them. The application calculates the supply fees because they once were reimbursable and might be again in the future.

The port flush administration is also bundled. It is not reimbursable, except in one very narrow circumstance. This is when a nurse performs a port flush and there are no other services for the day, except for Labs. The nurse selects the Port Flush administration in the Office Visit/Labs/Misc tab; so, there is no need to have Admin values for the port flush supply J-Codes. Hence, the Admin values for the port flush supplies are all blank, as you can see in their drop down boxes.

The computer application can determine when a port flush is reimbursable and offers G0363 (Port Flush) if the nurse has not already selected it. If the nurse has selected 99211, OV Brief (Nurse Visit) instead of Port Flush, the application offers G0363, Port Flush, in its stead.

This is the end of the Treatment Sheet entries. Although, there appears to be only one more line for data entry, there is a scroll bar to the right that can be used to access more lines on the form.

Figure 13:
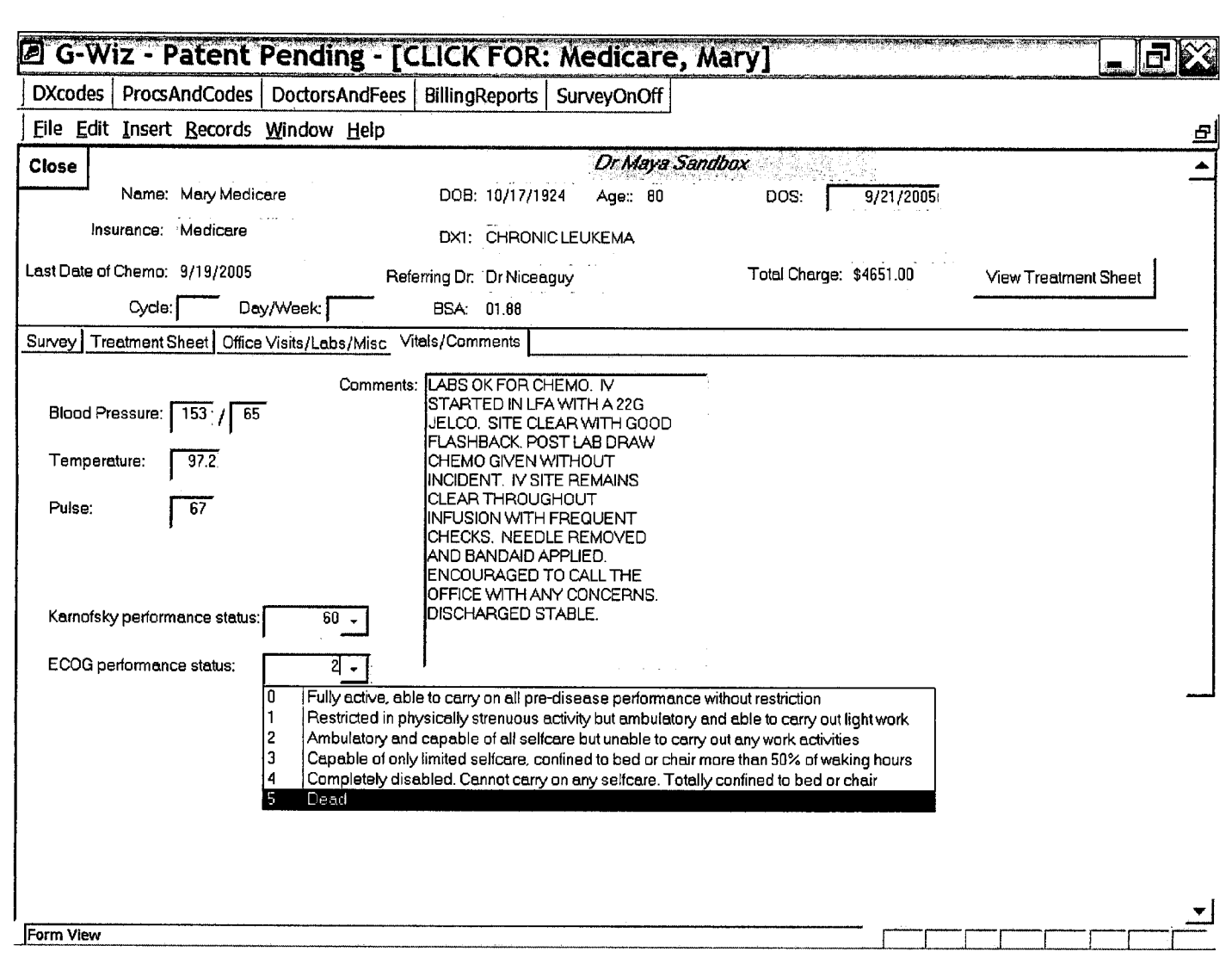

FIG. 13 illustrates the entry of Vitals/Comments. The nurse has jumped over to the Vitals/Comments tab. The nurse recorded the patients Blood Pressure, Temperature, and Pulse. The nurse also made entries for the Karnofsky and ECOG performance status. In addition, the nurse entered Progress Notes. This can be especially handy to the billing department when a carrier denies a claim and demands to see Progress Notes. There does not have to be any manual searching through patient charts. As we will see, the application can print them out in the Treatment Sheet for the patient's chart or for forwarding to the insurance carrier.

Figure 14:
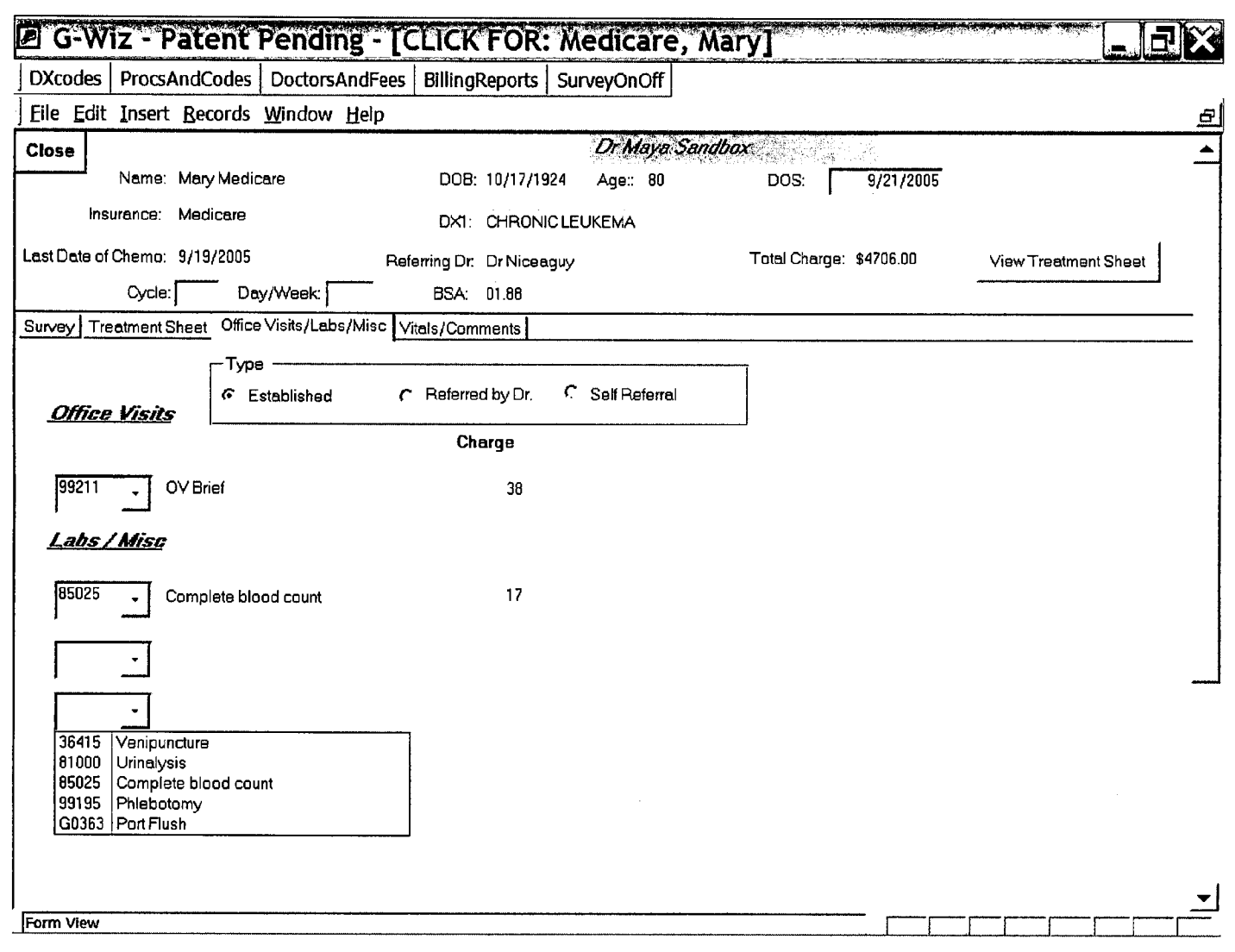

FIG. 14 illustrates the entry of Office Visits/Labs/Misc. The nurse has clicked on the Office Visits/Labs/Misc tab and selected an OV Brief (99211). The nurse is also reporting a Complete blood count. You can see all of the choices for Labs/Misc near the bottom of the form. Total Charge now appears as $4706.00. Since this seems to complete the patient encounter, the nurse clicks on View Treatment Sheet.

Figure 15:
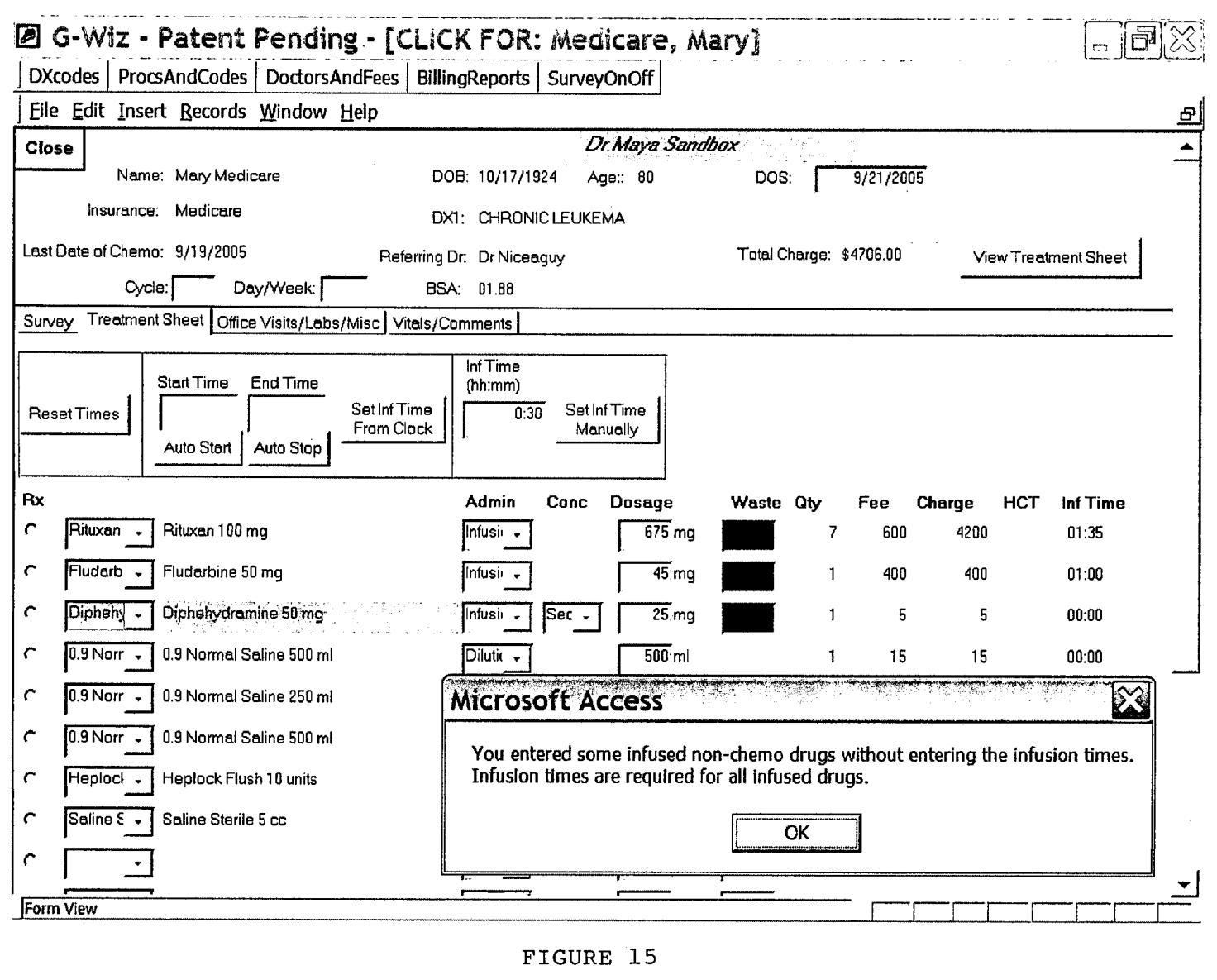

FIG. 15 shows a treatment screen with missing infusion time. The nurse forgot to click Set Inf Time Manually after entering the 30 minutes for the Infusion of Diphehydramine. The application discovered this, issuing the prompt and highlighting Diphehydramine for correction. The nurse clicks OK and then clicks on Set Inf Time Manually to transfer the 30 minutes from the clock to the Infusion time for Diphehydramine. The nurse proceeds by clicking on View Treatment Sheet.

Figure 16:
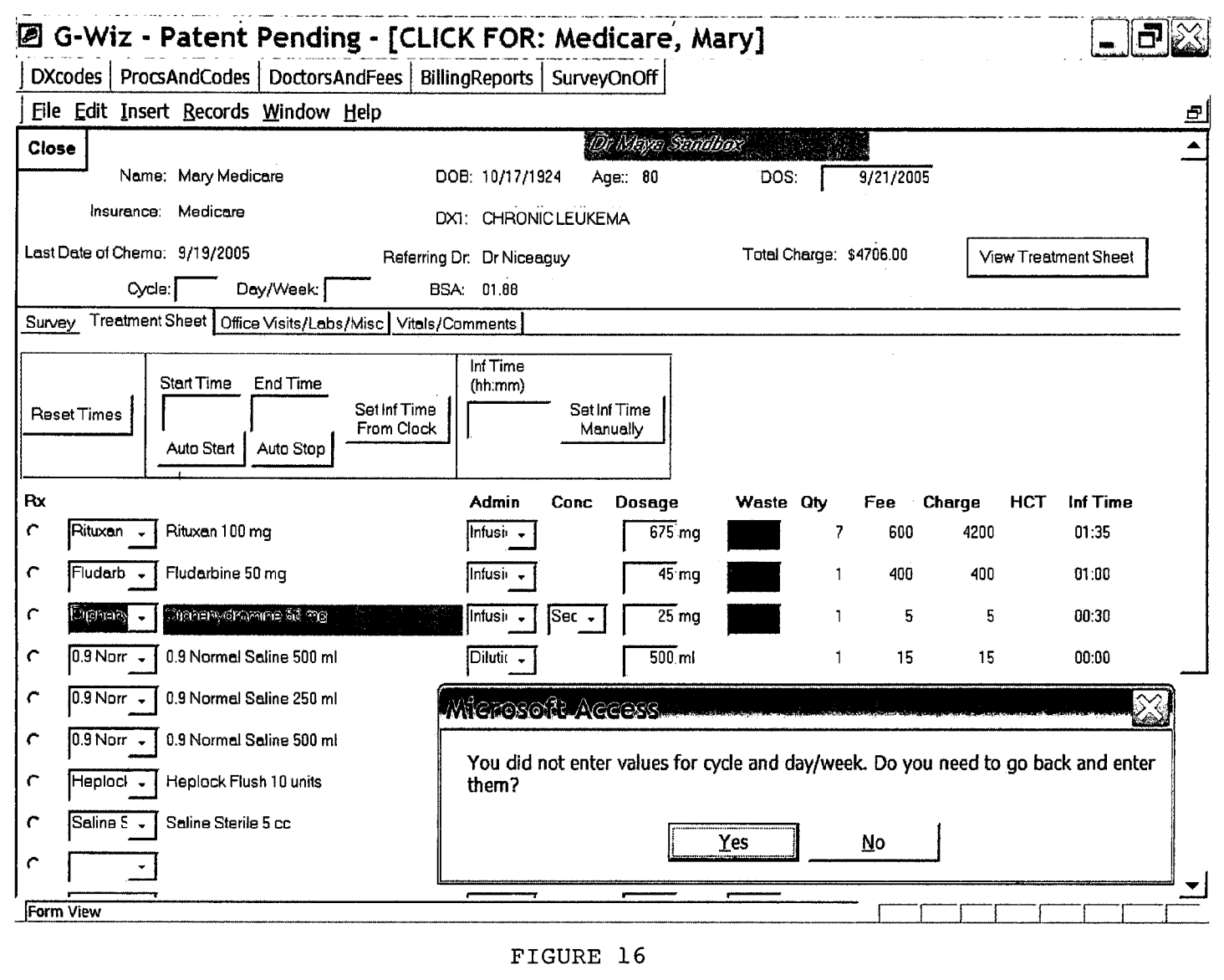

FIG. 16 shows a prompt noting missing Cycle-Day/Week values. The application suggests the recording of the Cycle and Day/Week. This is probably a good idea because the nurse can add it to the patient's chart by printing the Treatment Sheet that the application is about to produce. In addition, the application displays a list of Superbills with the included Cycle-Day/Week entries. Any omissions in the series could mean a Superbill is missing. Perhaps an encounter was misplaced and not entered into the application. The nurse enters the Cycle and Day and clicks on OK.

Figure 17:
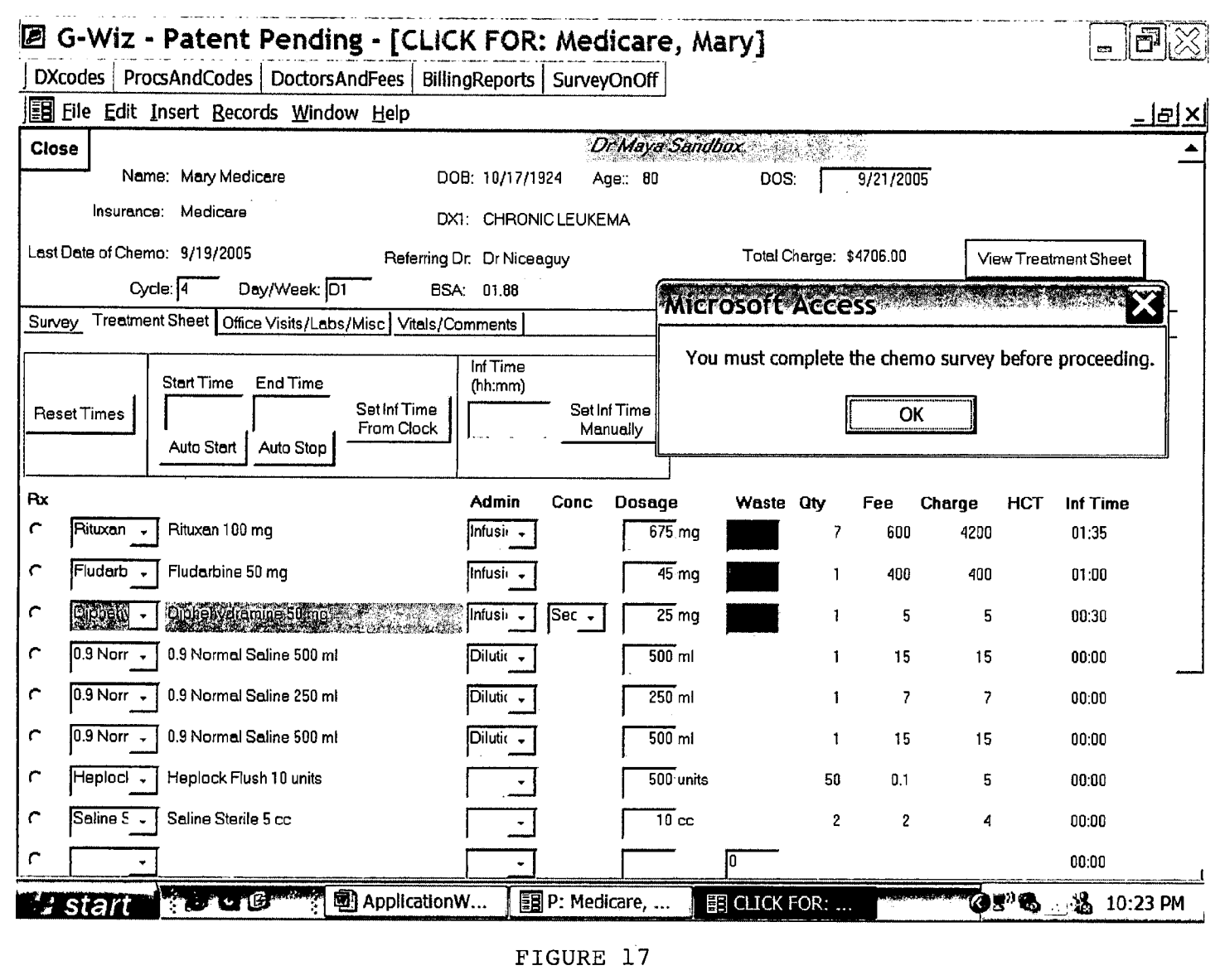

FIG. 17 shows a prompt forcing the user to enter missing Survey questions. The application has detected that the doctor's practice has decided to participate in the Medicare Demonstration Project, but apparently, the nurse did not answer all of the Survey Questions. Had the patient not received a Chemotherapy Infusion or Chemotherapy Push, the application would not have issued this prompt because the Demonstration Project only reimburses in those instances. In addition, the patient must have a cancer as a primary diagnosis. The nurse clicks the OK.

Figure 18:
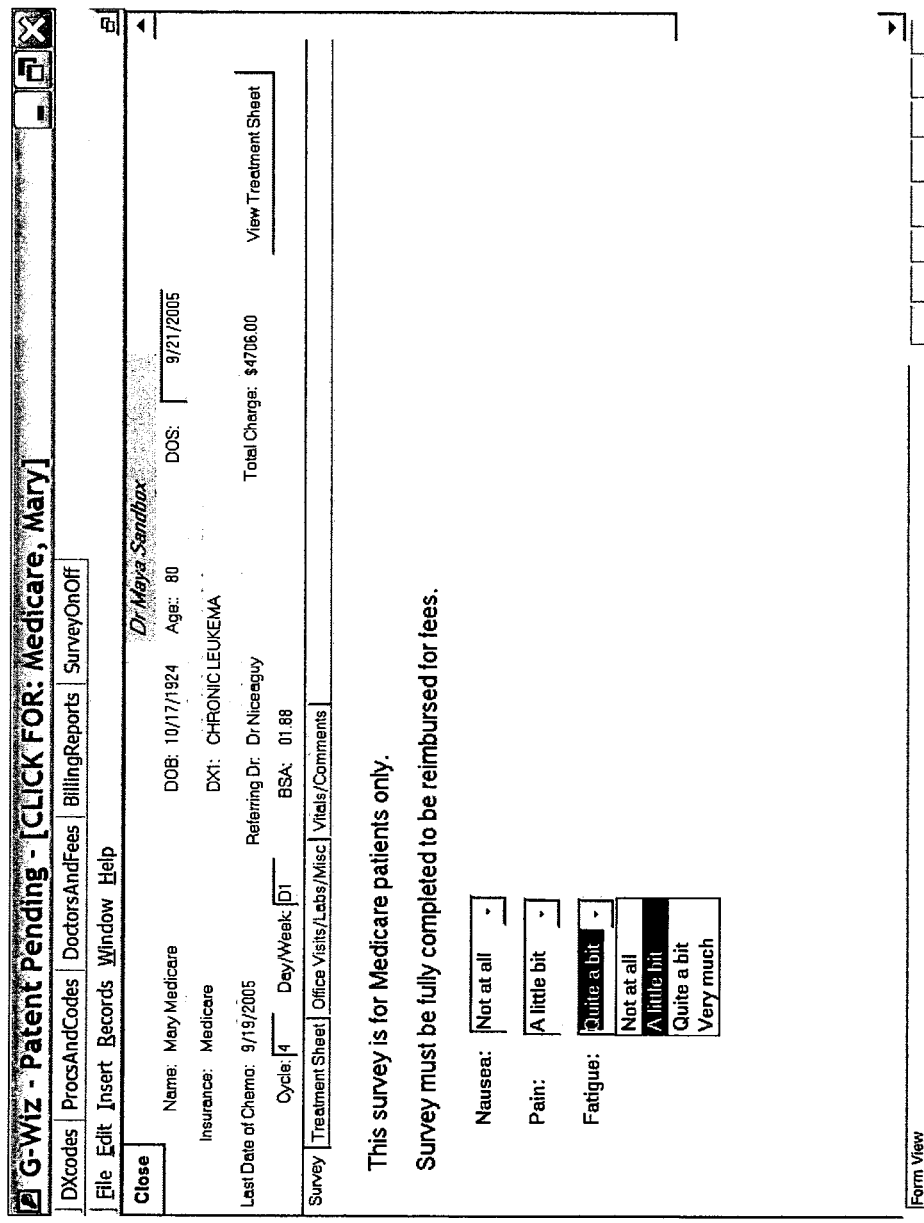

FIG. 18 illustrates that the application presented the Survey Tab to the user in order to complete the Survey questions. The nurse forgot to answer the question regarding Fatigue. All three questions must have answers in order to receive any reimbursement; so, the nurse enters Quite a bit and clicks on View Treatment Sheet.

Figure 19:
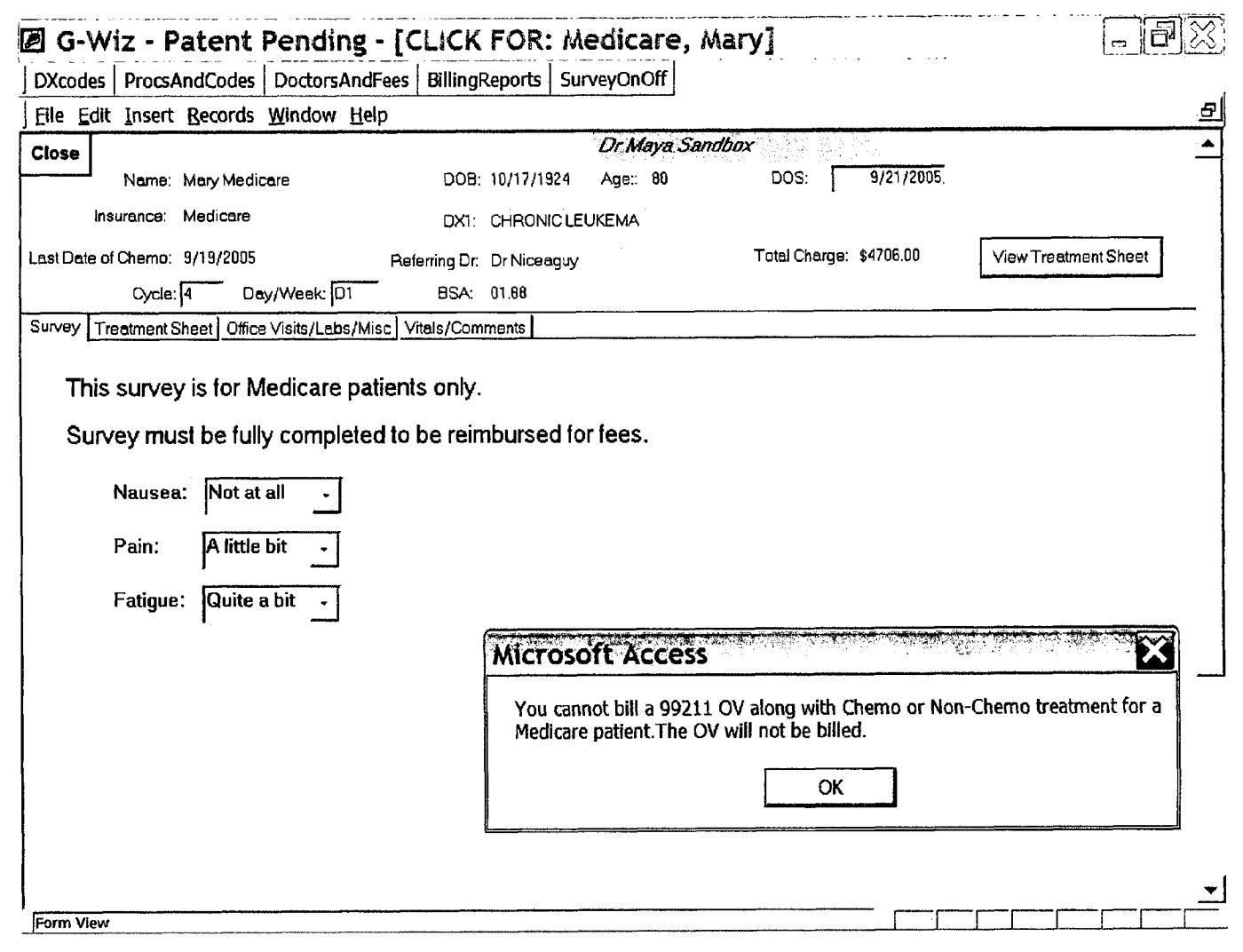

FIG. 19 shows the blocking of a 99211 charge for a Medicare patient. This prompt appeared because Medicare does not pay for a 99211 if there is chemotherapy or non-chemotherapy on the same DOS. This will result in a rejection message in the Explanation of Benefits. One of the objectives of this application is to minimize the number of rejections, especially those that are innocuous. The application seeks to reduce the deluge of messages in the EOBs in order not to lose sight of rejections, requiring prompt follow up. Even if by chance Medicare makes payment on the charge, it is only a matter of time before Medicare discovers the mistake and seeks to reclaim the money. This will be by deducting the error from a future claim, causing confusion for the billing department and end up costing more in the long run. Probably the most negative aspect is that they will overstate the Accounts Receivables, falsely indicating revenue that is not there.

Note: Medicare only denies payment for 99211 Level I (Nurse) Office Visit Brief. Medicare allows Higher-level Office Visits when billed with a 25 Modifier.

After clicking on OK, another prompt appears.

Figure 20:
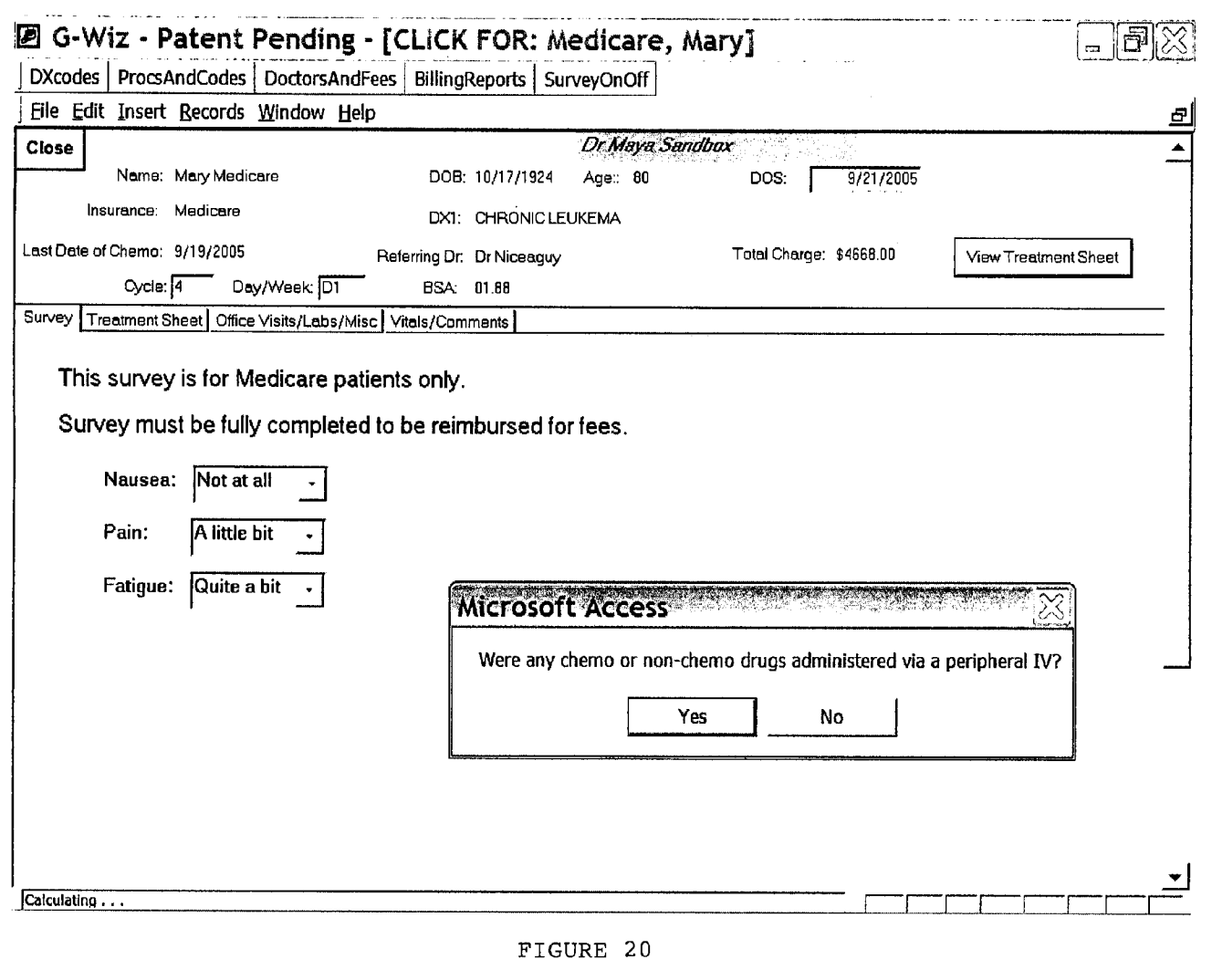

FIG. 20 shows a prompt asking the nurse if they used a peripheral IV. The computer application always asks the nurse if there was a peripheral IV. Although, Medicare will not reimburse for this service and the application will not attempt to bill Medicare, the question is relevant for complete documentation in the patient's Treatment Sheet. There was no administration of a peripheral IV, so, the nurse clicks on No.

FIG. 21 is a screenshot of the top half of a Treatment Sheet. The Treatment Sheet generated for the encounter appears for review by the nurse. It has been broken into two parts here to paste it into this document. It shows the services performed, as well as the recorded Vitals and Comments. The Treatment Sheet records the waste for all of the drugs here.

FIG. 22 is a screenshot of the bottom half of a Treatment Sheet showing signature lines for the doctor and nurse. At this point, the nurse may print the Treatment Sheet and put it into the patient's chart. Notice there are two lines. One is for the doctor's signature and the other is for the nurse to sign.

Figure 23:
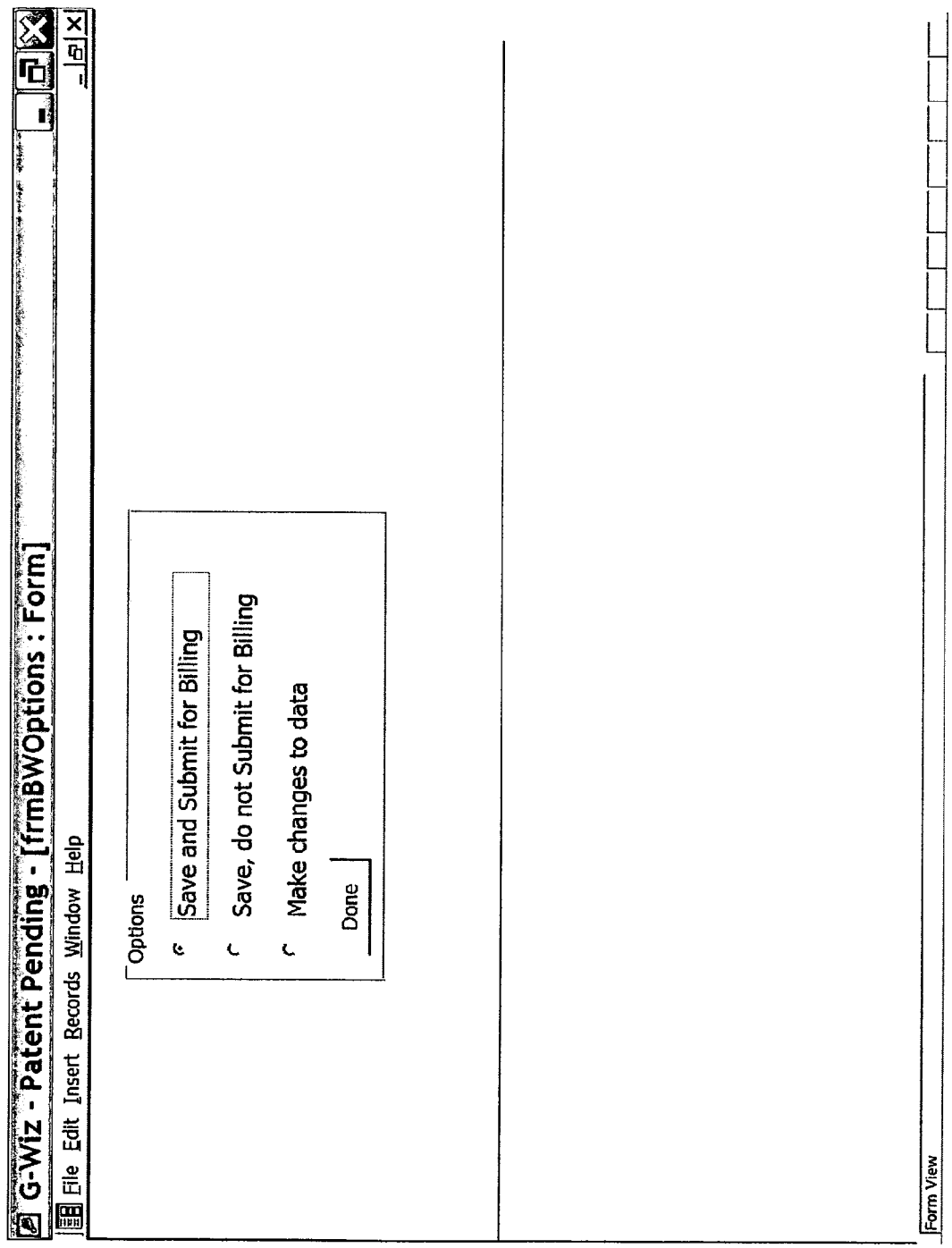

FIG. 23 shows the selected radio button to release the Superbill for billing. When the nurse clicks on Close, the application presents this window. The nurse elects to take the default action and clicks Done.

Figure 24:
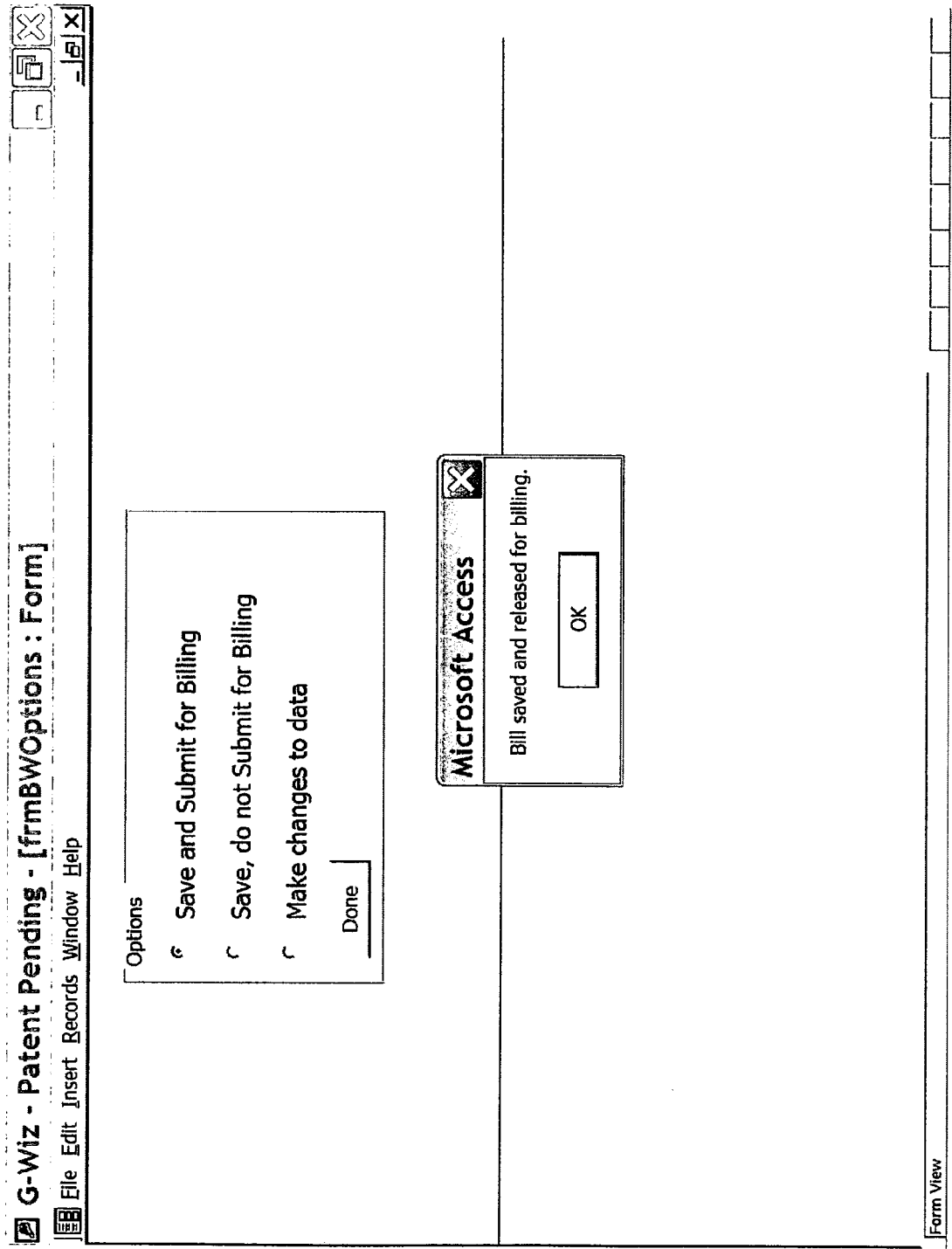

FIG. 24 shows a prompt confirming that the computer application saved and released [the Superbill] for billing. The Treatment Sheet is stored for later printing at any time. Because the nurse released the Superbill to billing, no further changes should take place to the encounter. The application locks the encounter, preventing any further changes until the user intentionally unlocks the encounter. After the nurse clicks OK, the Patient Information Window appears.

Figure 25:

FIG. 25 shows the Patient Information Window. Notice the application updated the Last Date of Chemo. While not relevant for a Medicare patient, it is applicable for the billing of Chemo Follow-Up Visits for Blue Cross patients. Let's have the nurse click on List All Bills.

Figure 26:
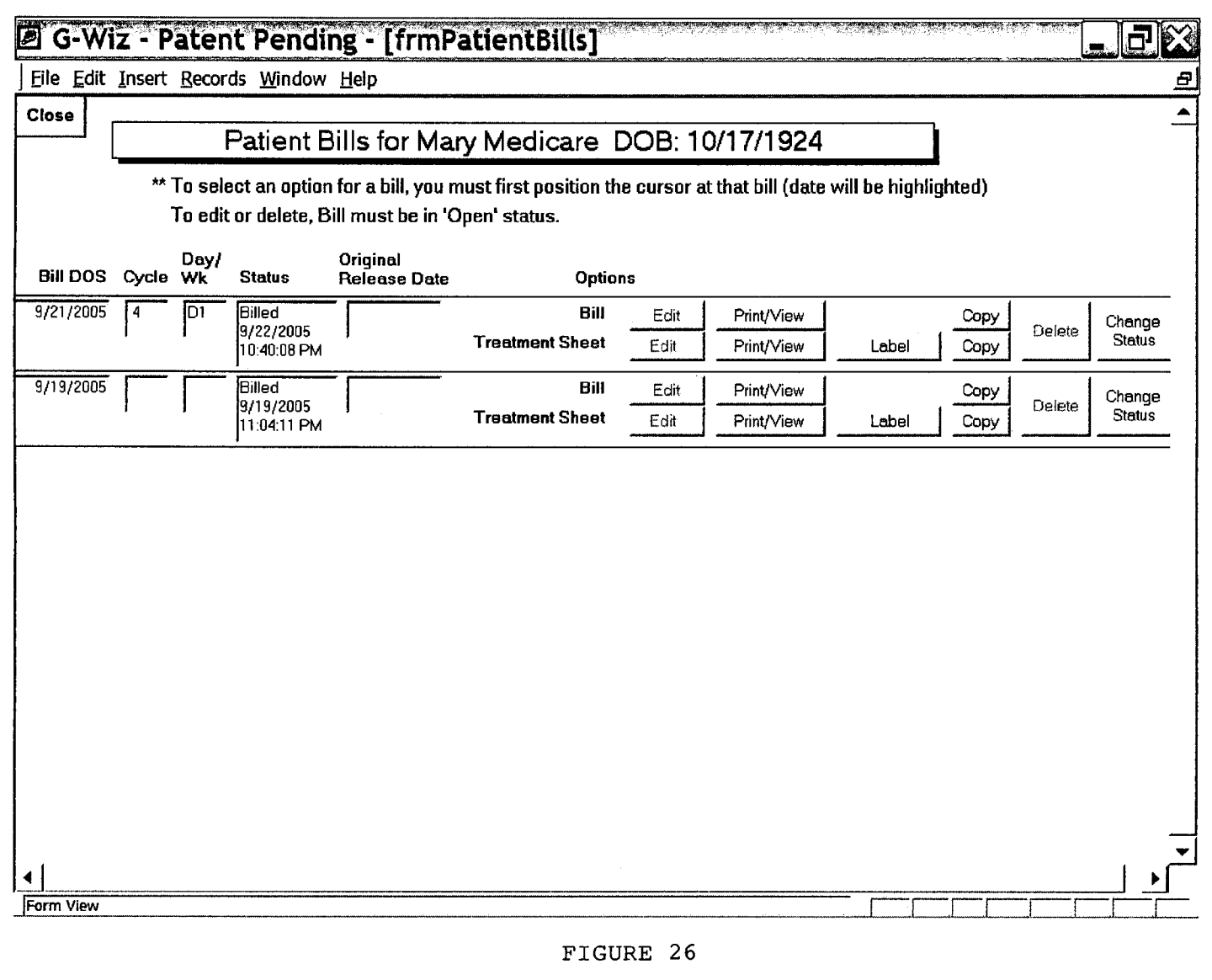

FIG. 26 shows all of the saved encounters for Mary Medicare. The application presents all the saved patient encounter records to the nurse. The application has set the Status for the last encounter to Billed with the Date and Time when the nurse last released it.

For the biller to obtain the Superbill, under Options to the right of Bill, the biller clicks on Print/View.

If the insurance for the patient has been changed in the Patient Information Window, the user must Change Status to Open the bill and then Edit followed by View Superbill to generate a new Superbill with the rules for the new insurance.

FIG. 27 is a screenshot of the top half of the Superbill. This is the Superbill for the patient's Date of Service (DOS). The billing algorithm parsed the Treatment data. G0359, Chemotherapy administration, intravenous infusion technique; up to one hour, single or initial substance/drug was determined to be the Initial/Primary Procedure. The billing algorithm parsed the remaining Admin's and generated the following G-Codes with their respective quantities.

For Claim #1, G0359, Chemo IV infusion, single/initial hour drug, 1st hour (abbreviated description for G0359 from ProcsAndCodes) is listed first because it is the Initial G-Code. Each additional hour of Chemo infusion up to 8 hrs (abbreviated description for G0360) immediately follows. The G0360 has a quantity of one, since the G0359 accounted for the first hour and the billing algorithm rounded up the additional 35 minutes yielding the additional hour.

The most expensive chemotherapy drug, Rituxin, is right behind the two G-Codes that represent its administration. Its dosage of 675 mg resulted in seven HCPS Billing Units. The application has already documented the 25 mg of waste in the Treatment Sheet.

The three Demonstration Codes are next because if they are not in the same claim as a chemotherapy infusion or push, Medicare will not provide for their reimbursement.

There can only be six lines per HFCA 1500 Claim; so, the application calculates a Claim charges subtotal to assist the biller with verification of correct data entry into the billing software. When the biller enters the first claim into the billing system, the billing system should agree with the Claim charges subtotal of $4,657.00. Otherwise, a data entry error probably occurred during data entry or the Fees are different in the billing system. It is recommended that the Fees be identical between this application and the billing system in order to verify data entry. The application then generates the next claim.

Not every billing software system limits data entry to six lines to mirror the HFCA 1500 Claim Format. Some will accept more than six lines for data entry. The computer application also generates the accumulated Bill Charges for the entire encounter, which can serve as balance total for the biller to verify data entry.

FIG. 28 is a screenshot of the bottom half of the Superbill. The second claim begins with G0362, Chemotherapy administration, intravenous infusion technique; each additional sequential infusion, (different substance/drug) up to one hour followed by the additional chemo drug, Fludarbine. The dosage equated to a HCPS Billing Quantity of one.

Next is G0349, Intravenous infusion, for therapy/diagnosis (specify substance or drug); additional sequential infusion, up to one hour. The infused non-chemotherapy drug, Diphenhydramine, follows with a HCPS Billing Quantity of one. In addition, the billing algorithm knows that a secondary diagnosis of Nausea with Vomiting (78701) is a prerequisite for its reimbursement. The required secondary diagnosis code for this drug is set in DrugsAndProcs.

Because Port Flush Services and Supplies are bundled expenses, the billing algorithm does not bill the J-Codes for the Heplock and the 5 cc of Sterile Saline. The billing algorithm has listed the bags of Saline with a quantity of two for the 50 ml bags and a quantity of one for the 250 ml bag. The Claim Charges for Claim #2 total $597.00.

Last is the charge for the Complete Blood Count. Since, all billable expenses are now complete, another Claim charges total appears, as well as the Bill charges for the patient encounter. This should balance with the billing system with a total for $17.00 for the third claim and a complete total for the entire encounter for $5,271.00. Like the Treatment Sheet, the user can print the Superbill at this point. There is another option to print the Superbills by a range of Bill Release Dates (Invoked through BillingReports). Close returns to the prior window.

FIG. 29 shows the two encounters for Mary Medicare again. The application shows that the bill was originally released for billing on Sep. 22, 2005 at 10:40 PM. When a user clicks on Change Status and confirms by clicking Yes, the application copies the date and time to the Original Release Date. The next Submit for Billing revises the Status with the new Release Date. From the time stamp, the nurse and biller can determine if they can simply swap the new bill with the old bill. If there is a substantial difference in the dates, the biller will immediately see the need to rebill for any added, deleted, or modified charges that appear on the new Superbill.

Close returns to the Patient Information Window.

Figure 30:
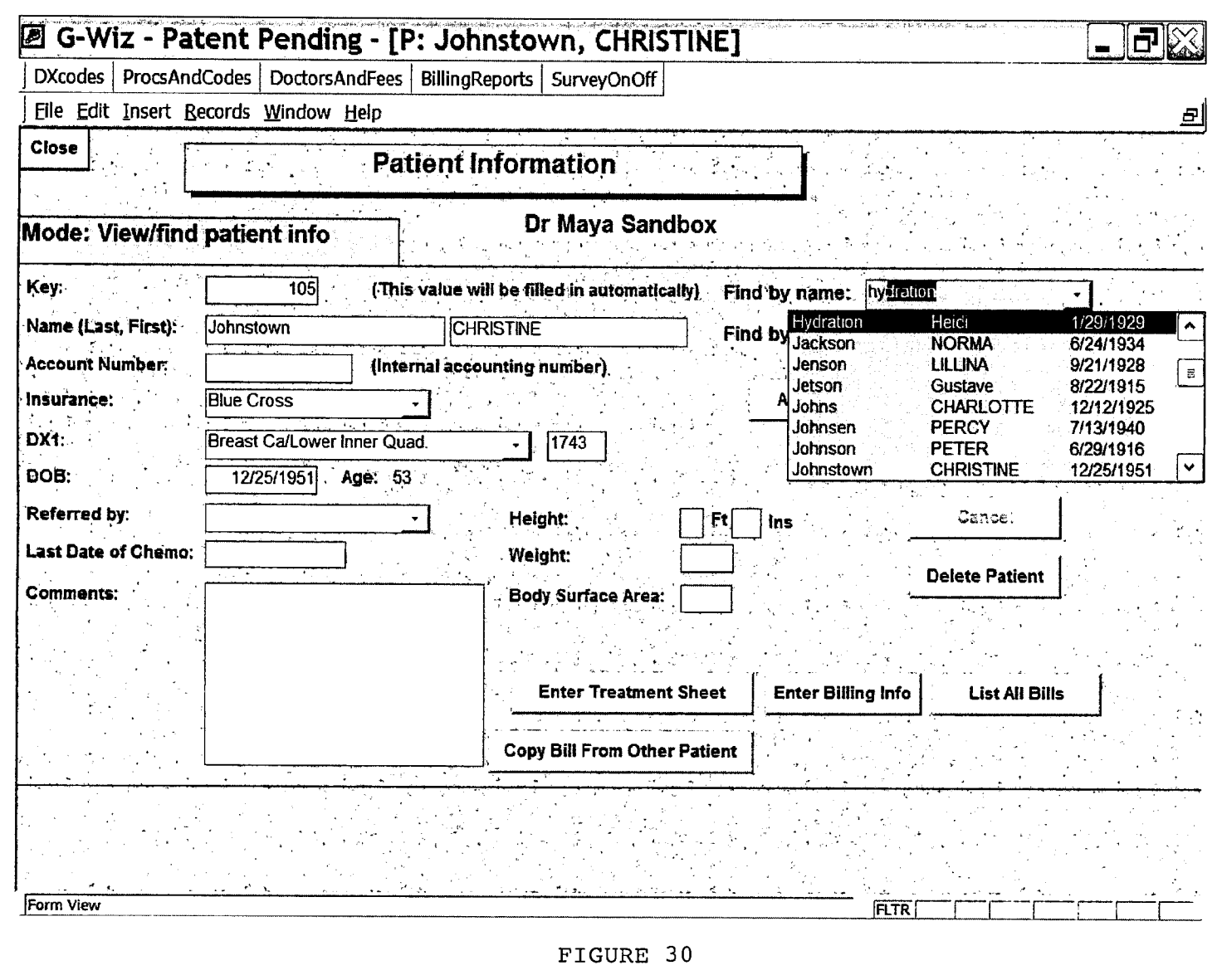

FIG. 30 illustrates selecting another patient from the Patient Information Window. The nurse has returned to the Patient Information Window. The nurse entered the letters hy to the right of Find by name: In our small "Sandbox" database, the fictitious patient with a last name of Hydration appears. In a real setting, more characters of the last name might be necessary. At this point, the nurse presses the Enter key with the following result:

Figure 31:
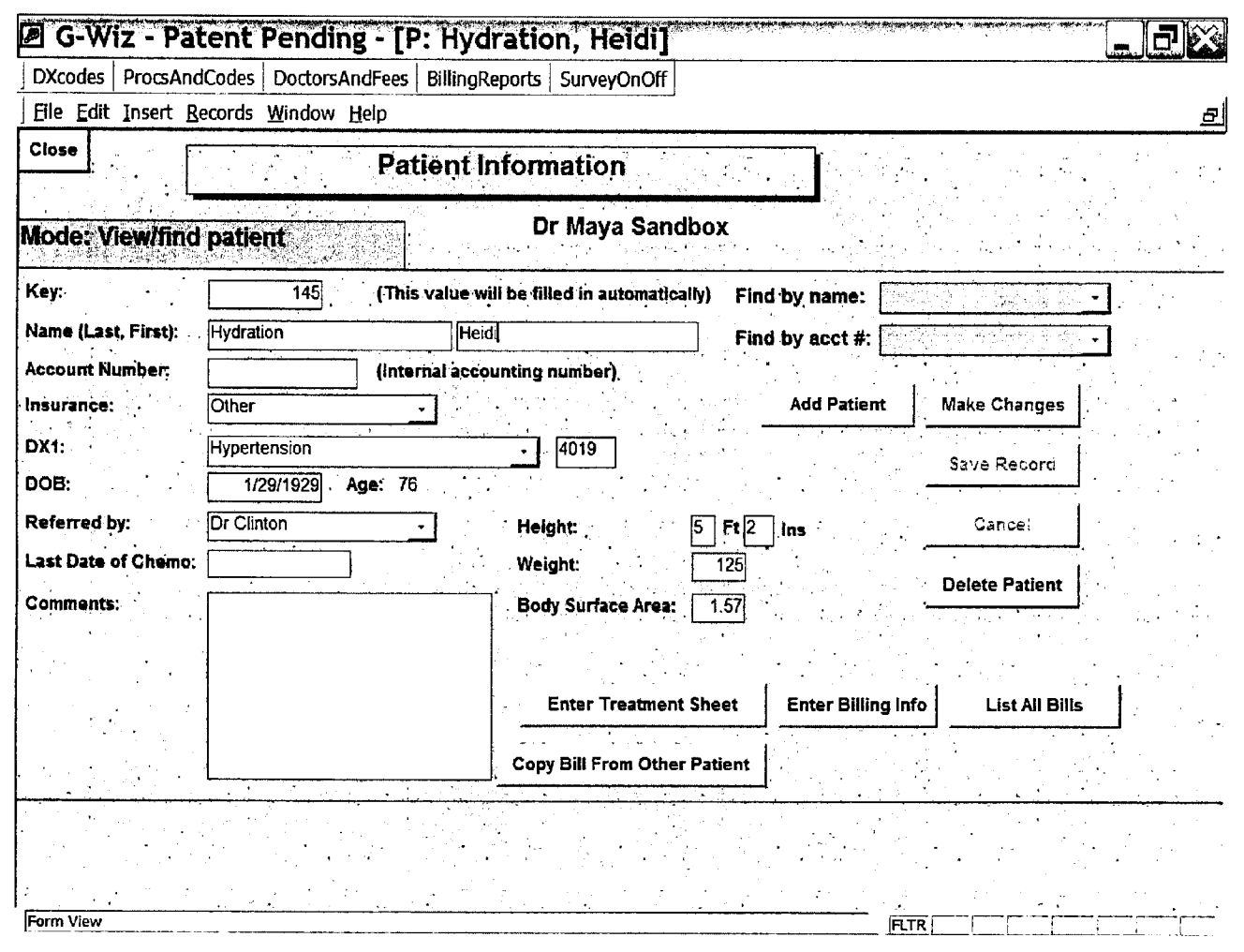

FIG. 31 shows the selection of Heidi Hydration. Heidi Hydration appears with her basic patient information. Let us pretend the user this time is a biller. Thus, the biller clicks, Enter Billing Info and is positioned at the Fluids tab. The application does not present a Survey tab because Heidi is not a Medicare patient. The application presented the Calendar for the DOS and the biller clicked on the day representing Sep. 19, 2005.

Figure 32:
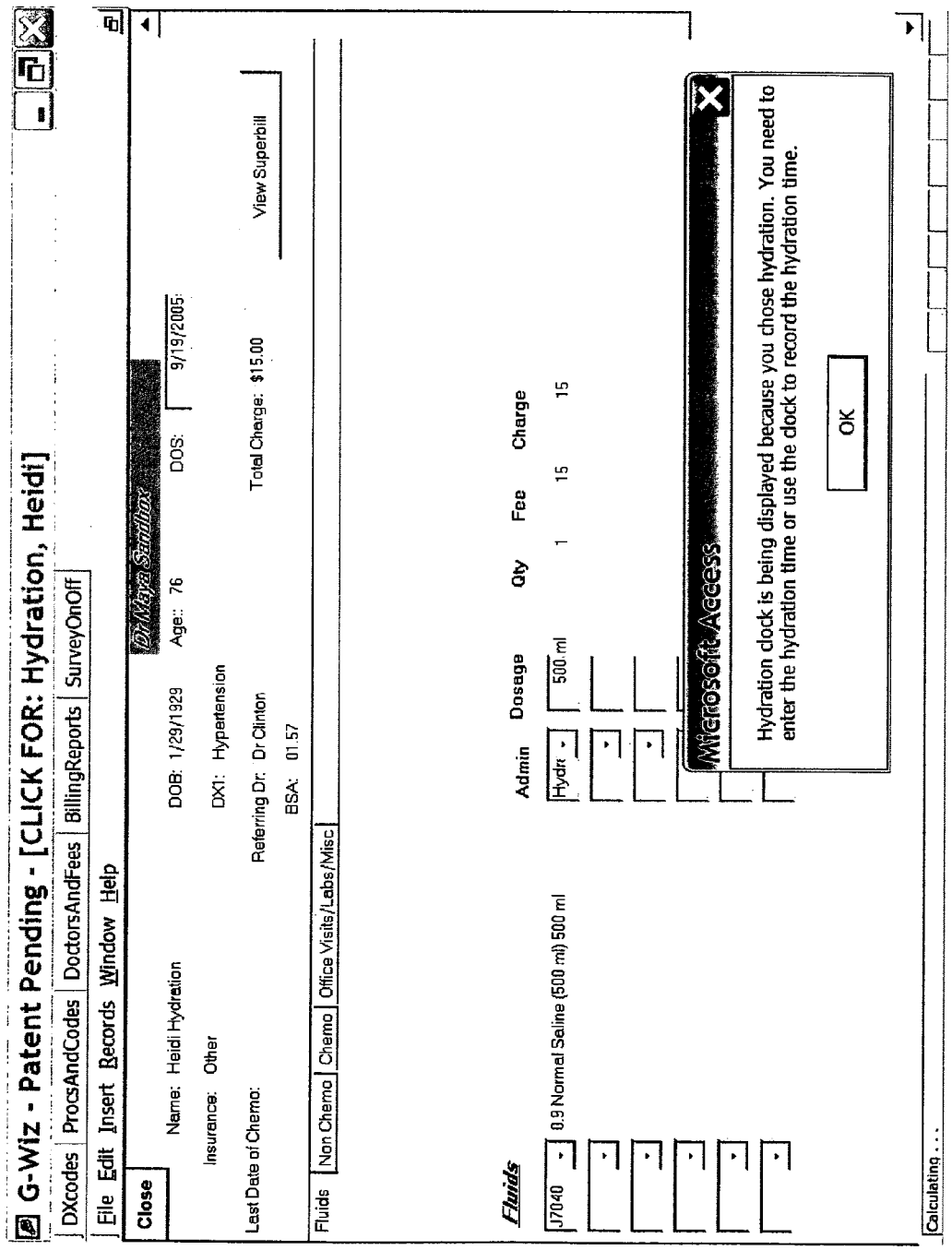

FIG. 32 shows the Fluids Tab after the user has selected Hydration. Let us pretend the biller is working off a standard paper superbill, not this application's Superbill, but one drafted by the doctor's practice. This practice documents the actual start and stop times recorded by the nurse on the superbill. In addition, on this superbill, the nurse has checked off services for Hydration, Phlebotomy, and Venipuncture, but forgot to communicate the administration of a Peripheral IV.

The biller has already selected an Admin of Hydration (The default of Dilution was overridden by selecting Hydration from the Drop Down Box) for J7040 with a Dosage of 500 ml. Hydration has a billable G-Code based on duration. The application is about to display a Hydration Clock for the user to establish the Start Time and End Time. Notice the Total Charge of $15.00 to the left of View Treatment Sheet. The application has begun to tally the total charges for this patient encounter. ProcsAndCodes has a Fee of $15.00 for J7040.

Figure 33:
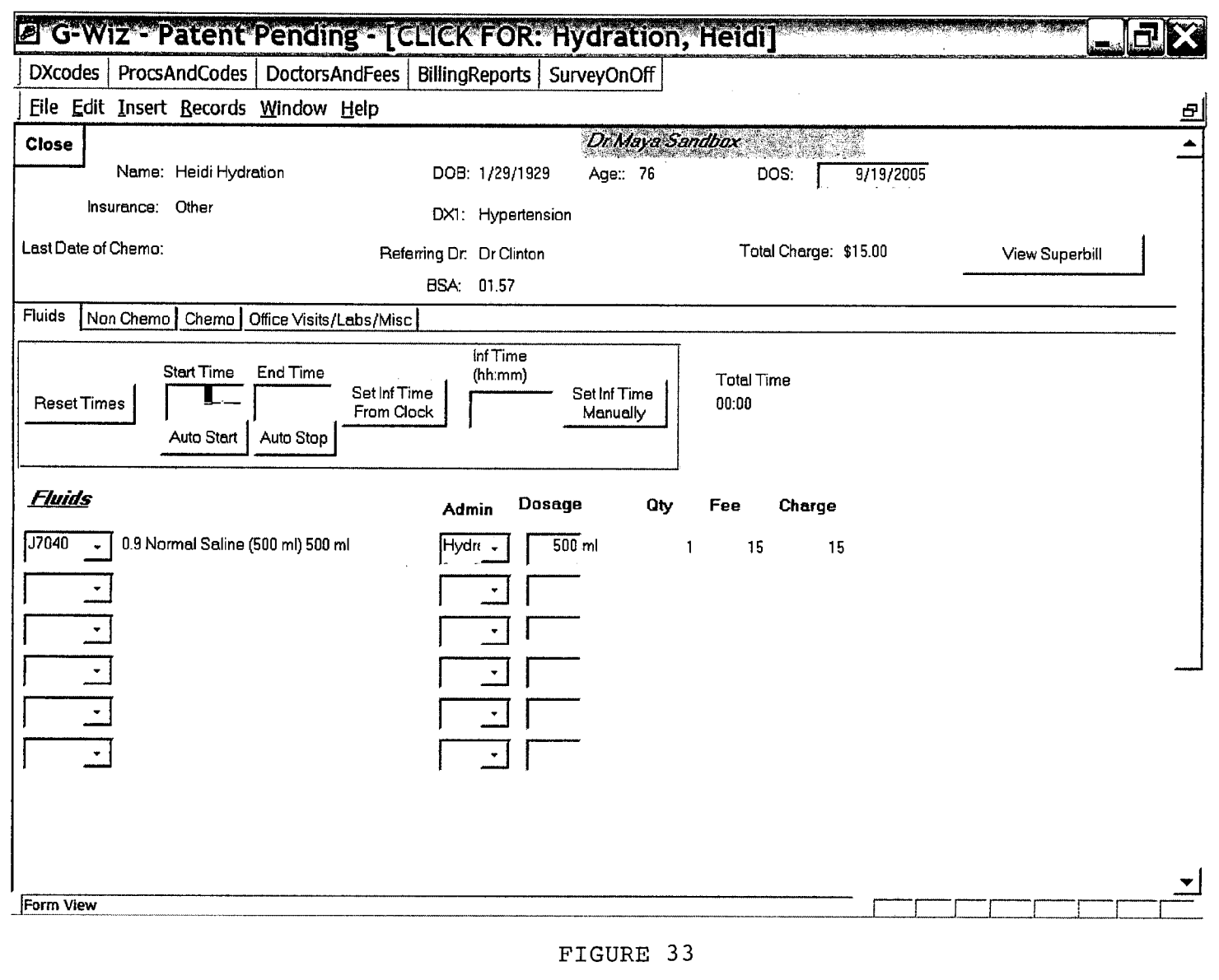

FIG. 33 shows the Hydration Clock. The biller has clicked the OK button resulting in the display of the Hydration Clock. The Hydration Clock acts just like the Infusion Clock explained before. Here it is more obvious that the clock is for Hydration because this entire tab is devoted to Hydration. With the Treatment Sheet method of data entry, the user knows the clock is for Hydration when the application highlights a line with an Admin of Hydration in the light blue, we saw before.

Figure 34:
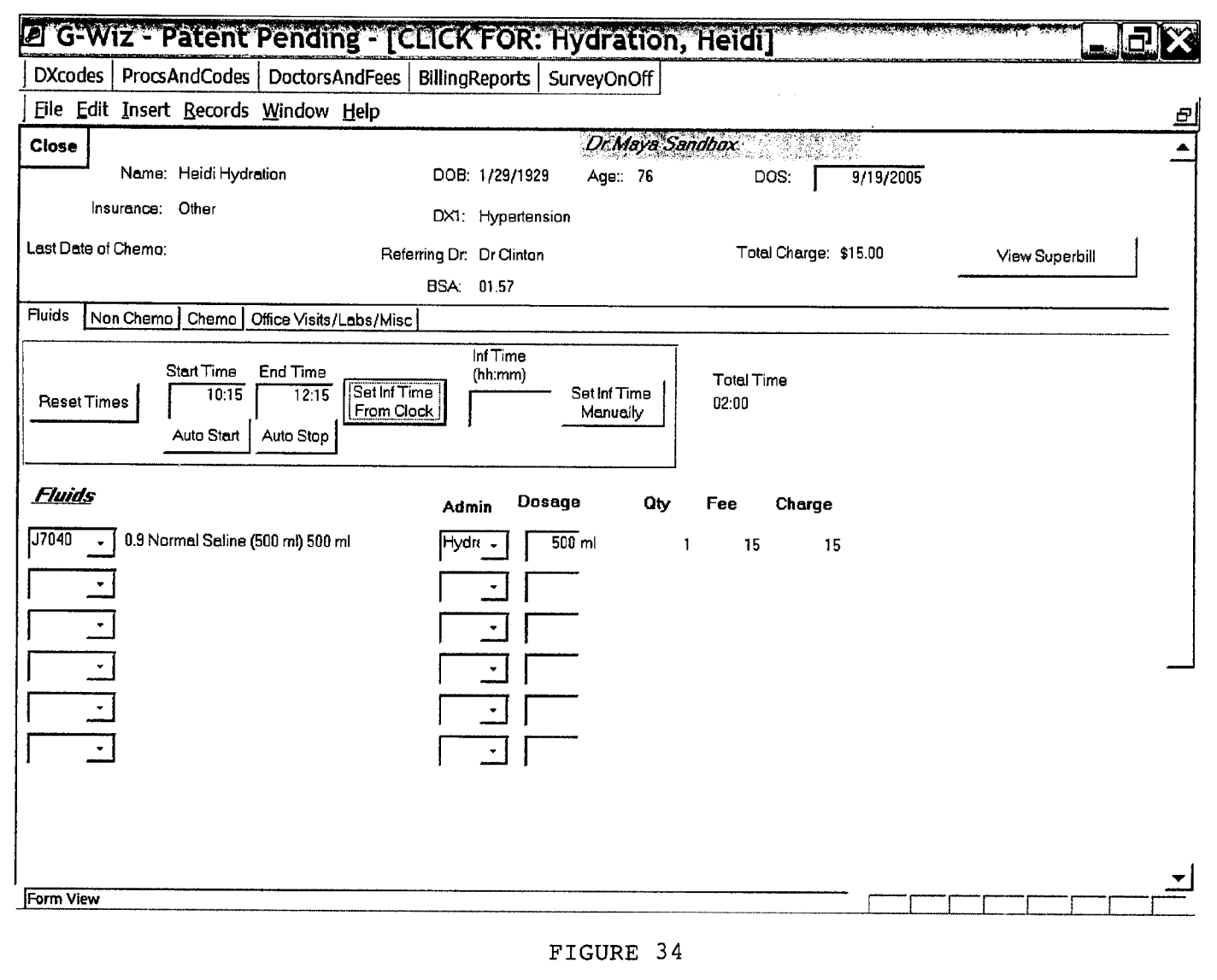

FIG. 34 shows the entered Start Time and End Time for the Hydration. The biller has entered the logged Hydration Times and clicked Set Inf Time From Clock to calculate and record the elapsed time, which now appears under Total Time. Next, the biller clicks on Office Visits/Labs/Misc.

Figure 35:
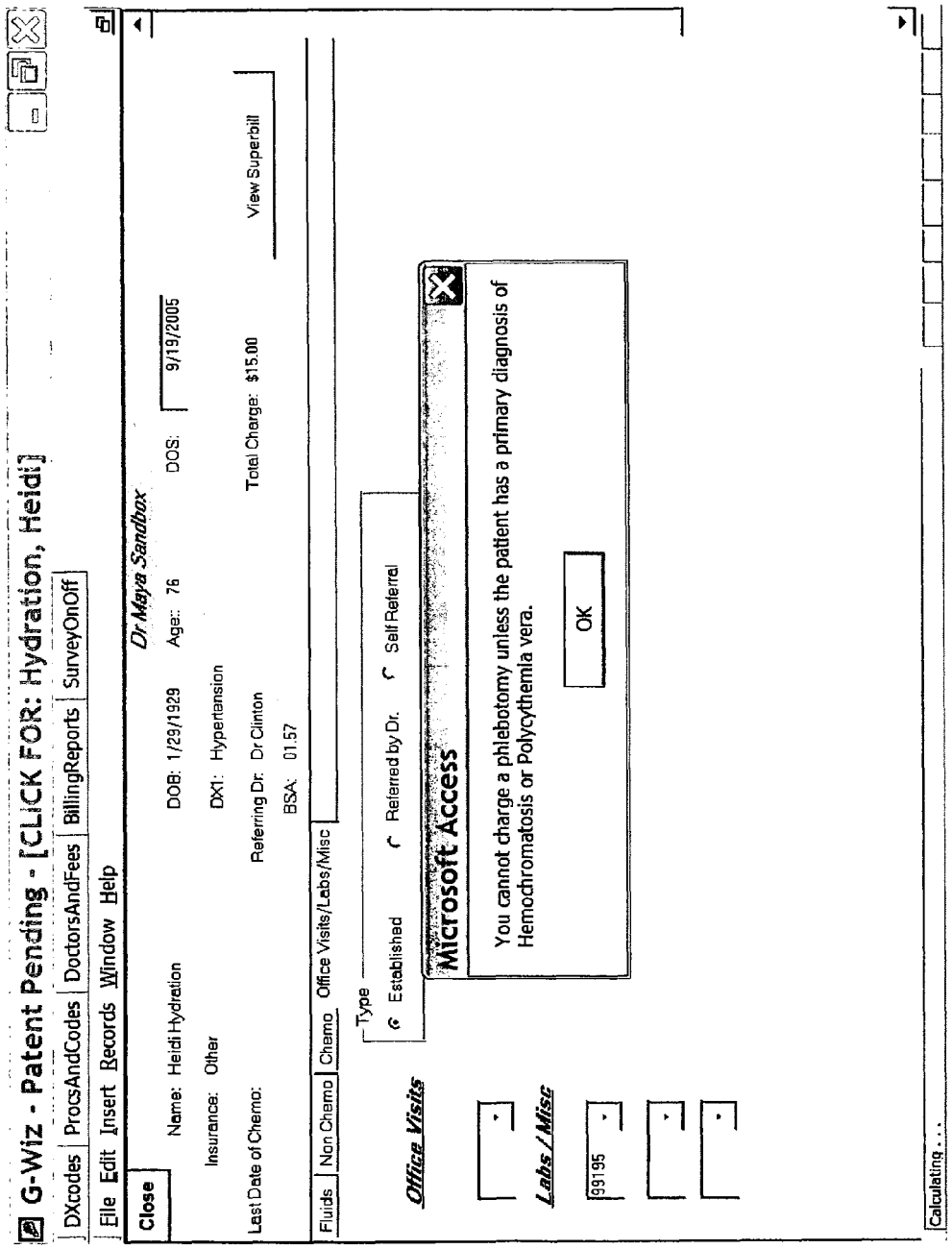

FIG. 35 shows the rejection of a Phlebotomy (99195) by the computer application. Because the nurse had marked Phlebotomy, the biller selects it [99195] while in this tab. The biller is going to have to consult with the nurse or the doctor regarding the primary diagnosis code. To ensure proper billing, the biller has to: Remove the Phlebotomy entry; View Superbill; Close; and Save, do not Submit for Billing to return to the Patient Information Window. After confirming, which of these conditions is appropriate, the biller will click on Make Changes to update the DX1 for the patient. After clicking on Save Record, the biller clicks on List All Bills and then clicks on Edit to get back to the DOS. As you can see, things are bound to go faster with the Treatment Sheet performed by the nurse. The biller, again, selects Phlebotomy from the drop down and then clicks on View Superbill.

Figure 36:
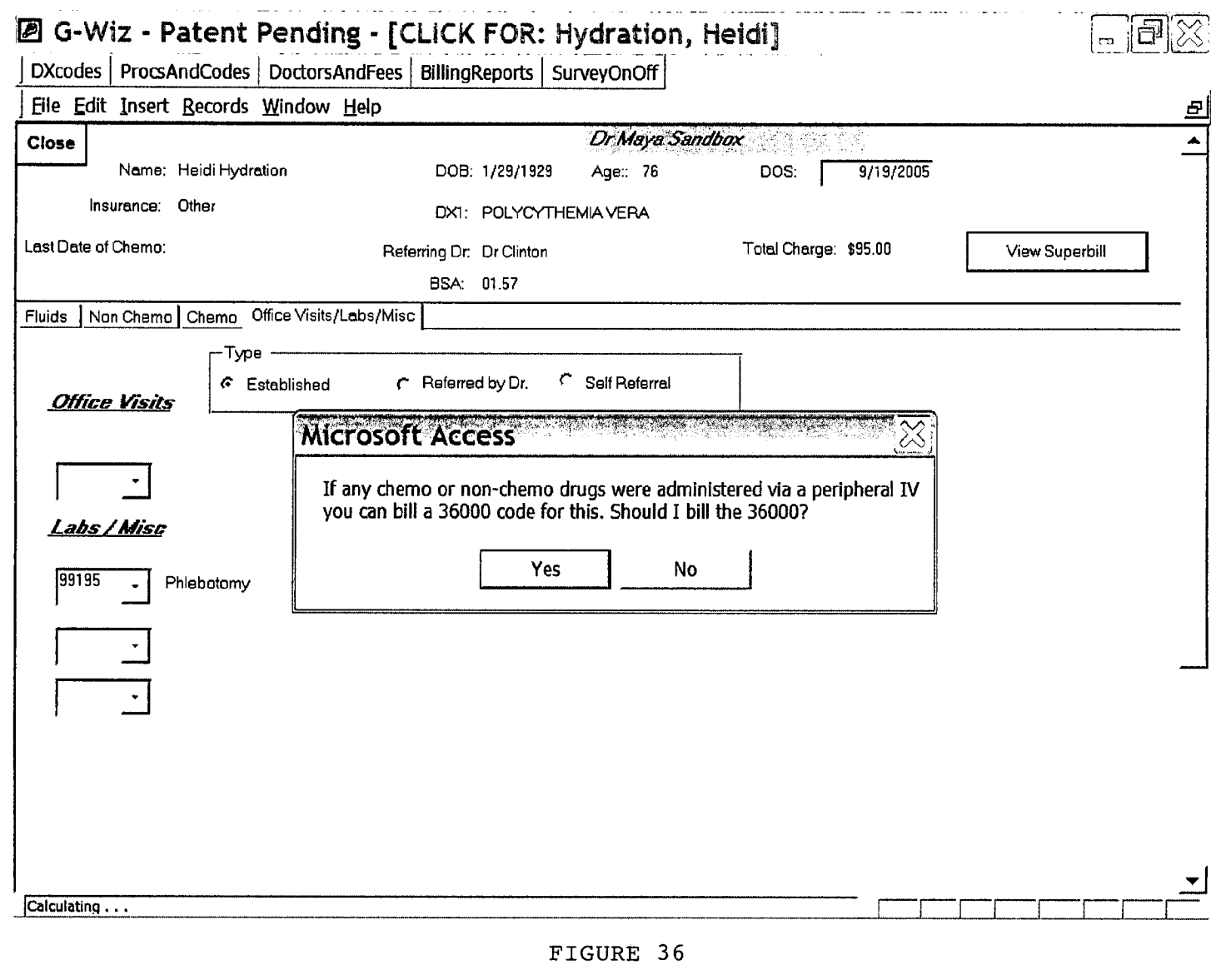

FIG. 36 shows the prompt asking if the nurse administered the patient through a peripheral IV. Presumably, the biller was finished with data entry in the other tabs, but not necessarily. A user can always return to reenter data. Regardless, the Billing Algorithm started to analyze the data entered so far and detected that a Push or Infusion or Hydration occurred in one of tabs. The application issued a prompt to determine if the administration was via a peripheral IV. Because Insurance is Other, if the biller responds with Yes, the application will respond with another prompt asking if there were [multiple sites accessed]. If the user responds in the positive, the billing algorithm bills a second 36000. The billing algorithm will automatically apply a 59 Modifier to the first 36000 and a 76 Modifier to the second 36000 on the claim lines.

Because the nurse forgot to record this on the practice's superbill, the biller should consult with the nurse again. There is the temptation to decline the expense, since chemotherapy patients usually receive administration through a Port. However, some oncology patients do receive treatment via Peripheral IV, as do as a variety of Hematology patients. We hope that all billers make confirmation with the nurse before they decline the billing of the 36000. Again, here is another illustration of the desirability of charge capture by the nurse. After consulting with the nurse a second time, the biller responds to the prompt by clicking Yes.

Figure 37:
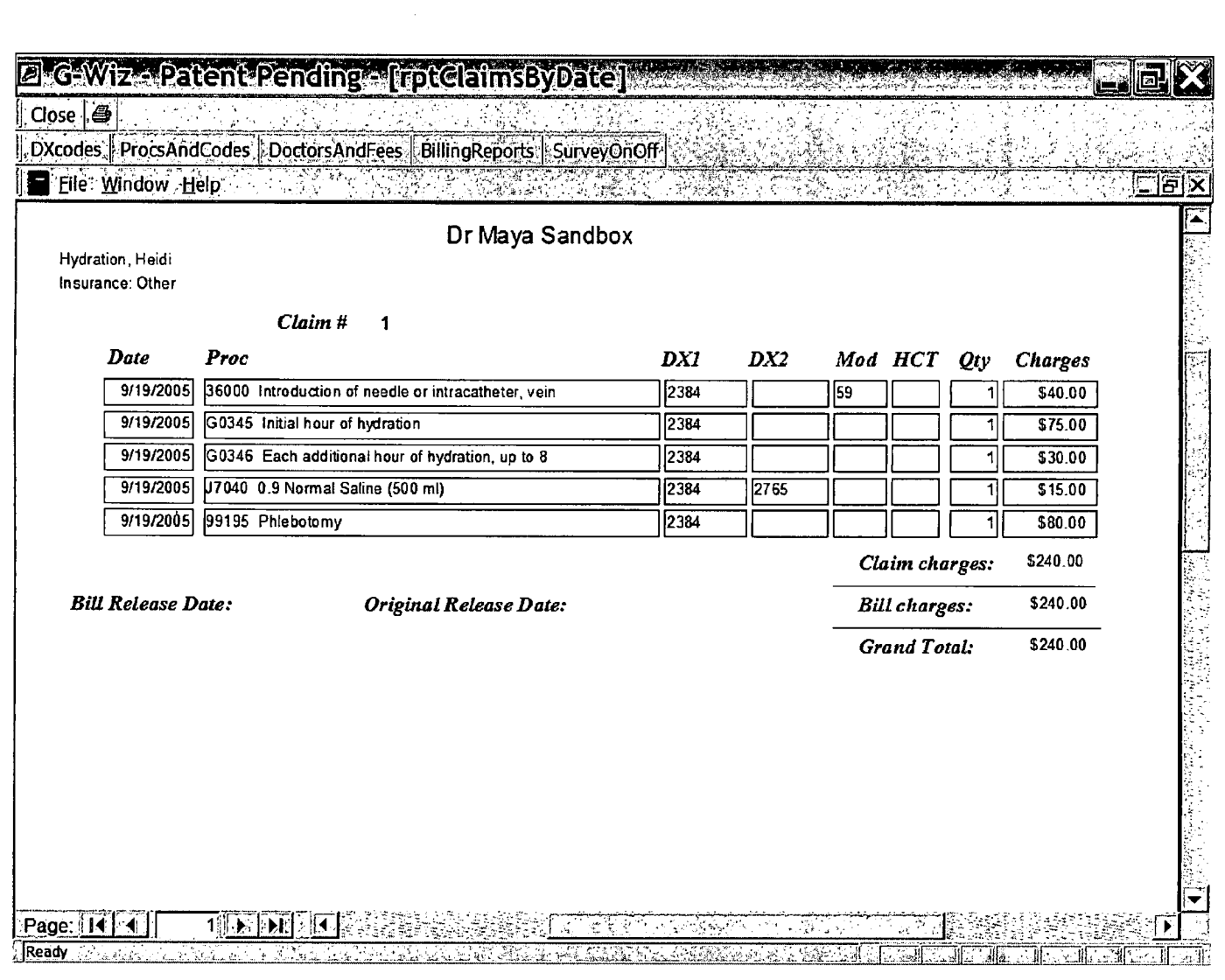
Figure 38:
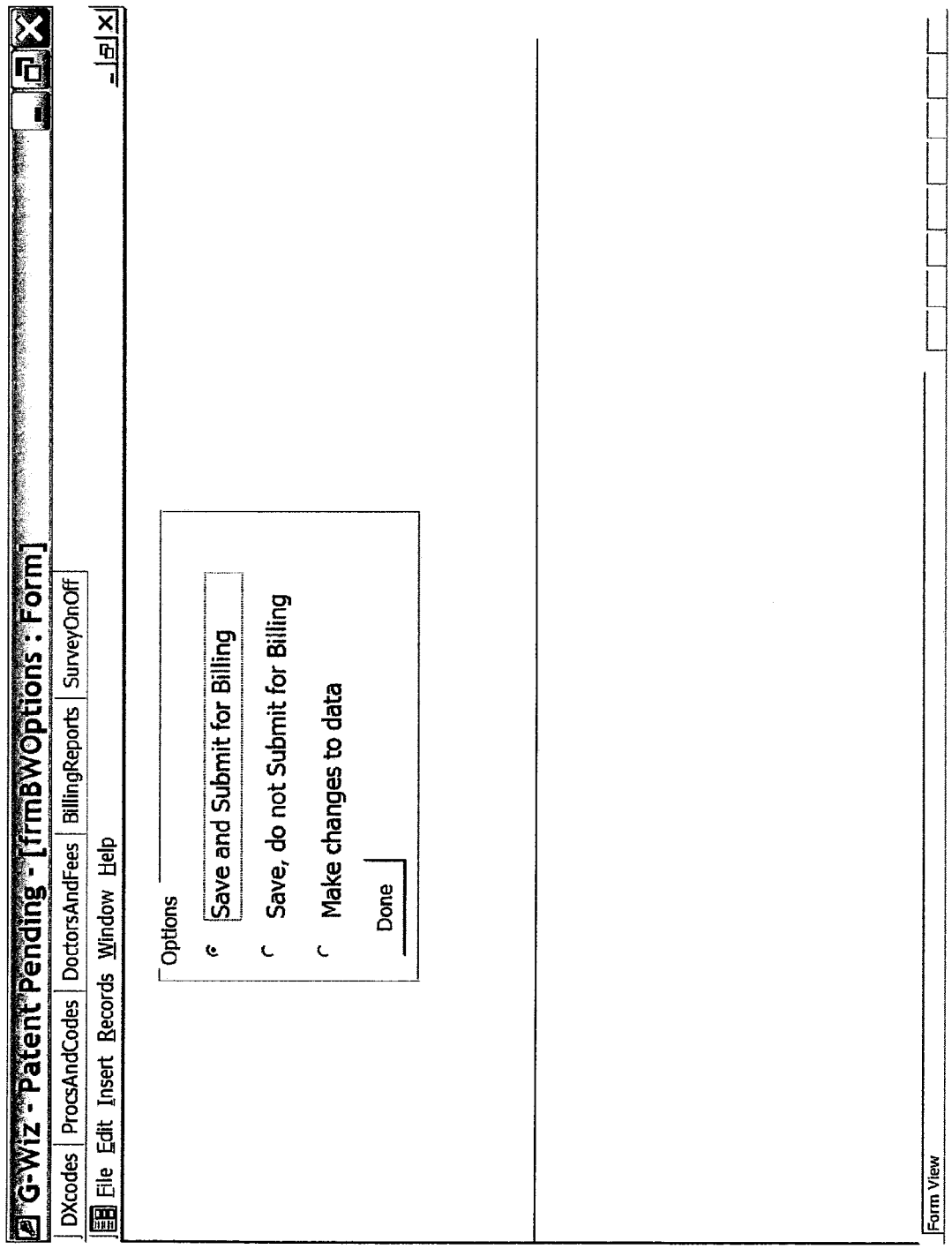

FIG. 37 shows the screenshot for the Superbill for the hydration through a peripheral IV. The computer application generated this Superbill. A Bill Release Date does not appear because the biller has not yet released the Superbill. The biller realizes that Venipuncture was on the practice superbill, but forgot to select it. To add more items to the patient encounter, the biller clicks on Close at the top left corner of the window. What appears next is:

FIG. 38 illustrates how to make changes to the treatment data. Instead of taking the default, Save and Submit for Billing, the biller clicked on the radio button to the left of Make changes to data. The biller knows that a service for this encounter is missing. Afterwards, Done is clicked. The application returns the biller to the Fluids Tab. The biller clicks on the Office Visits/Labs/Misc.

Figure 39:
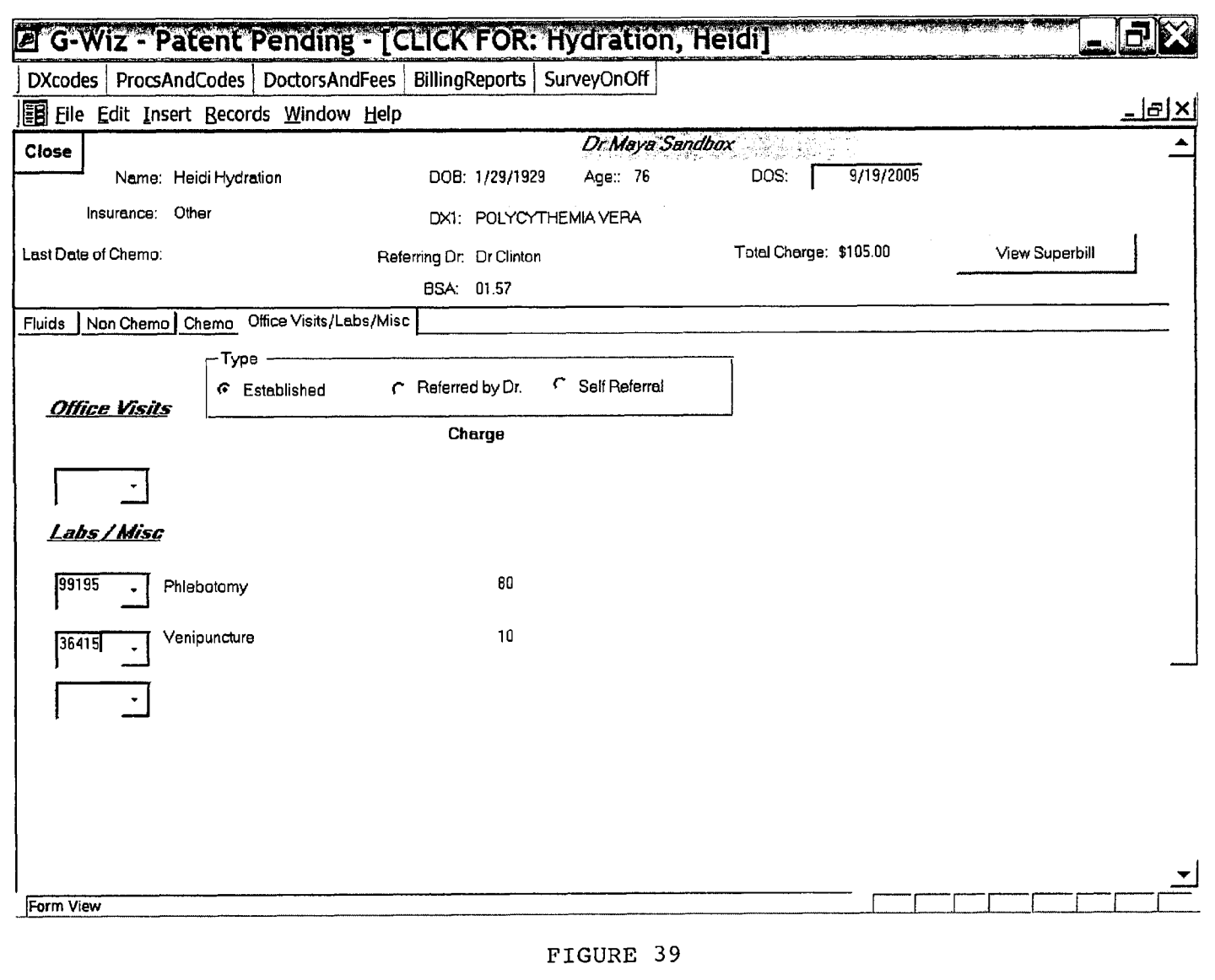

FIG. 39 shows the Office Visits/Labs/Misc tab. After selecting Venipuncture from the drop down list, the biller again clicks on View Superbill.

Figure 40:
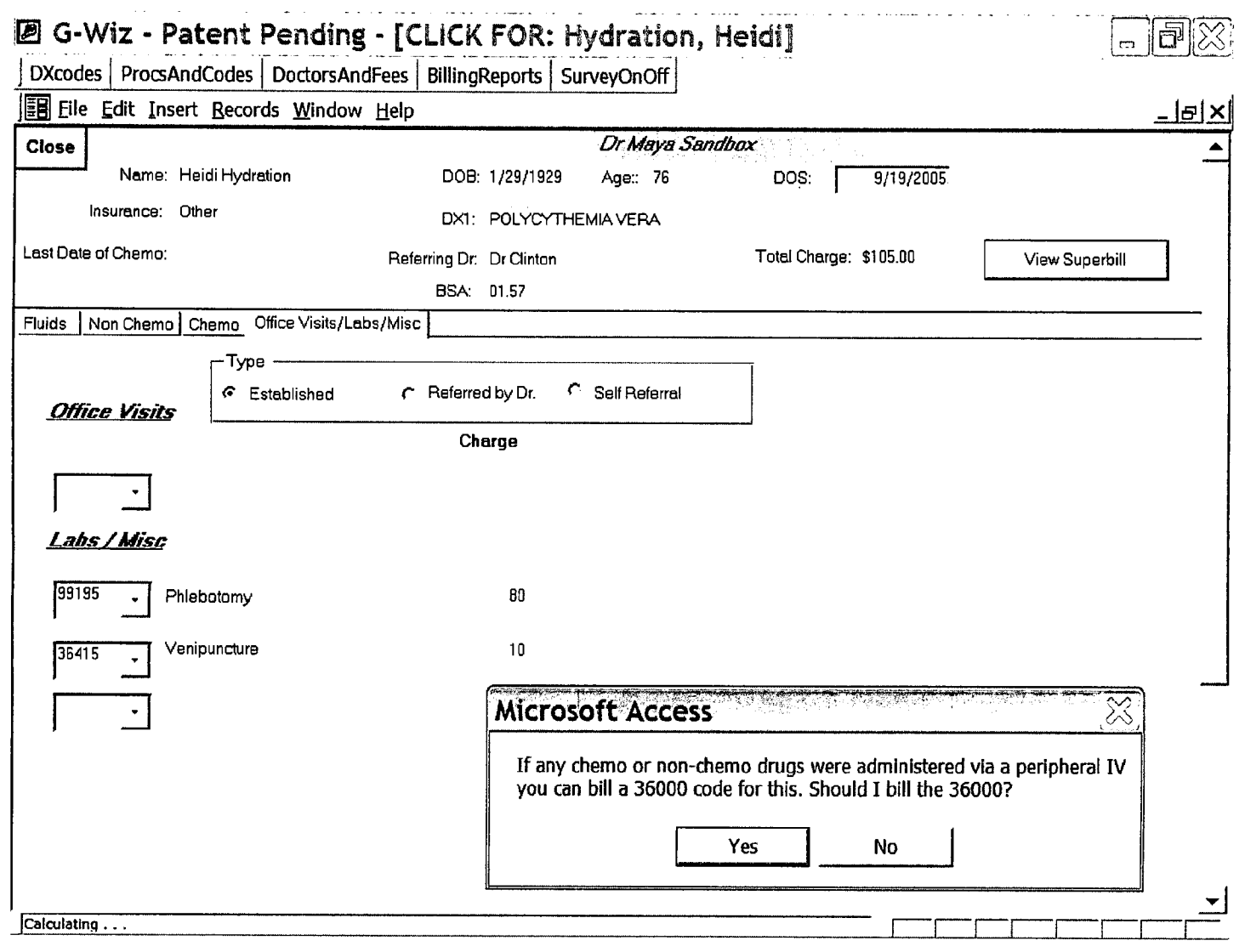

FIG. 40 shows the peripheral IV prompt that appears repeatedly. The application asks the question again because there is no drop down box for 36000 and the biller's answers could be different. The biller agrees to bill the charge by clicking Yes.

FIG. 41 is a screenshot of the Superbill with the additional service. The application displays the Superbill, showing the appropriate G-Codes, generated with their respective quantities.

Normally, an Initial G-Code occupies the first line of the first claim. Although, Hydration is the Initial/Primary Procedure, it benefits the insurance adjudicator to immediately show that the Saline administration occurred through a vein. Therefore, a 36000 with a 59 Modifier precedes the Initial Hydration G-Code.

Next, the Initial G-Code, G0345, Intravenous infusion, hydration; initial, up to one hour is generated, followed by G0346, Intravenous infusion, hydration; each additional hour, up to eight (8) hours. If there were three hours of Hydration, the quantity for G0346 would have been two. Since the patient received no chemotherapy or non-chemotherapy, G0345 and G0346 do not require a 59 Modifier. The J-Code for the Saline is next, accompanied by the required secondary diagnosis code 2765.

Finally, we see the procedure codes for the Phlebotomy and the Venipuncture.

The total for the claim is $250. After the biller enters these charges into the billing software, the balances should match, verifying that the biller has made the correct entries.

There is only one claim for this encounter. Therefore, the Claim charges and the Bill charges are both $250.00, established according to the Fee Schedule in DoctorsAndFees.

If the BillingReport Function had generated this claim, the Grand Total would equal the sum of all of the Superbills in the Date and Time Range specified by the user. At this point, the biller may print this Superbill, immediately or wait for completion of data entry for all of the patients. This may not occur until the end of the week. Let's presume the biller is going to wait until later. Therefore, the biller clicks Close located at the top left corner of the screen.

Figure 42:
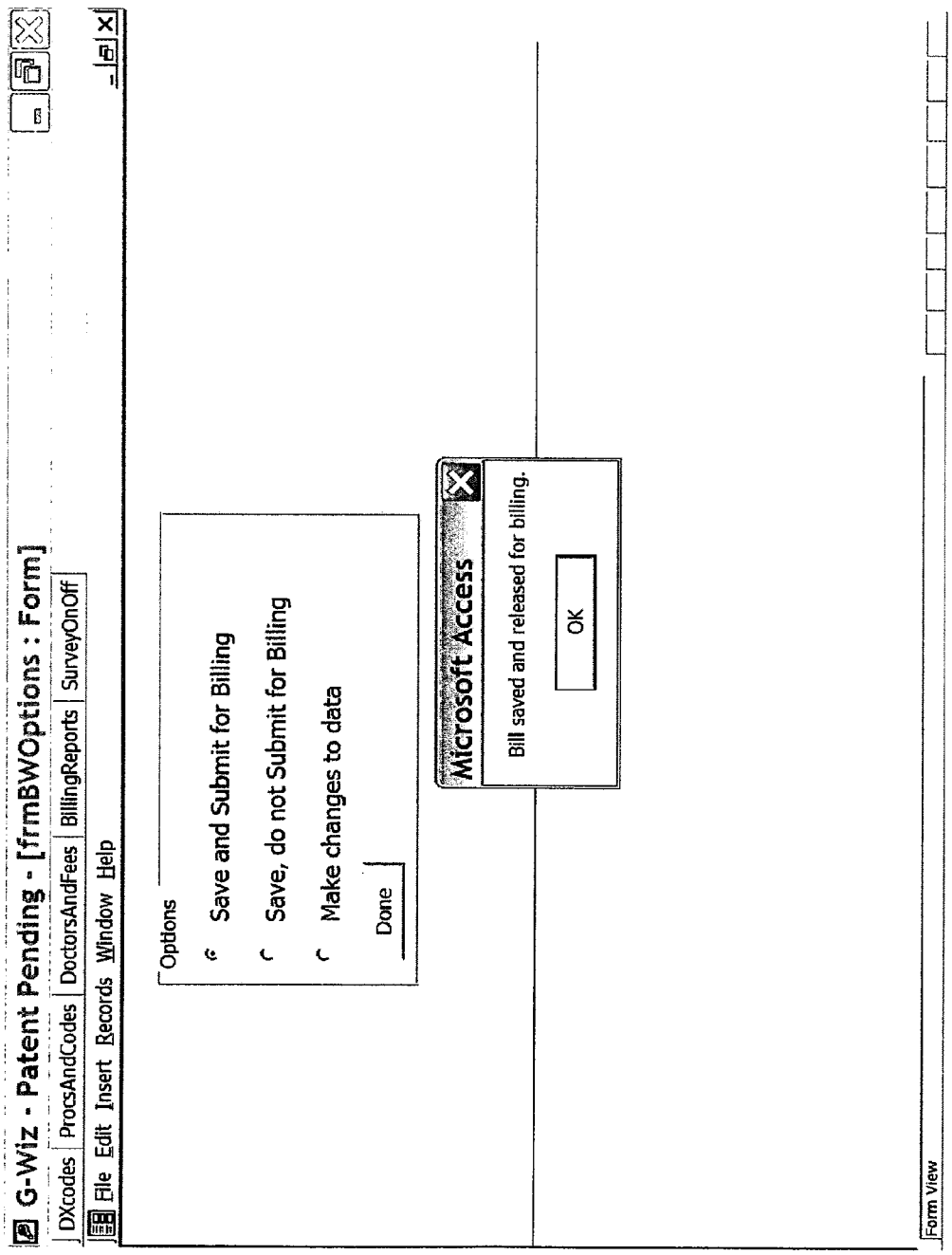

FIG. 42 shows the prompt, which confirms that the computer application has released the bill for billing. Clicking on Close, results in this window presented. The biller elected to take the default action and clicked Done, resulting in the Bill saved and released for billing message. The Superbill is stored for later printing. The application locks the encounter; preventing any further changes unless the user specifically unlocks it. After the biller clicks OK, the Patient Information Window appears.

Figure 43:
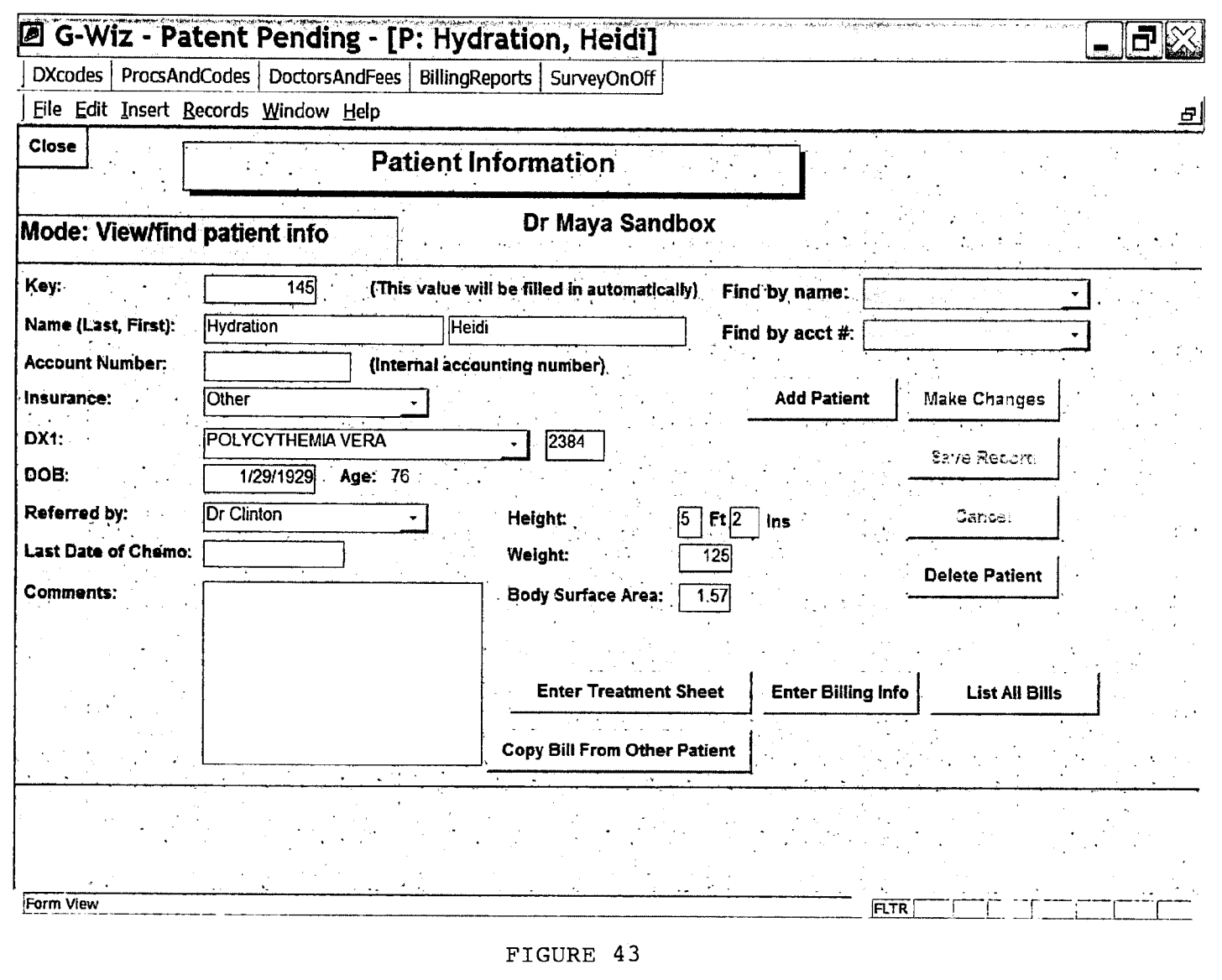

FIG. 43 illustrates the resulting return to the Patient Information Window. The biller clicks on List All Bills.

Figure 44:
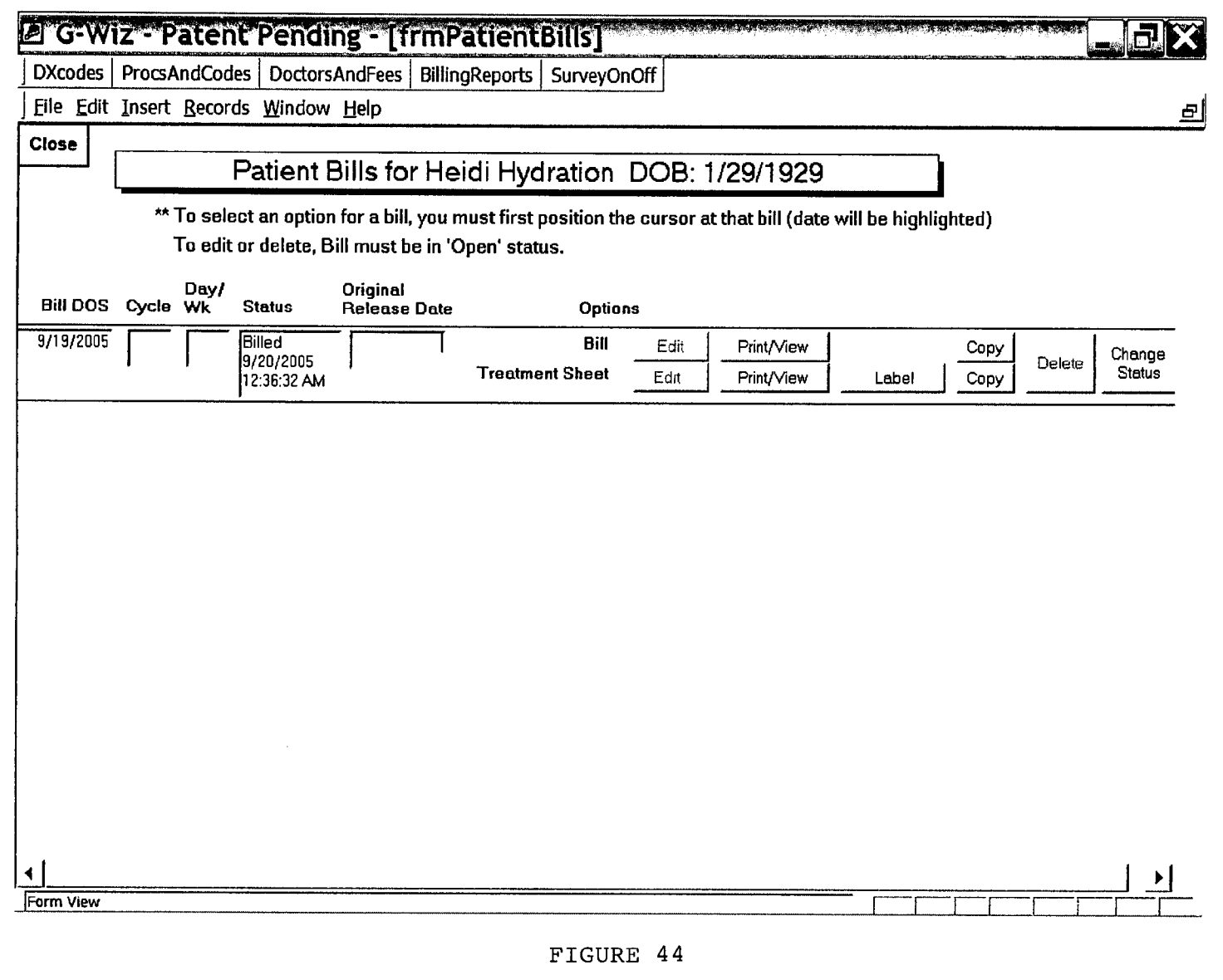

FIG. 44 shows there is only one encounter for Heidi Hydration. The application displays all of the saved Superbills to the biller for this patient. The application set the Status for Heidi Hydration's Superbill to Billed with the date and time when the user last released the encounter.

For the biller to obtain the Superbill, the biller clicks Print/View under Options and to the right of Bill. We have already seen what the Superbill looks like. Therefore, there is no need to show it again. However, let us see what happens if the user clicks on Print/View Treatment Sheet.

Figure 45:

FIG. 45 shows the screenshot that results when clicking on Print/View Treatment Sheet. Here is the result of Print/View Treatment Sheet for the patient encounter. Even though the nurse has not entered data for the patient through Enter Treatment Sheet, the application will still provide a Treatment Sheet. After printing the Treatment Sheet, the Nurse and/or Doctor can review, sign, and put into the patient's chart. The nurse can add information by Editing the Treatment Sheet. Note that the supplies and procedures are not in the actual sequence that they were performed, which is why entry by a nurse is preferred. The user can print this Treatment Sheet at this point. There is another option to print the Treatment Sheets by a range of Bill Release Dates. Close returns to the prior window.

Figure 46:
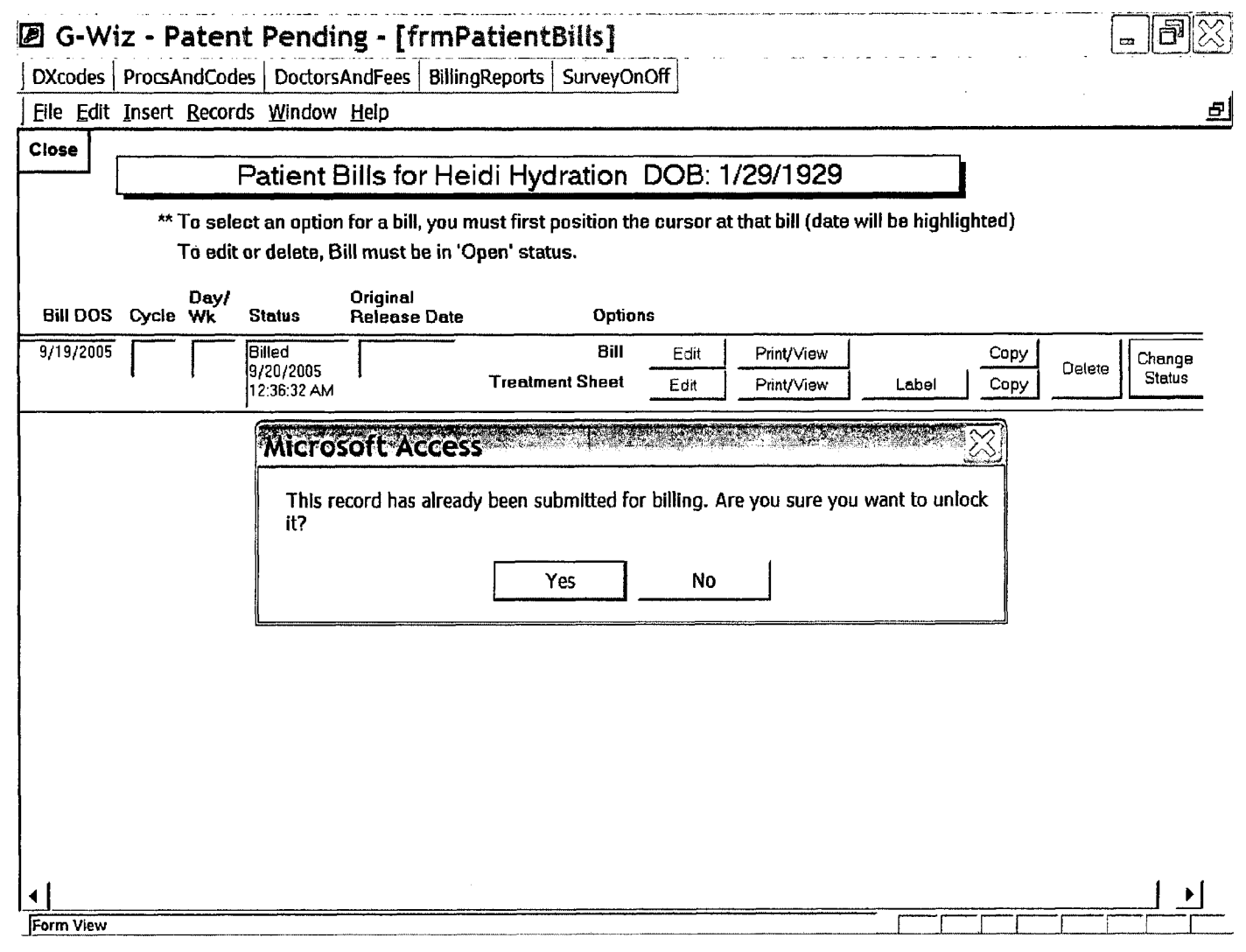

FIG. 46 illustrates the unlocking of a bill. The user has clicked on Change Status. The prompt requests verification to unlock the record.

Figure 47:
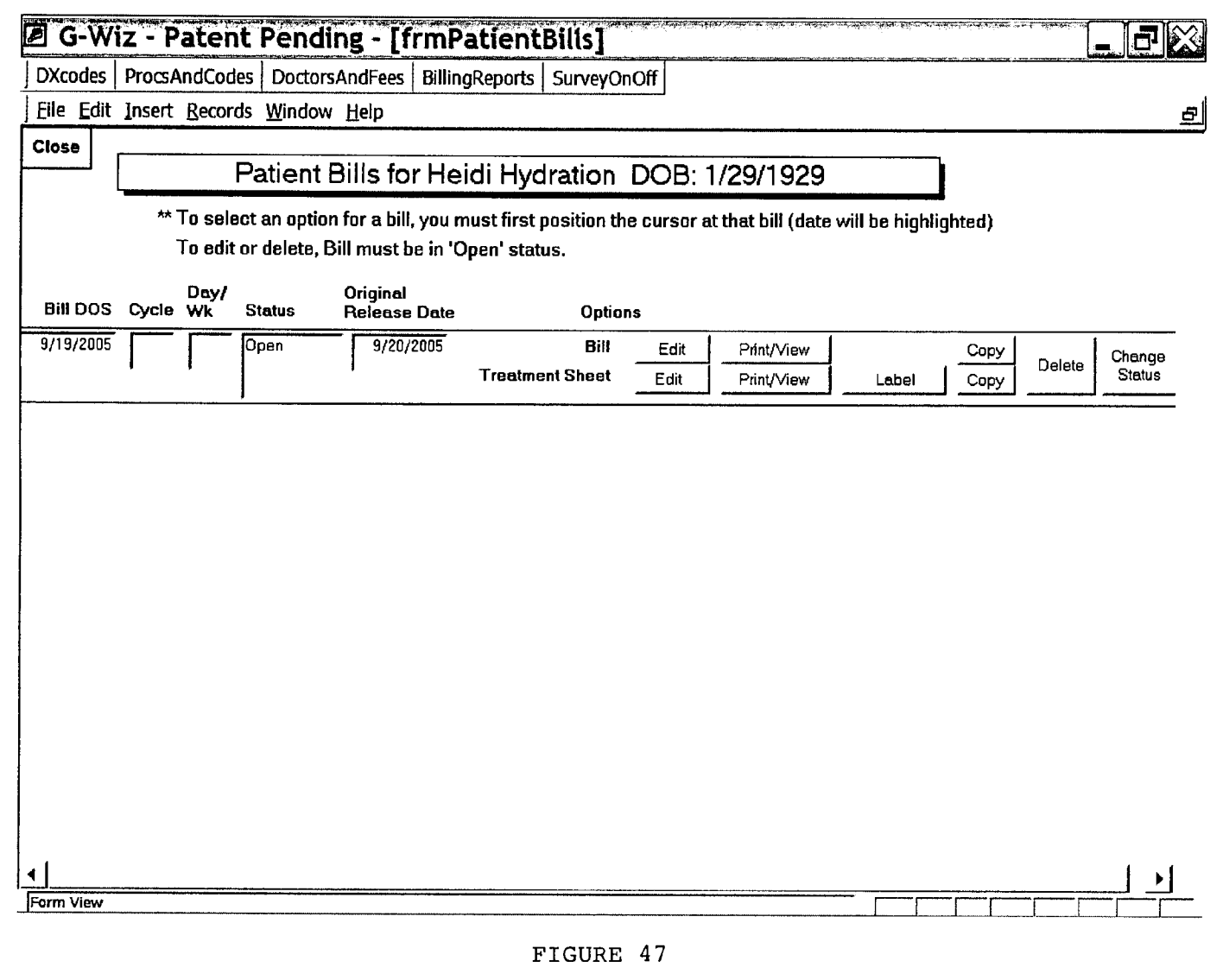

FIG. 47 shows the result of clicking Yes. Now the record has an Open Status. The Edit buttons will proceed to provide modifications to the encounter. Edit to the right of Bill under Options will offer View Superbill. Edit to the right of Treatment Sheet under Options will offer View Treatment Sheet.

Notice, the Original Release Date contains the date when the user first released the Superbill for billing. This serves as a flag to the biller that this Superbill could already be in the billing system. The biller will need to evaluate if any extra ordinary effort will be required to reconcile the practice's billing system. For example, the biller could have already transmitted the claim to the clearinghouse requiring rebilling.

Let's jump ahead where the application has already started another patient and the recording of information on the patient encounter is already in progress.

Figure 48:
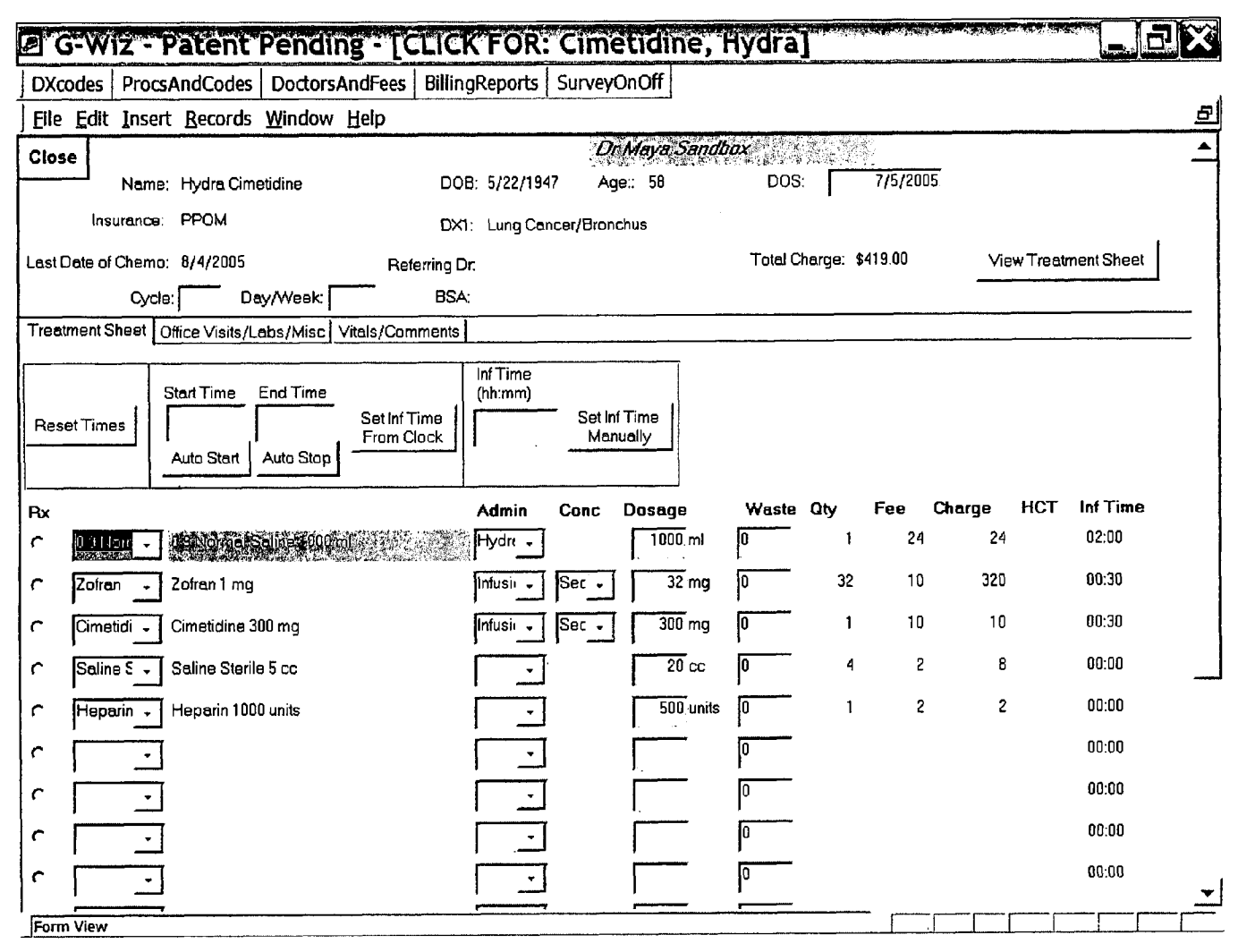

FIG. 48 shows treatment data for hydration, non-chemotherapy drugs, and fluids. This patient received a two-hour Hydration. To record this, the nurse selected 0.9 Normal Saline 1000 ml. Then the nurse changed the Admin from Dilutant to Hydration. This caused the Clock to appear, allowing the nurse to enter 02:00 into Inf Time. After the nurse clicked on Set Inf Time Manually, the application recorded 02:00 under Inf Time on the line containing the 1000 ml bag of Saline.

Next, the nurse reported the Zofran Infusion. The nurse entered 00:30 into Inf Time (hh:mm) and clicked on Set Inf Time Manually. As a result, Inf Time shows 00:30. The nurse made the same entries for the Cimetidine, resulting with 00:30 on its line.

The manufacturer packages both drugs in either Single-Use or Multiple-Dose vials. Therefore, the user has defined them in DrugsAndProcs as Multiple-Dose Vials. This prevents the application from attempting to estimate Waste. If Waste did occur, the nurse should enter the amount in the Waste field. When the packaging of the drug is consistently Single-Use, it behooves the practice to allow the application to estimate the waste. Because these two non-chemotherapy drugs were not administered Concurrent to each other, the nurse left the Conc fields at their default value of Sequential.

Finally, the patient's port was flushed with Heparin and Saline. In addition, the nurse selected Complete blood count in the Office Visits/Labs/Misc tab.

After the nurse clicked View Treatment Sheet, the prompt for Cycle-Day/Week appeared and the nurse elected not to make the entries.

Figure 49:
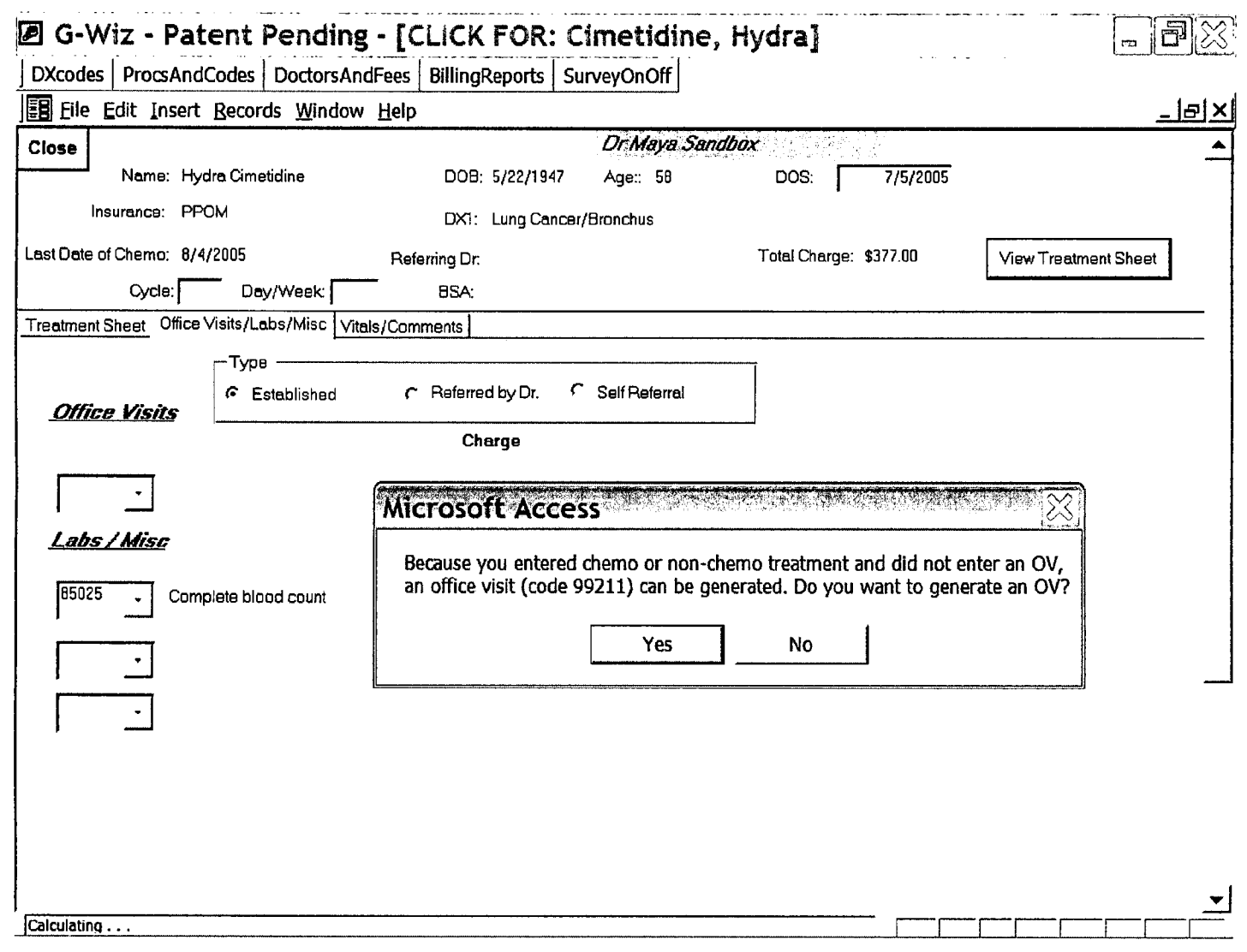

FIG. 49 shows a prompt for a 99211 Office Visit charge. Medicare will not reimburse for a 99211 if chemotherapy or non-chemotherapy was performed on the same Date of Service. Typically, 80% of an Oncology practice consists of Medicare patients. As a result, nurses often forget to charge for a 99211. Because the insurance for this patient is not Medicare, the application issues this reminder. The nurse can click Yes if she has met the requirements for billing a Level I Office Visit Brief. A confirmation, 99211 OV has been generated will appear next. After clicking Yes, the nurse declined the [ . . . peripheral IV . . . ] prompt.

Figure 50:
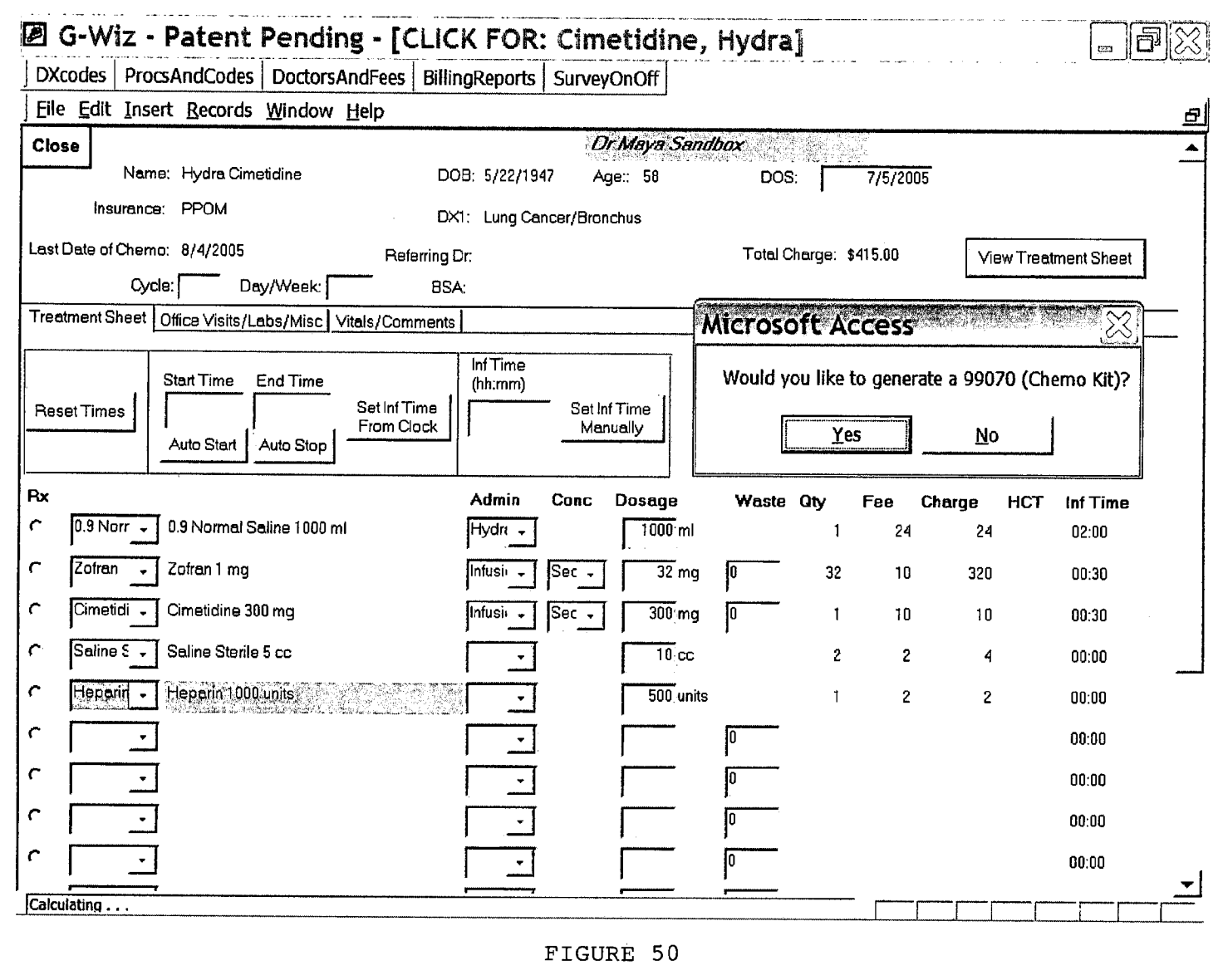

FIG. 50 shows a prompt to offering to bill a Chemo Kit to PPOM. Because the Insurance is PPOM rather than Blue Care Network, Blue Cross, Medicaid, or Medicare, the application offers a Chemo Kit as a billable expense. Had the insurance been Other, the application would have issued the same prompt, but with A4221. The nurse agreed to issue the charge by clicking on Yes.

Next, the Treatment Sheet appeared for review. Let's presume it is complete and the patient encounter is ready for billing. The nurse clicked Close and accepted [Save and submit to billing] and clicked Done.

Here is what the Superbill looks like:

FIG. 51 is a screen shot of the generated Superbill. The billing algorithm has parsed the Treatment data and determined Intravenous infusion, for therapy/diagnosis (specify substance or drug); initial up to one hour to be the Initial/Primary Procedure Code (Abbreviated as Initial hour IV infusion, non-chemo in ProcsAndCodes). Therefore, it appears on the first line of the first claim followed by the most expensive drug administered by non-chemo infusion, Zofran. From ProcsAndCodes, the billing algorithm knows that Zofran requires a secondary diagnosis code of 78701. The dosage for Zofran was 32 mg, which is a HCPS Billing Quantity of 32. Neither the application nor the nurse entered any waste value.

The patient received Cimetidine infused as a second non-chemotherapy drug. Thus, the billing algorithm generated, G0349, Intravenous infusion, for therapy/diagnosis (specify substance or drug); additional sequential infusion, up to one hour. The quantity for G0349 is one, but would be two is there was a third non-chemo drug infused. Following G0349 is the second infused non-chemo drug, Cimetidine, which requires a secondary diagnosis of 78701. Following this line are Remarks preceded by * * * . During data entry into the medical billing software, the biller should copy this string of characters into the Remarks box for the claim.

Cimetidine does not yet have its own unique J-Code. It is an Unspecified Drug with a shared J-Code of J3490. J3490 and J9999 drugs must appear with a HCPS Quantity of one. Billers must document them in the Remarks box of the claim with J3490 or J999 followed by Drug Name, Route, Amount Used (Dosage plus Waste), and the NDC Number. Because the user did provide an NDC Number for Cimetidine in ProcsAndCodes, the number does not appear in this example.

For J3490 and J9999 drugs, ProcsAndCodes provides for the entry of an NDC Number. For J3490 and J9999, the application generates the contents of Remarks as: * * * followed by either J3490 or J9999 followed by the Drug Name (As defined in ProcsAndCodes) followed by the Route of Administration followed by the Amount Used (Dosage plus Waste) followed by the NDC Number (Also, defined in ProcsAndCodes). The application displays the generated line after the line in the Superbill containing the J-Code with the HCPS Quantity equal to one.

Next, the application lists the G-Code for Hydration. Unlike the patient encounter for Heidi Hydration, Hydration is not the Primary Procedure for this patient. Thus, the application has issued a G0346, Intravenous infusion, hydration; each additional hour, up to eight (8) hours to correctly bill for Hydration. Because there was non-chemotherapy during this encounter, a 59 Modifier is required for the G0346.

Finally, we have the 99211 for the Nurse Charge. Because the patient received non-chemotherapy, a 25 Modifier must be included.

There are two claims for the biller to balance to during data entry. Claim #1 totals $619.00 and Claim #2 totals $120.00. The total for the encounter is $739.00.

Figure 52:
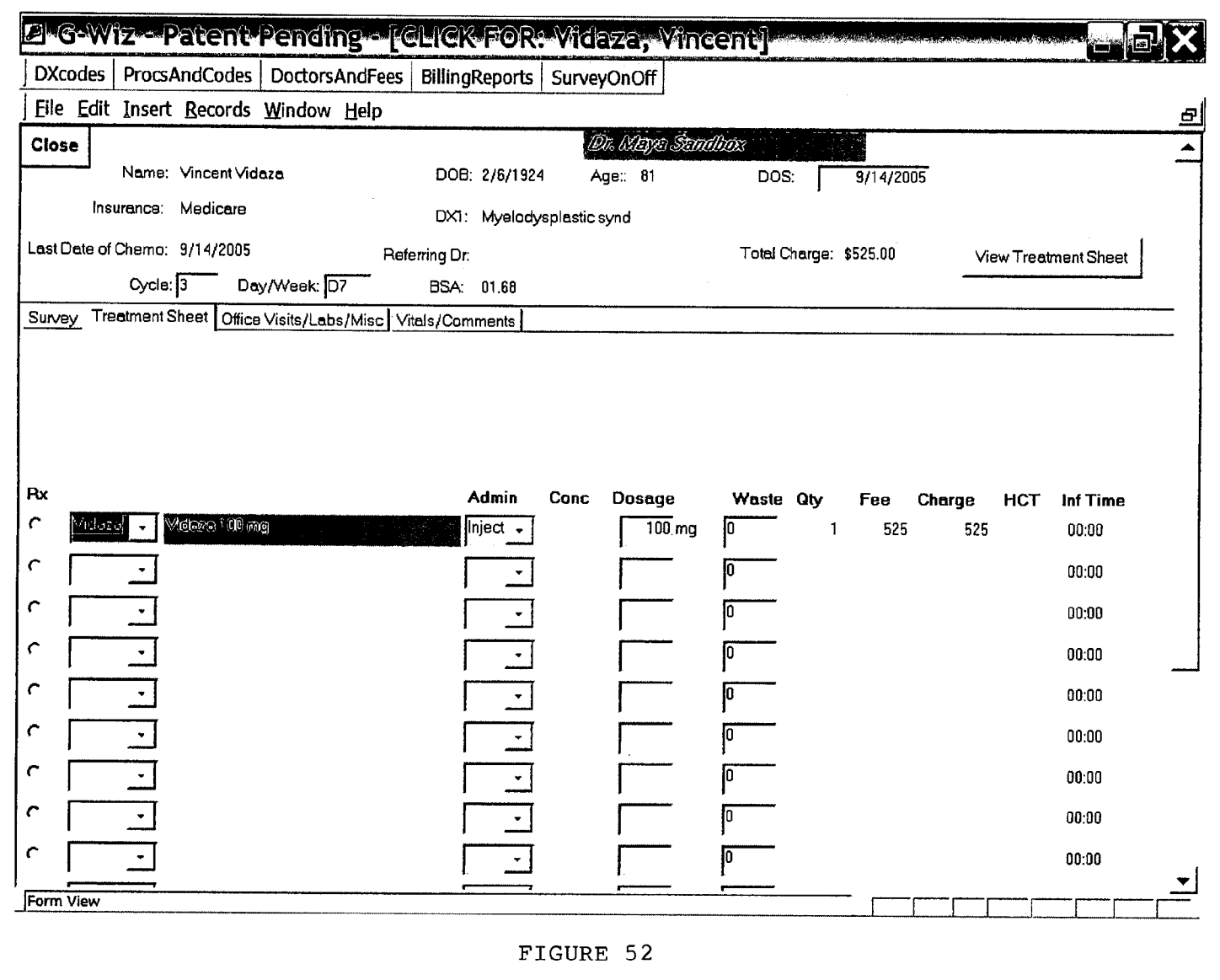

FIG. 52 shows the entry of treatment data for a J9999 non-hormonal injection. This is a very simple patient encounter illustrating that the user does not need to remember which drugs are hormonal versus non-hormonal. The patient received an injection of the chemotherapy drug Vidaza. It comes in 100 mg Single-Use Vidaza. The application has accurately estimated that there was zero waste during this treatment.

Figure 53:
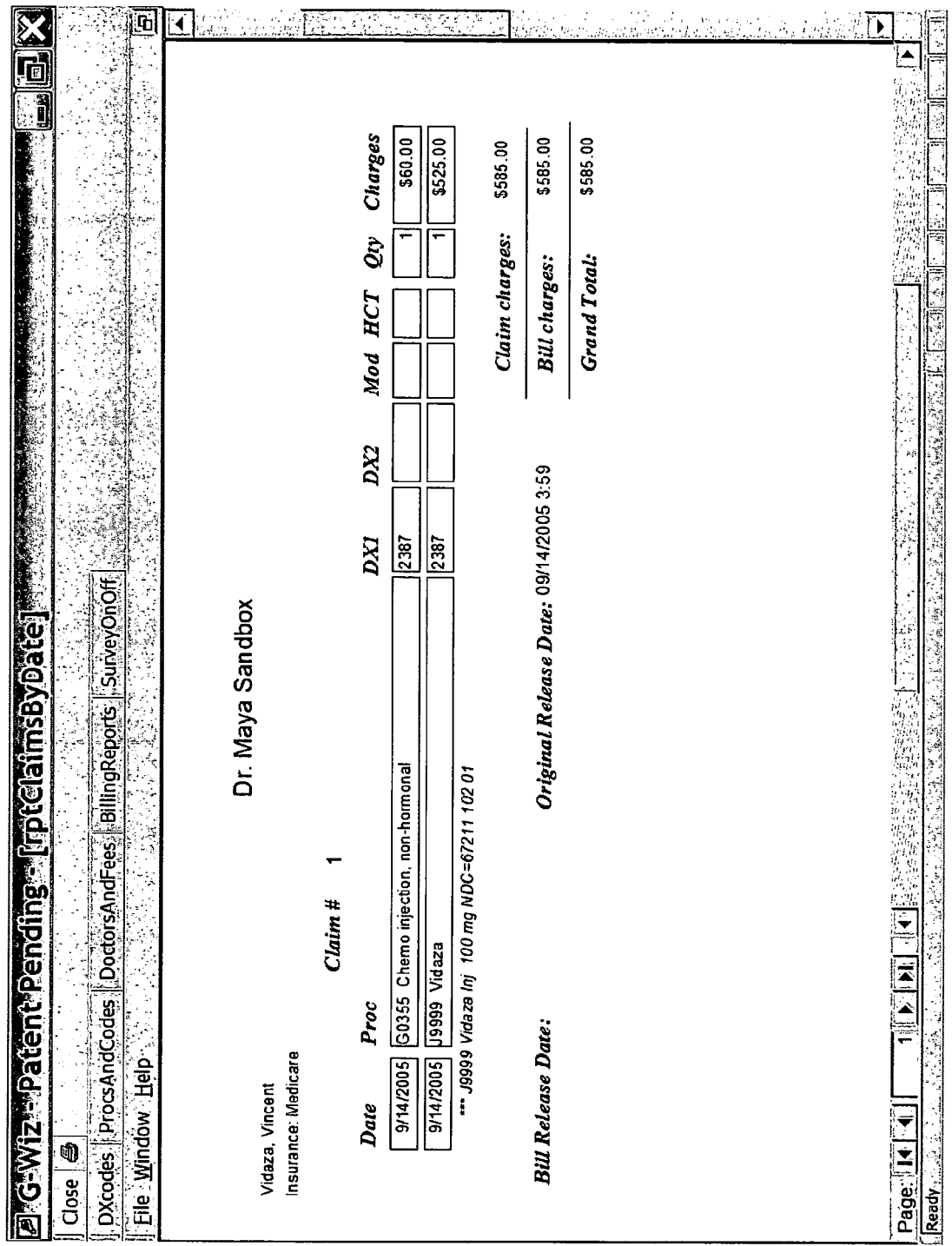

FIG. 53 is a screenshot of the generated Superbill. The application has listed the J9999 drug to convey the necessary information to the biller in order to document the Remarks correctly. The HCPS Quantity is one and the billing algorithm generated the necessary values for Remarks, listed in a format that works. There was zero waste during the administration. If there were waste, it would have been included in the total. The NDC Number has a defined value in ProcsAndCodes; so, it can appear here.

Notice, the billing algorithm generated G0355, Chemotherapy administration, subcutaneous or intramuscular; non-hormonal anti-neoplastic as opposed to G0356, Chemotherapy administration, subcutaneous or intramuscular; hormonal anti-neoplastic or G0351, Therapeutic or diagnostic injection (specify substance or drug); subcutaneous or intramuscular. In ProcsAndCodes, the user defines each drug (or saline) as Fluid, Chemo, or Non-Chemo with an administration type. For the Chemo drugs administered by injection, the user also specifies whether the drug is Hormonal or Non-Hormonal.

Figure 54:
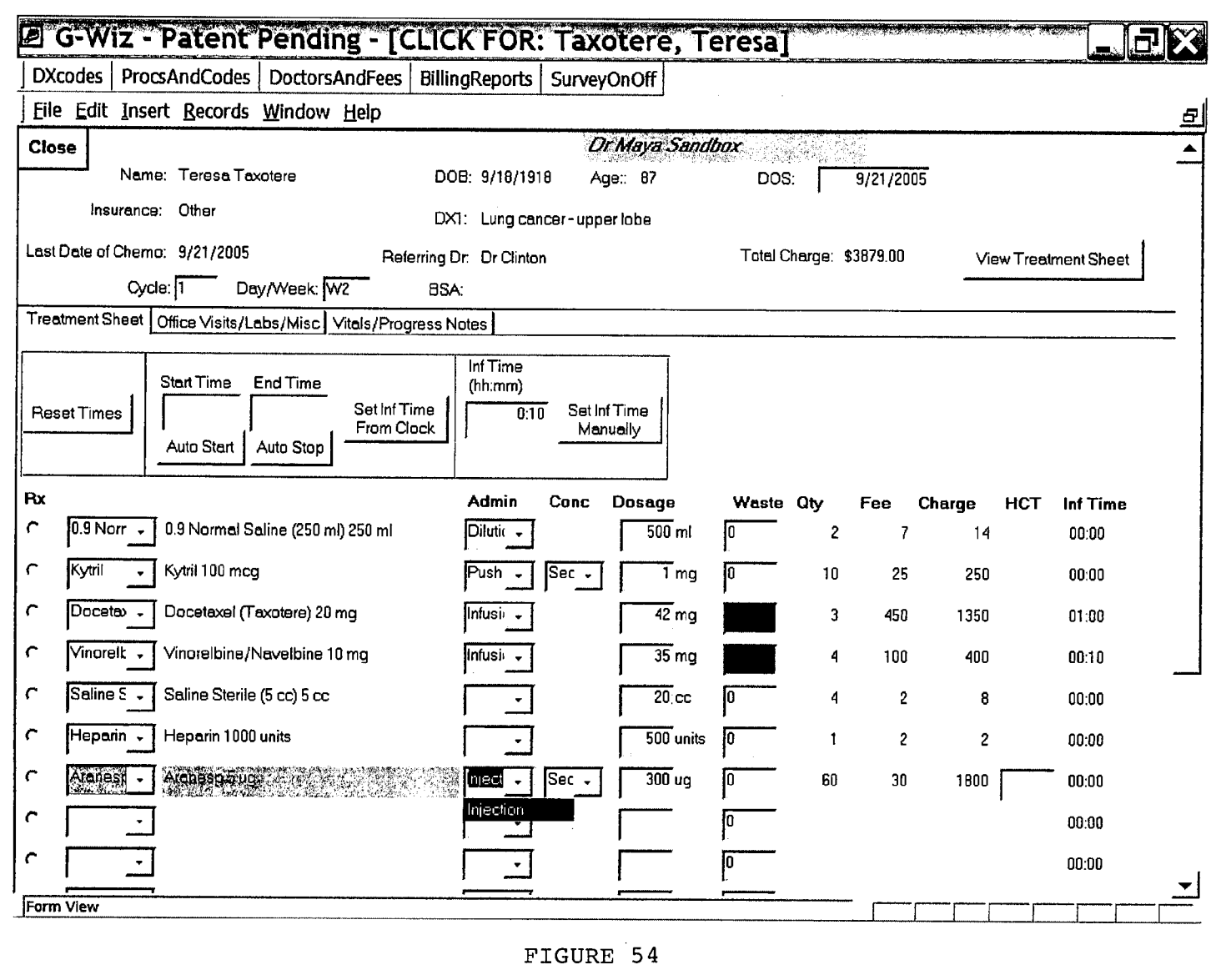

FIG. 54 shows the entry of treatment data for Taxotere to a patient with Other insurance. The nurse administered Kytril by a Push. Kytril comes in both Single-Use and Multiple-Dose vials. The user has defined it as Multiple-Dose in ProcsAndCodes. This precludes the application from estimating the waste, relying entirely upon the nurse for any value. The application allowed the nurse to enter the convenient dosage value of 1 mg and converted it to the HCPS Quantity of 10 billable units.

The nurse infused 42 mg of Taxotere for one hour. Taxotere comes in Single-Use vial sizes of 23.6 mg and 94.4 mg including overfill. The nurse dilutes them into injection concentrates of 20 and 80 mg, respectively. The practice has defined Taxotere as Single-Use in ProcsAndCodes. The application has estimated the Waste as 18 mg by assuming the vials size to be the same as the HCPS Billing Units. The nurse has an opportunity to modify this estimate, but has left it as is.

After the computer application obtains the ability to store vial sizes, it may make sense to avoid entering the vials sizes for Taxotere to avoid confusion resulting from Taxotere's use of overfill. For proper waste calculations, the stored vial sizes would have to be 20 and 80 mg rather than the actual package volumes of 23.6 and 94.4. Since, use of 80 mg concentrate is infrequent, it is probably easier to continue to use the HCPS Billing Unit as the estimate for vial size.

The nurse infused 35 mg of Vinorelbine for 10 minutes and received a warning. The ten minutes is the actual time; so, the nurse has left the time entry as it is.

Vinorelbine comes in 10 mg and 50 mg Single Use Vials. The nurse cannot use any remaining portion on another patient or encounter. The remainder is reimbursable when included in the billing quantity. Both vial sizes have the same J-Code (J9360) with a HCPS Billing Unit of 1 mg. The application estimates the Waste by presuming the vial size is the same as the HCPS Billing Unit. A HCPS Billing Unit of one will always result in a waste estimate of zero. The nurse has made an entry of 5 mg, which is the expected waste when 10 mg vials are used.

However, if the vial size were actually 50, the Waste would be 15 mg, a yielding a $100.00 increase to Charge of $400.00, again illustrating how important it is for the nurse to monitor this field. To improve the estimate of Waste, the program application provides the ability to select the drug by vial size. The application may automatically provide the entry of 5 mg of waste (not shown).

The patient received Aranesp. Because ProcAndCodes has Arenesp defined with an Administration type of Injection Only, the drop down box only offers Injection, reducing the possibility of a keystroke error. The practice has established the Arenesp Default Dosage in ProcAndCodes to 300, which the application has automatically entered into the Dosage field, resulting in a HCPS Billing Quantity of 60.

Aranesp comes in Single-Use vials in sizes of {25, 40, 60, 100, 150, 200, and 300} mcg. All use the same J-Code (J0880), which has a HCPS Billing Unit of five mcg. In this example, the user defined it as a Multiple-Dose vial in ProcsAndCodes, leaving any entry for waste entirely up to the nurse, who has left it blank. The future application enhancement to store vial size, would not likely by of much assistance, since the waste is usually going to be zero.

Because Aranesp requires the patient's HCT Level for reimbursement, a box to enter the value has appeared. Notice what happens if the nurse clicks on View Treatment Sheet and forgets to enter an HCT.

Figure 55:
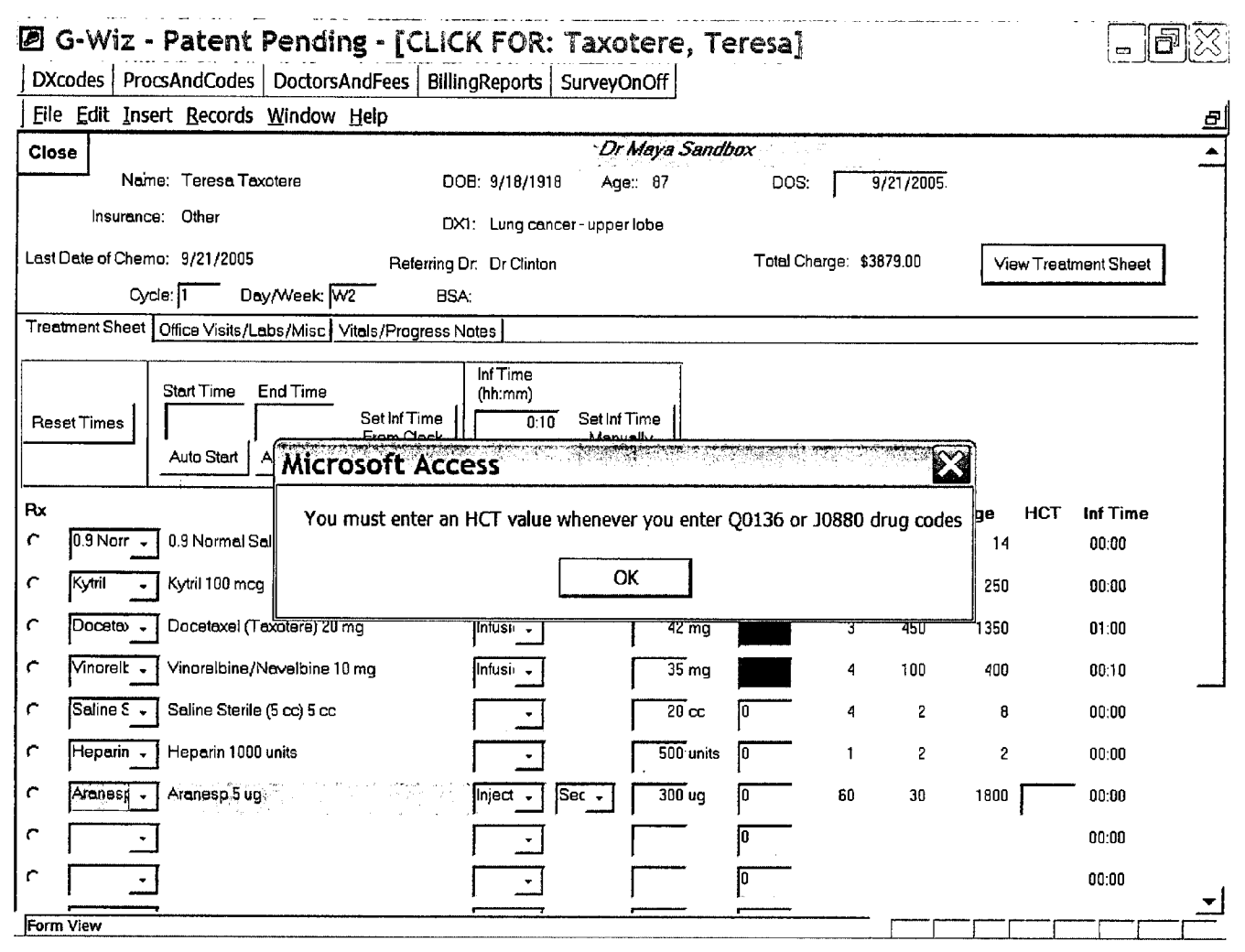

FIG. 55 shows the result of not entering a HCT value for a drug that requires one. Now see what happens if the nurse enters an HCT value that is too high.

Figure 56:
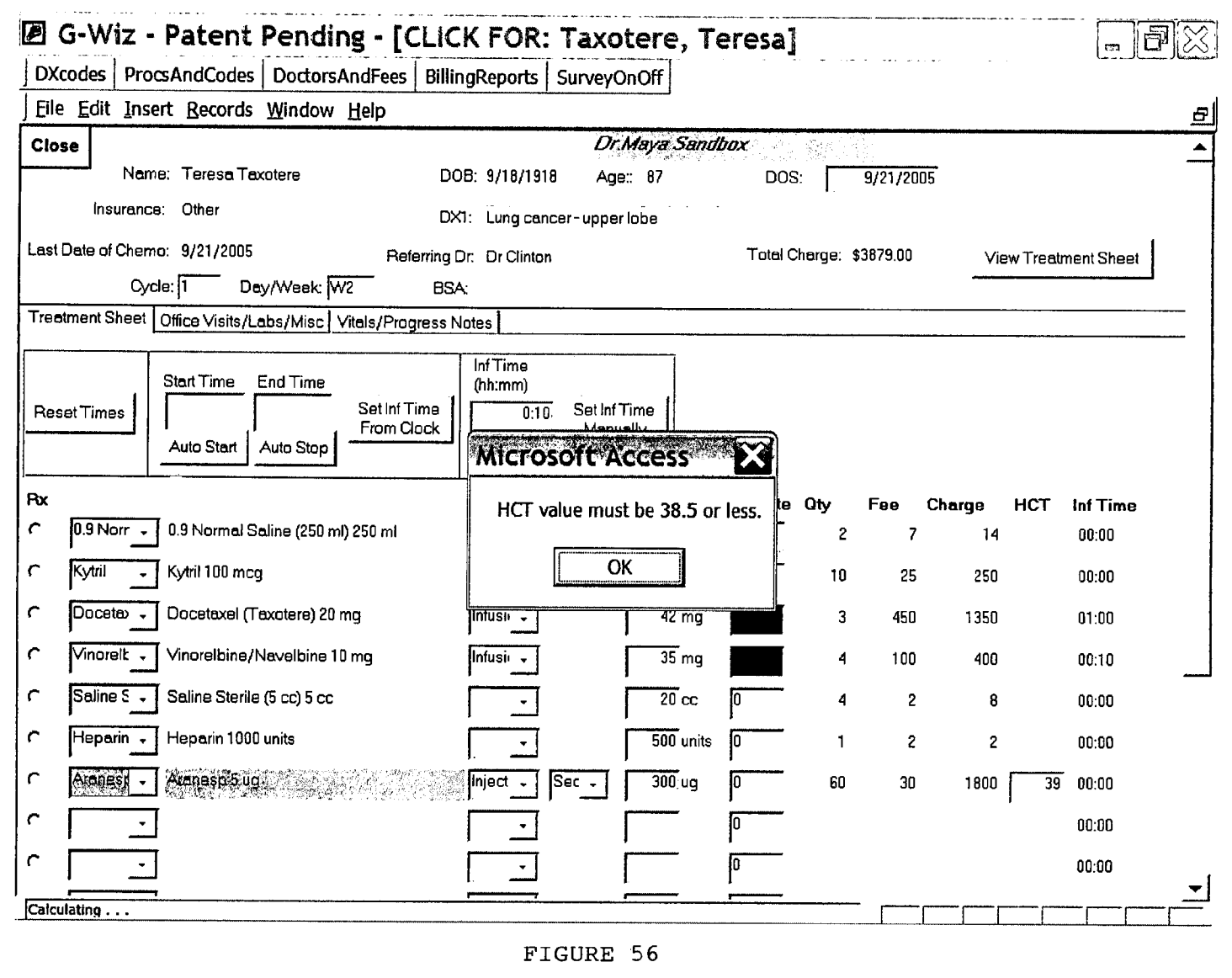

FIG. 56 shows the result of entering a HCT value that does not warrant reimbursement for the drug. The application notifies the user that the HCT Level does not warrant reimbursement. In real time, this could have prevented a loss. However, in this case, it was just an input error and the nurse corrects it. The nurse has already entered a Complete blood count in Office Visits/Labs/Misc. In addition, the nurse made entries in Vitals/Progress Notes. The nurse clicks on View Treatment Sheet.

Figure 57:
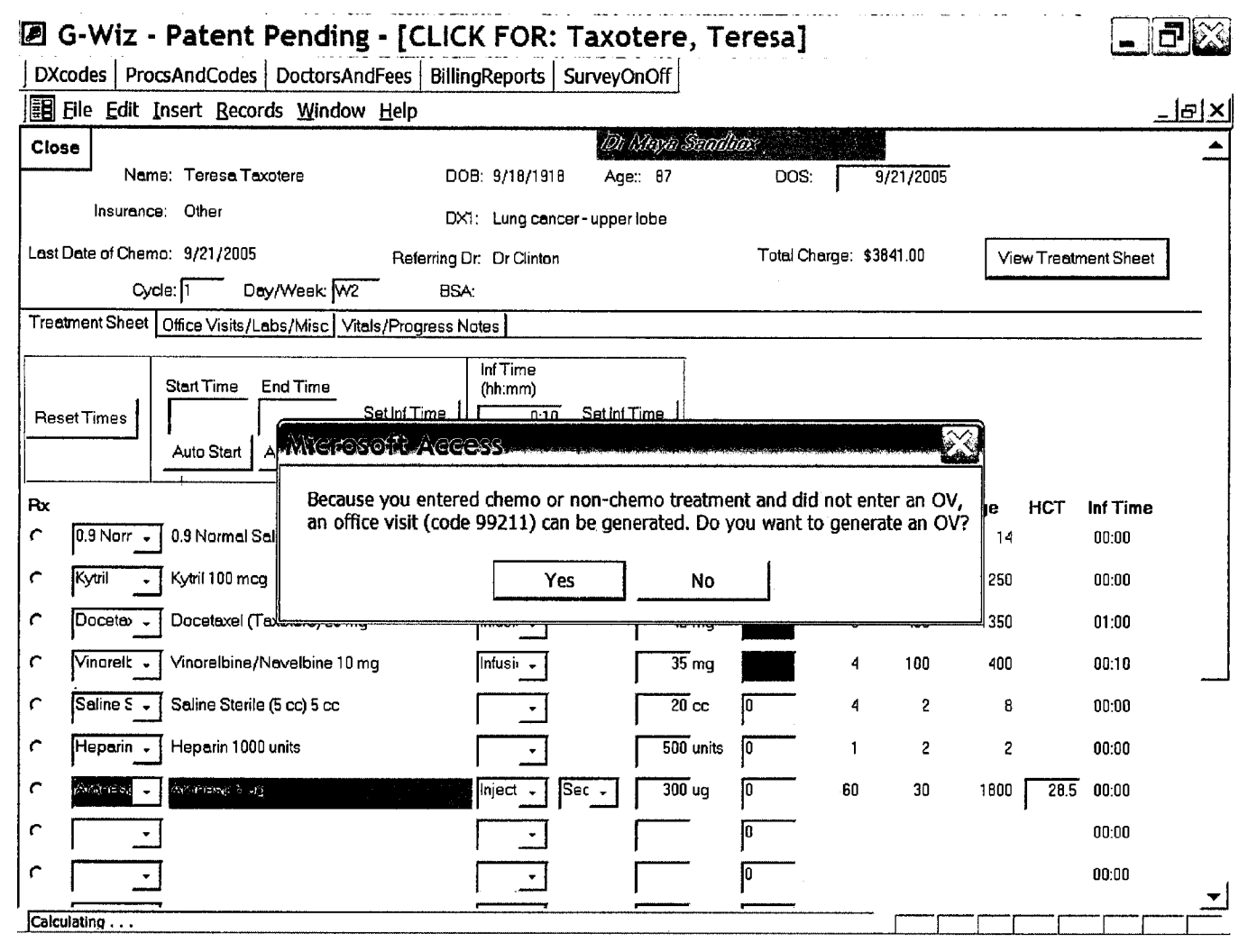

FIG. 57 shows a prompt offering to bill a 99211 Office Visit. The nurse spent considerable time education the patient, documenting this in the Progress Notes. However, because the practice is mostly comprised of Medicare patients, the nurse forgot that her time is billable because this patient has Other Insurance. The nurse clicks Yes.

Figure 58:
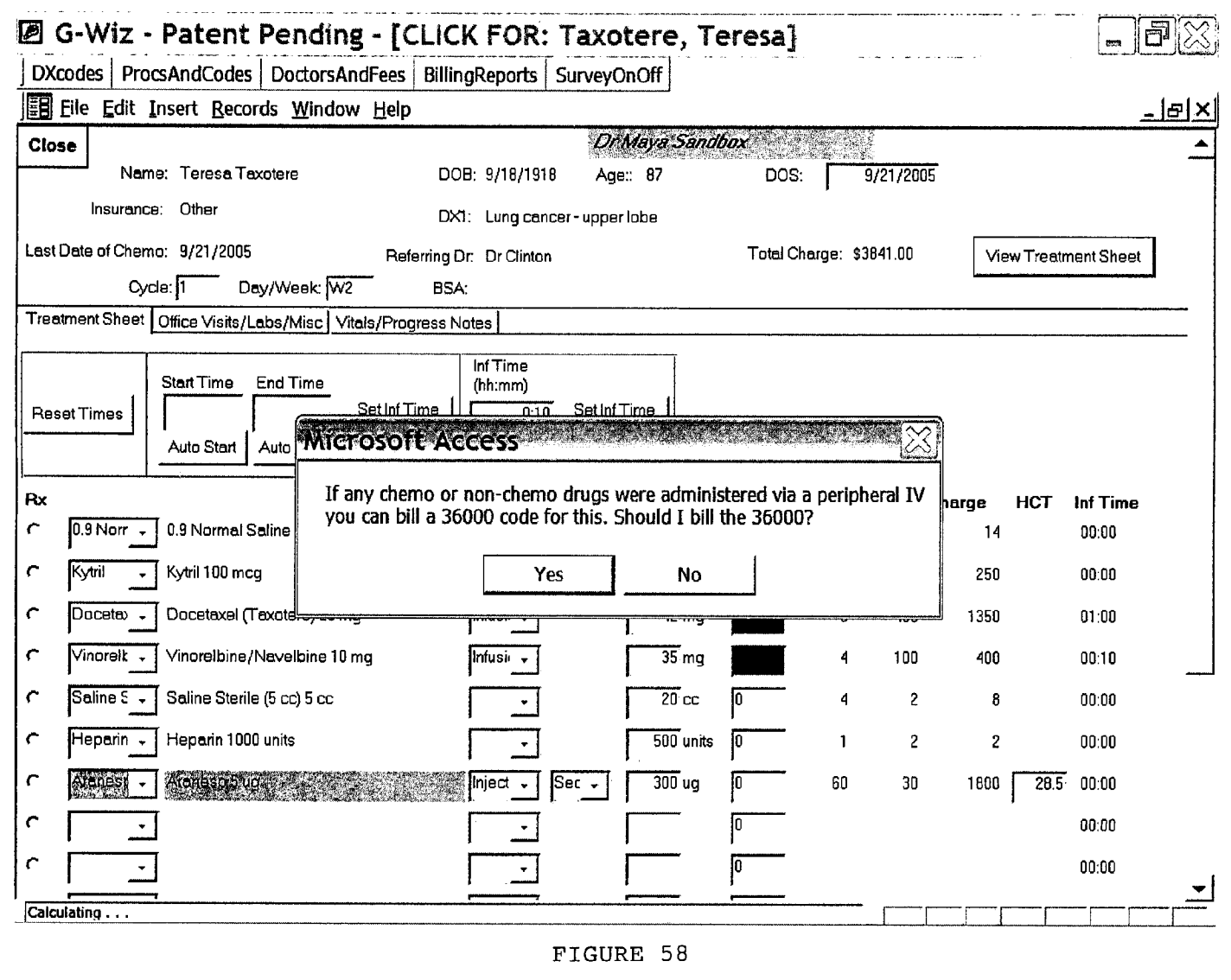

FIG. 58 shows a prompt querying whether the nurse used a Peripheral IV. The nurse clicks No.

Figure 59:
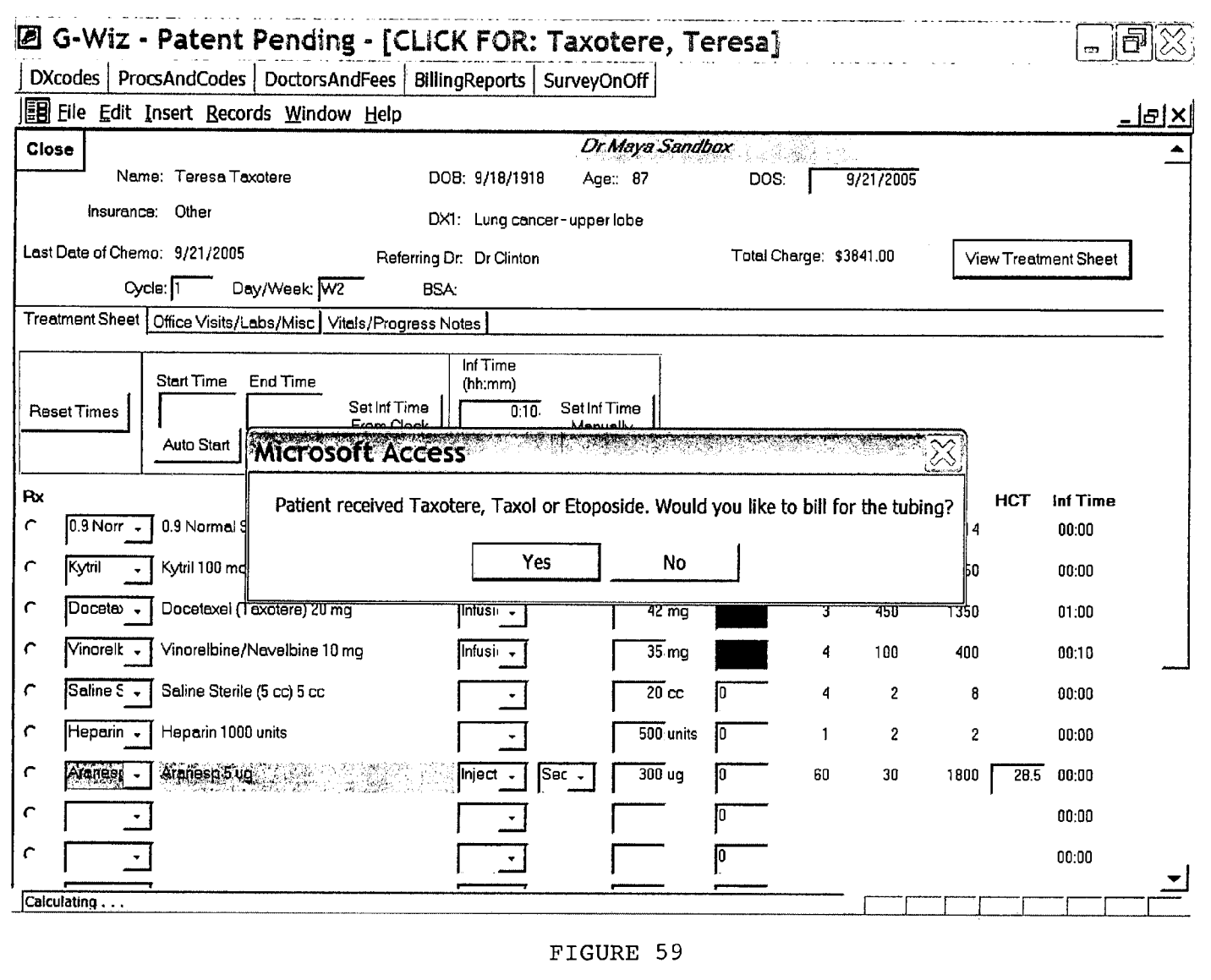

FIG. 59 shows a prompt offering to bill the special tubing. Because the patient received Taxotere and the insurance is Other, the special tubing is reimbursable. The nurse clicks, Yes.

Figure 60:
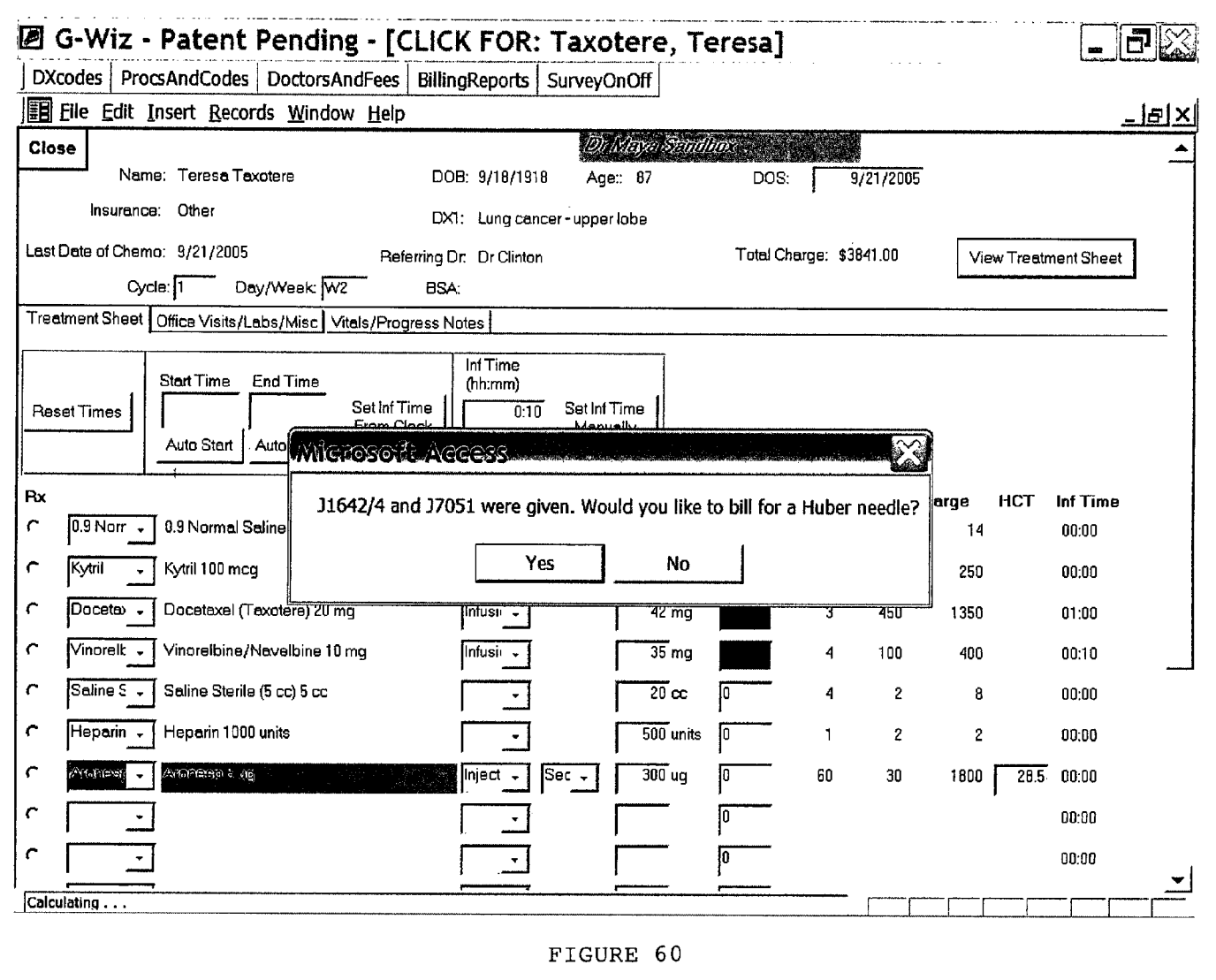

FIG. 60 shows a prompt offering to bill for a Huber Needle. The application has detected that the use of 5 cc of Saline with either Heparin or Heplock. This indicates that the nurse performed a Port Flush, expending a Huber Needle. Since the patient has Other Insurance, it is reimbursable. The nurse user clicks yes to bill this supply.

Figure 61:
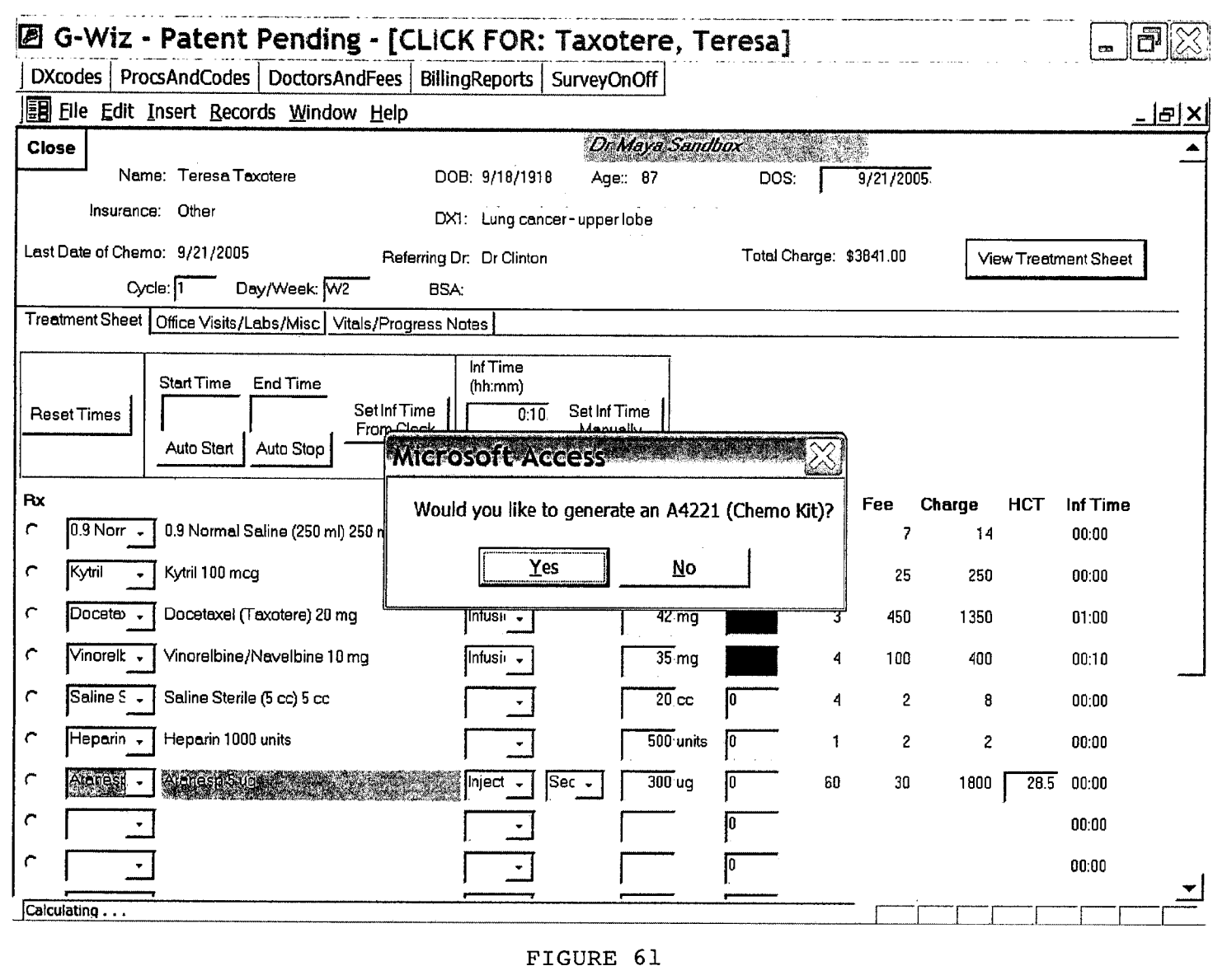

FIG. 61 shows a prompt offering to bill a Chemo Kit. Because the patient received an Infusion and has Other Insurance, a Chemo Kit is reimbursable. Therefore, the application issues this prompt. The nurse clicks Yes and then clicks View Treatment Sheet.

FIG. 62 shows the screenshot for the top half of the patient treatment sheet. Notice, both chemotherapy drugs have their calculated waste documented. The bottom half of the Treatment Sheet follows:

FIG. 63 shows the screenshot for the bottom half of the patient treatment sheet. After the nurse saves the Treatment Sheet, the Superbill is available for viewing.

FIG. 64 shows the screenshot for the top half of the Superbill. This bill has been broken up into two parts in order to paste it into this document. In Claim #1, we see G0359 for Chemotherapy administration, intravenous infusion technique; up to one hour, single or initial substance/drug. The billing algorithm has appropriately identified the chemotherapy infusion as the Primary Procedure for this encounter.

Taxotere (J9170) was the only chemotherapy drug administered by the infusion. The billing algorithm has placed J9170 immediately after its infusion code and calculated a HCPS Quantity of three.

Another chemotherapy administration occurred, not determined to be the Initial Procedure for the encounter. Therefore, the algorithm encoded it as G0358, Chemotherapy administration, intravenous; push technique, each additional substance/drug.

Because the patient received only one chemotherapy drug by a push, G0358 has a quantity of one. The administered drug, J9390, Vinorelbine immediately follows with a HCPS Billing Quantity of four.

Next the billing algorithm encoded G0354, Therapeutic or diagnostic injection (specify substance or drug); each additional sequential intravenous push. Since the nurse only pushed one non-chemotherapy drug, the quantity is one. The drug was Kytril (J1626) with a dosage of 0.1 mg, converted to a HCPS Billing Quantity of 10. Reimbursement for Kytril requires a secondary diagnosis code of 78701 (Nausea with Vomiting), which the billing algorithm obtained from ProcsAndCodes. The billing algorithm has filled all six lines of the first claim; so, it calculates the total. The Claim charges total of $2375.00 provides the biller with a number to balance to during data entry into the billing system.

Figure 65:
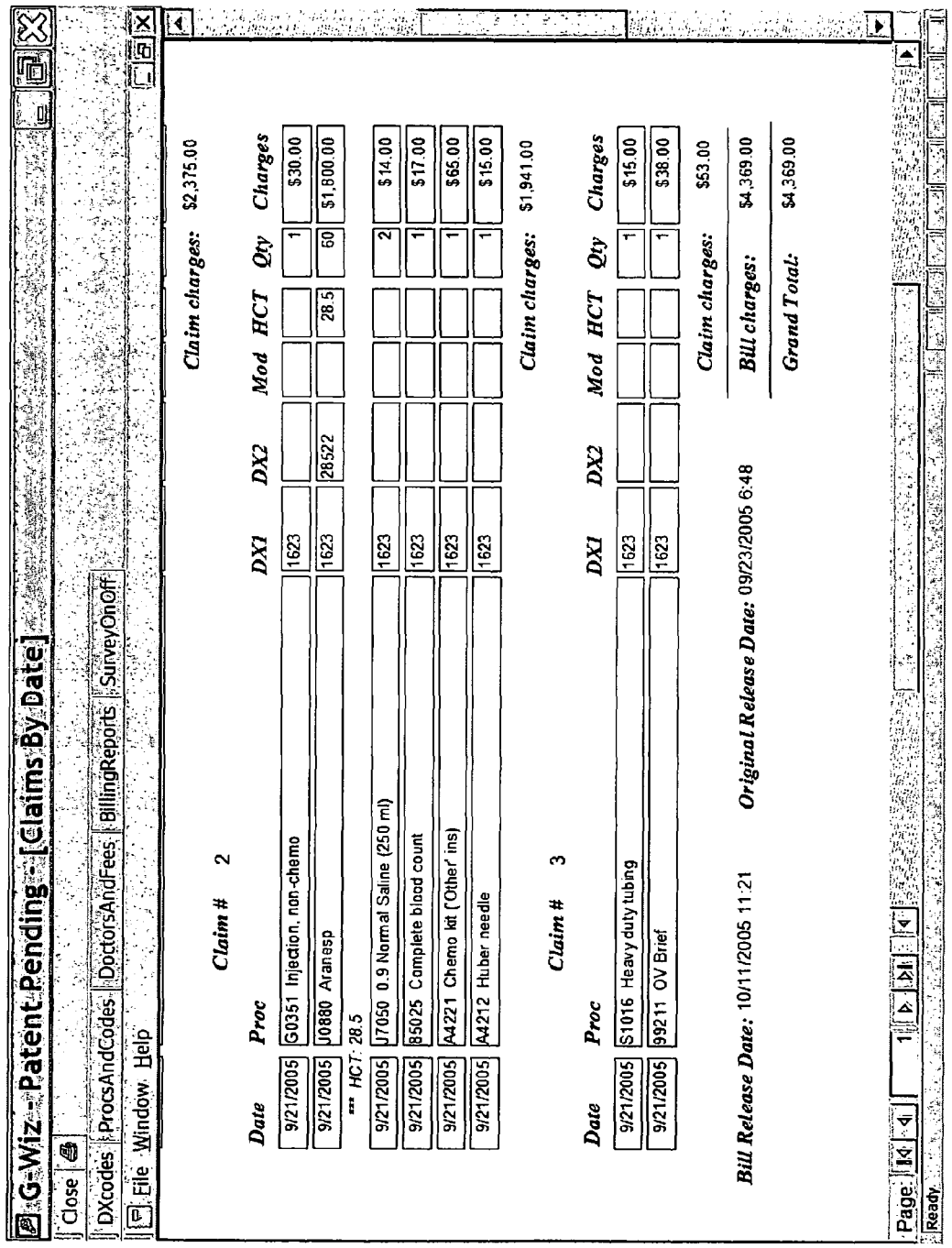

FIG. 65 shows the screenshot for the bottom half of the Superbill. In Claim #2, the first line is G0351 (Therapeutic or diagnostic injection (specify substance or drug); subcutaneous or intramuscular) for the non-chemotherapy drug Aranesp (J0880). The dosage is 300 ug, which the billing algorithm converted to a HCPS Billing Quantity of 60.

When the patient has a cancer diagnosis (1623 in this case), a secondary diagnosis code of 28522 (Anemia in Neoplastic Disease) is required for reimbursement. The HCT column of the claim must indicate an HCT value less of 38.5 or less. In addition, the Remarks section of the claim must also indicate the HCT value. The application flags this with a line beginning with * * *.

Left remaining for the billing algorithm to bill is only supplies, a laboratory procedure, and an Office Visit. Order for these items is not important. Thus, the algorithm fills the remaining lines in Claim #2 and calculates the Claim charges total to be $1,941.00.

The billing algorithm generates a third claim to accommodate the last two items. A Grand Total for the entire encounter is also calculated ($4,369.00).

Figure 66:
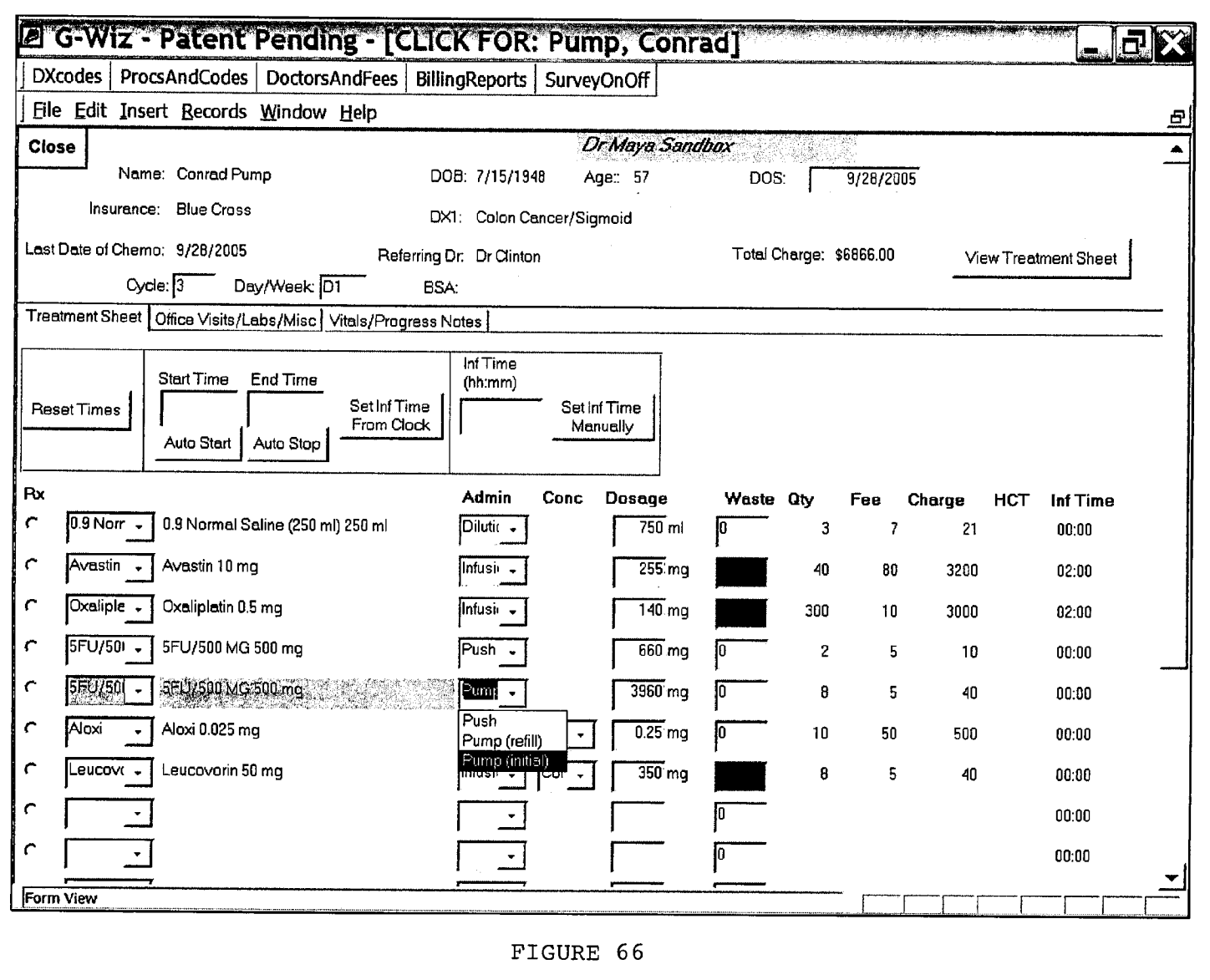

FIG. 66 shows the entry of treatment data related to a pump. The nurse infused 255 mg of Avastin for two hours. Avastin comes in 100 mg and 400 Single-Use vials. The application estimated the waste by assuming the HCPS Billing Unit to be the vial size. Since, the HCPS Billing Unit is only 10 mg, the application vastly underestimated the waste as 5 mg. The nurse actually dispensed the drug from a 400 mg vial, resulting in the true waste to be 145 mg. Had the nurse not entered the correct waste, the charge would have been $1400.00 less.

The application also has the ability to store the vial sizes with the drug in ProcAndCodes, which allows the nurse to select Avastin with the vial size, resulting in the correct calculation of waste.

The nurse also infused 140 mg of Oxaliplatin for two hours. Oxaliplatin comes in 50 mg and 100 mg Single-Use vials. Both vials have the same J-Code (J9263) with a HCPS Billing Quantity of 0.5 mg. Using the HCPS Billing Unit as the presumed vial size, the application estimated zero waste. The nurse has entered the correct waste amount of 10 mg, resulting in additional charge of $200.

The application also has the ability to store the vials sizes with the drug in ProcsAndCodes, which allows the nurse to select the drug with the 50 mg vial size, resulting in the correct value for waste.

This encounter involves the Initiation of a pump. The 5FU definitions in ProcsAndCodes provide for 5FU to have Pump (refill) and Pump (initial) in its drop down box. In addition, in ProcsAndCodes, 5FU is marked for Multiple entries allowed. The nurse was able to record the push of 660 mg of 5FU followed by a pump Initiation with 3960 mg of 5FU. The use has defined 5FU in ProcsAndCodes as a Multiple-Dose drug. Thus, the application does not attempt to estimate any waste, relying entirely upon the nurse for any value.

FIG. 67 continues the illustration of the patient treatment, which involves a chemo pump. The nurse pushed Aloxi. The application converted the convenient dosage entry of 0.25 mg to the HCPCS Billing Units of 0.025 mg, resulting in a HCPS Billing Quantity of 10. Aloxi comes in a 0.25 mg Single-Use vial. Obviously, this resulted in zero waste.

Finally, the nurse infused 350 mg of Leucovorin Concurrently with the other infusions. Thus, there is no entry of time against Leucovorin. Leucovorin come in 50, 100, and 200 mg Single Use vials. In this example, the user has defined Leucovorin as a Multiple-Dose drug, resulting in no attempt by the application to estimate the waste. The nurse has entered a waste value of 50 mg, which the application used in the calculation of the HCPS Billing Quantity.

After the nurse clicks on View Treatment Sheet, a prompt appears.

Figure 68:
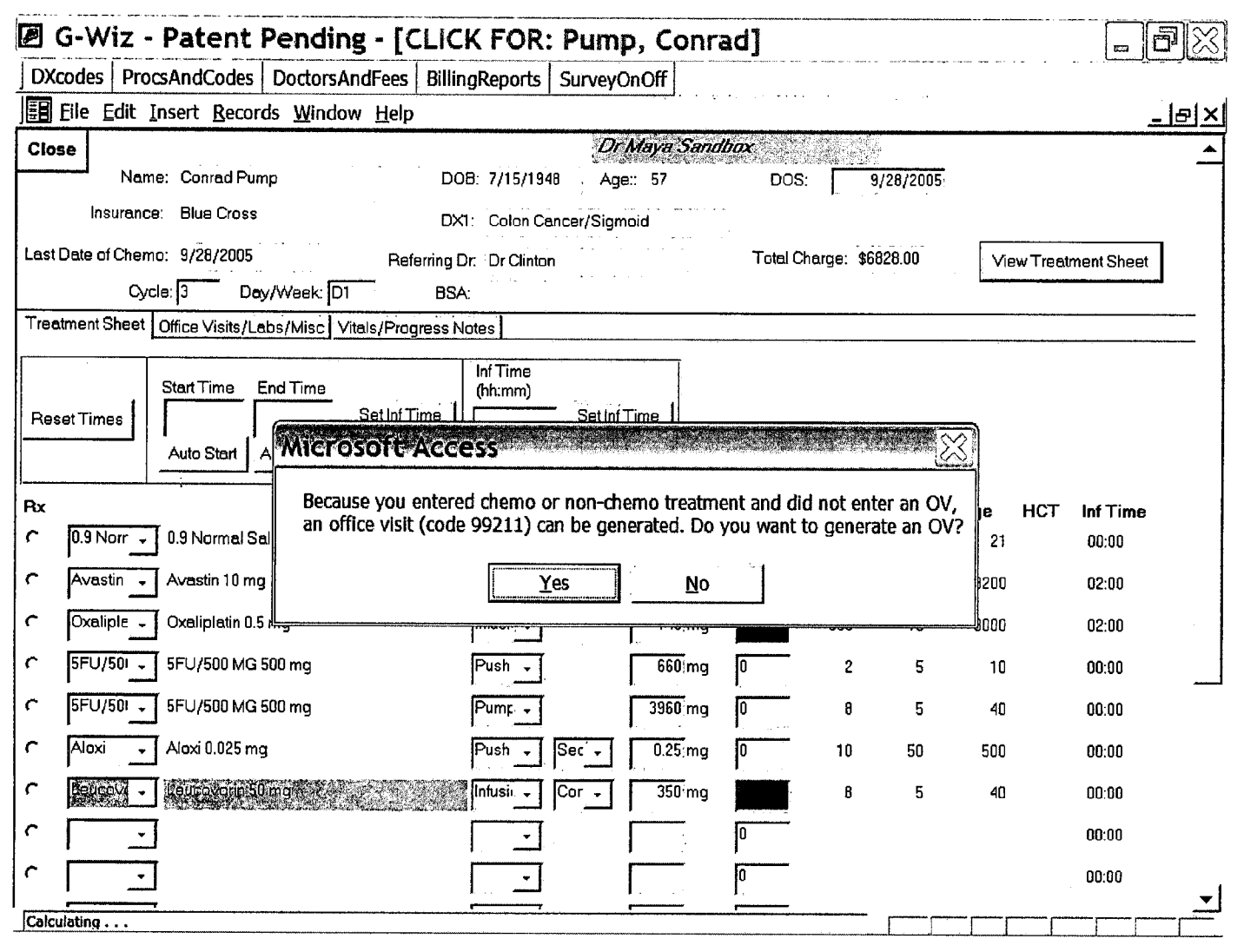

FIG. 68 shows a prompt for a 99211 Office Visit. Because the patient has Blue Cross, the nurse can bill for a Level I Office Visit. The nurse clicks Yes.

Figure 69:
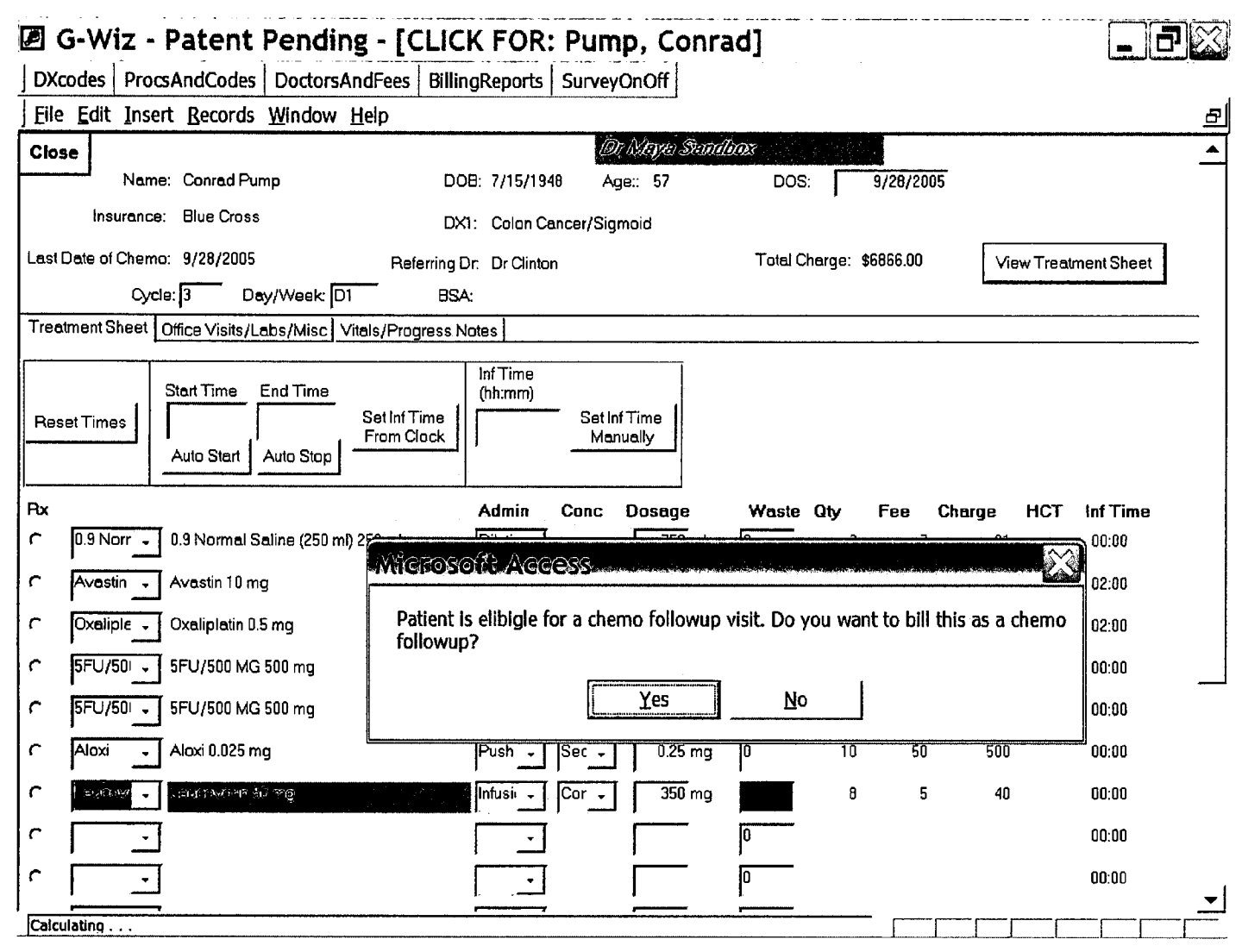

FIG. 69 shows a prompt offering to bill any Office Visit during this for the Date of Service as a chemo follow up visit. The patient has Blue Cross and the application has been keeping track of the Chemo Follow-UP Visits and has determined that the patient is eligible for such a visit, avoiding a co-payment from the patient; so, this prompt appears. The nurse clicks Yes.

Figure 70:
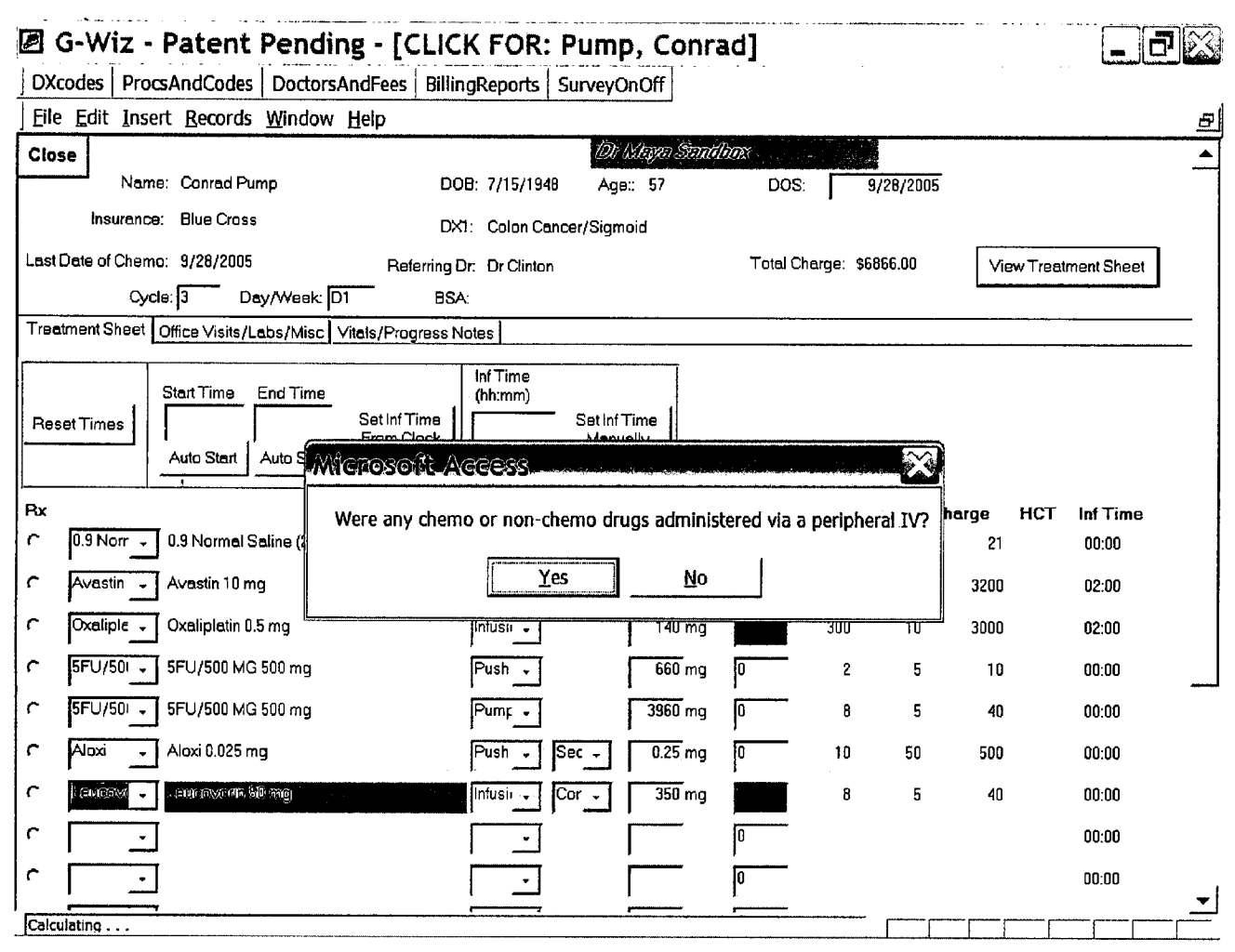

FIG. 70 is the prompt regarding a Peripheral IV that perpetually appears. The nurse clicks No.

FIG. 71 is a screenshot for the top half of the treatment sheet generated by the application. One can see the Progress Notes and Vitals entered by the nurse, which was presented among the previous screens. Notice that the Leucovorin has been labeled as a Concurrent Infusion.

FIG. 72 is a screenshot for the top half of the Superbill. The algorithm has identified the Chemotherapy Infusion as the Initial/Primary Procedure Code; so it appears on the very first line of the first claim. This is not to be confused with the pump Initialization, which is not an Initial Code.

There were four hours of chemotherapy infusion. The G0359 accounts for the first hour. The G0362 accounts for another hour and the G0360 accounts for the remaining two hours. The G0360 immediately follows the G0359 and immediately precedes the most expensive infused chemotherapy drug (Avastin) in the first claim. Since, Blue Cross requires Saline supplies to accompany the Initial/Primary Procedure, they also must appear in the first claim. The Initialization of the pump is in the last line of the first claim.

Claim #2 line starts with the G0362 with an accompanying chemotherapy infused drug (J9263). Next is G0358 for the Chemotherapy Push Technique followed by the pushed chemotherapy drug (J9190). The J9190 HCPCS Quantity includes the 5FU that went into the pump. At the end of Claim #2 is the non-chemotherapy concurrent infusion (G0350) followed by the infused non-chemotherapy drug (J0640).

FIG. 73 is a screenshot for the bottom half of the Superbill. Claim #3 starts with a non-chemotherapy push (G0354) followed by the pushed non-chemotherapy drug (J2469). The secondary diagnosis code 78701 (Nausea with vomiting) appears because it is required for reimbursement. The billing algorithm converted the Aloxi dosage to the HCPCS Billing Quantity of 10. The nurse also did a Complete Blood Count and the Nurse Office Visit follows with a V672 Primary Diagnosis code to signal to Blue Cross that this is a Chemo Follow-Up Visit with no co-payment to the patient. Blue Cross requires the Remarks for the Chemo Follow-Up Visit to state the Last Date of Chemo.

Figure 74:
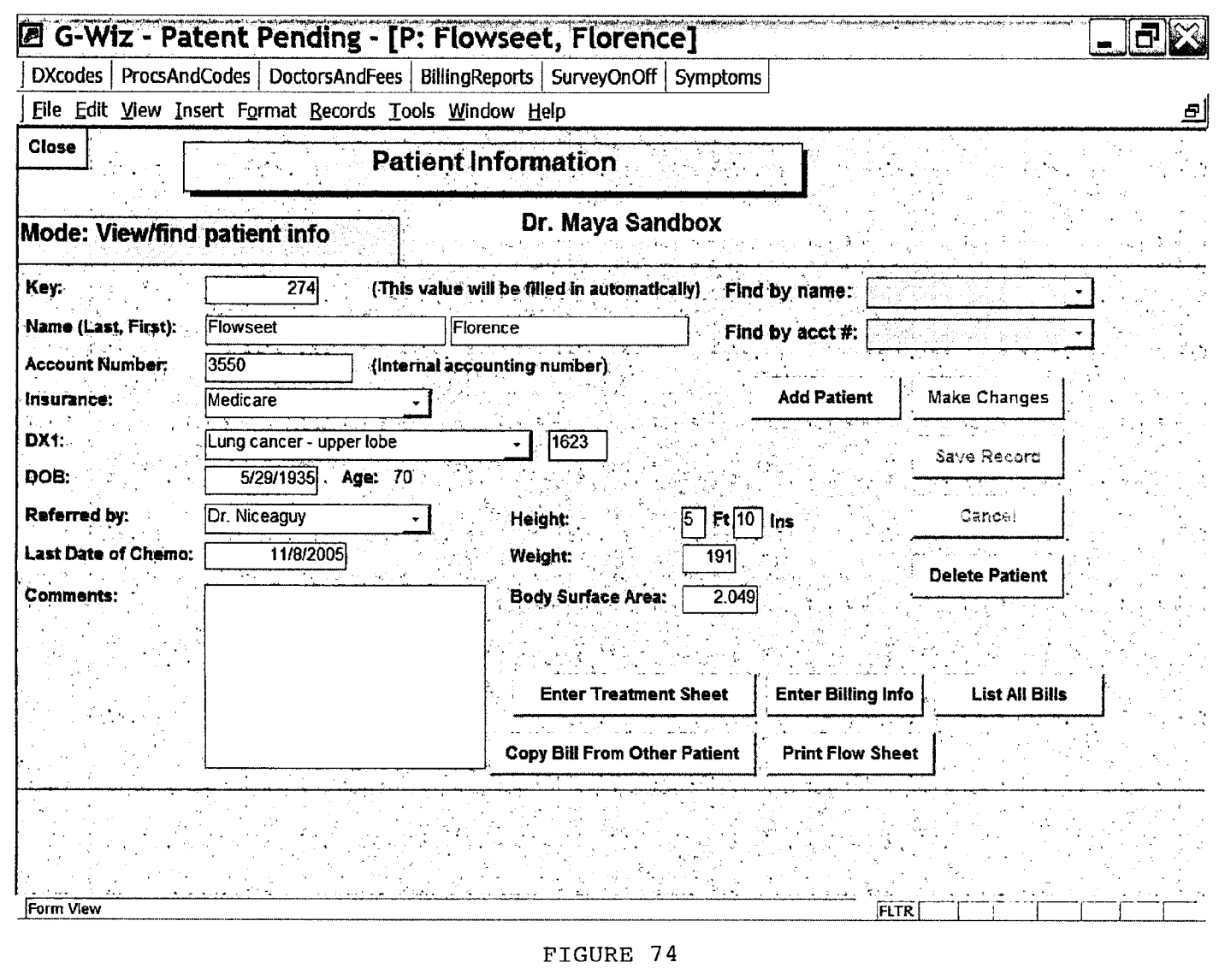

Referring now to the screenshot of FIG. 74, this version of the computer application has the Automated Flow Sheet feature. Notice there is a Print Flow Sheet button. First, let us look at the tabs in Enter Treatment Sheet for this version of the computer application.

Figure 75:
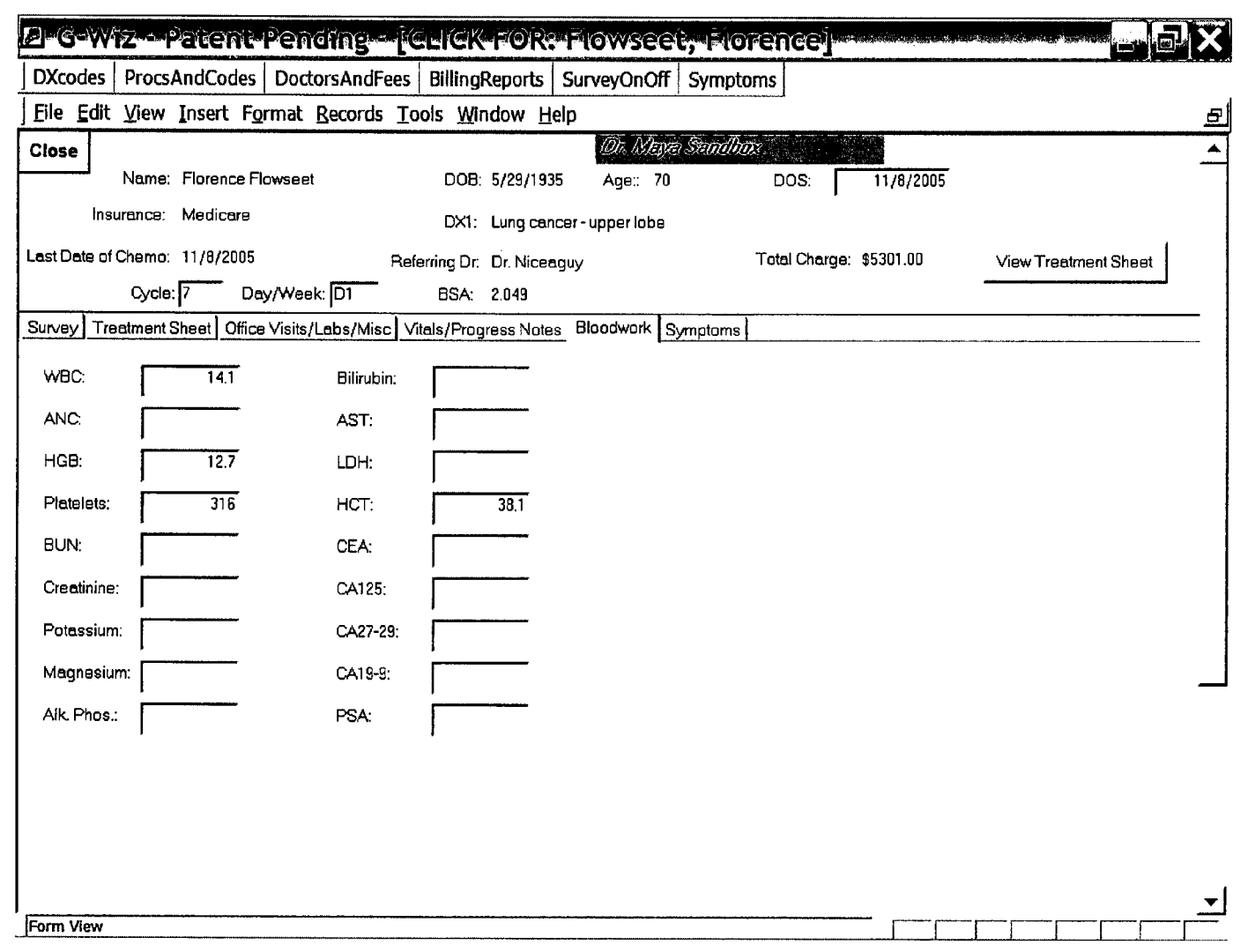

Referring now to the screenshot of FIG. 75, notice there are two additional tabs in this version of the computer application, Blood Work and Symptoms. Here in the Blood Work Tab, the user has made some entries.

Figure 76:
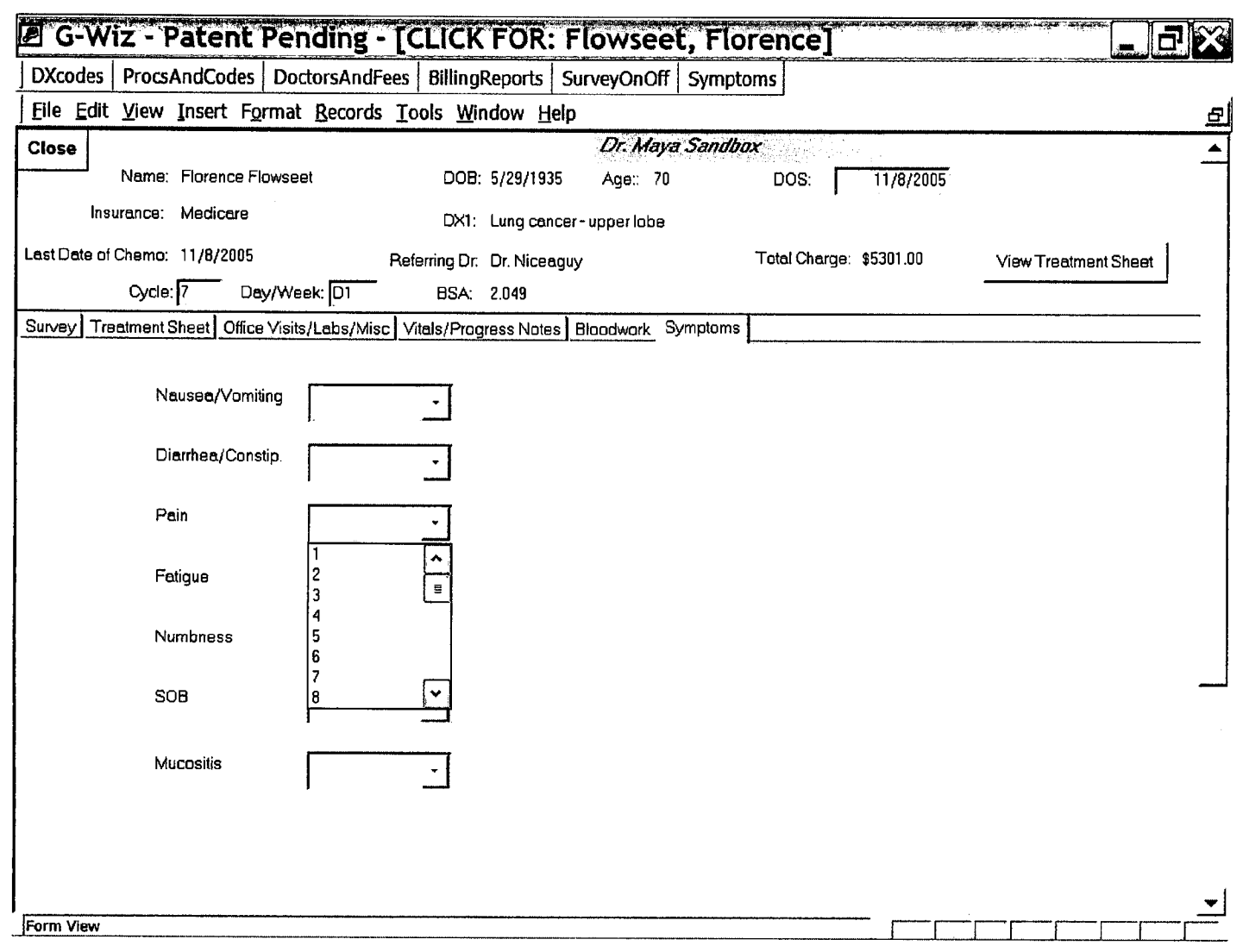

Referring now to the screenshot of FIG. 76, here is what the Symptoms Tab looks like. The drop down box for Pain illustrates some values the user has defined through the Symptoms Tab at the top of the screen. For this example, the user has not entered any reported symptoms. After returning to the Patient Information Window and clicking on View Flow Sheet, the following appears.

Referring now to the screenshot of FIG. 77, the computer application has listed the patient's dates of service, which the user can individually click. The Cycle and Day/Wk serve as a guide to indicate which treatments would be of interest to appear on the Flow Sheet.

Referring now to the screenshot of FIG. 78, here the user has selected all of the dates of service. After selecting the desired entries, the user can see the Flow Sheet results by clicking on View.

Referring now to the screenshot of FIG. 79, here is the resulting Flow Sheet. For the selected Dates of Service, the computer application displays the patient's Vitals and Symptoms, as well as any recorded blood work results. In this case, the user only entered blood work for the last Date of Service and did not enter any Symptoms for any day.

Summary

A purpose of this computer application is to collect chemotherapy treatment data on a particular patient for a specific date of service from an oncology nurse in order to generate a superbill. The computer application records the information and formats it, automating patient charting to assist the nurse. Then the application translates the administered drug and procedure data into a robust superbill, comprised of the most effective combinations of medical reimbursement codes to serve as input to medical billing software. The application performs this in a manner to improve the productivity and efficiency of the nursing and billing staff, while maximizing insurance reimbursement and expediting cash flow.

Functions of the computer application are to collect the minimum amount of billing data from the chemotherapy nurse at the time of treatment while maximizing revenue, then parse, and encode the data into sets of medical insurance claim lines heuristically proven to yield prompt and maximum reimbursement.

Secondary functions of the computer application are to encourage the use of the application by automating the record keeping and documentation of patient treatment data.

While the computer application currently generates claims using the Medicare G-Codes, it is able to accommodate any other system of insurance codes. The American Medical Association and Medicare have defined new CPT Codes, which the application is able to handle.

Benefits

1. It eliminates the necessity of the nurse to generate a superbill. The nurse does not need to learn coding rules and nomenclature. It insulates the nurse from bureaucratic changes to Medicare and other insurances.
2. It provides a framework for the efficient recording of patient treatment data, minimizing the amount of data recorded by the nurse, but assuring the billing of all reimbursable items.

3. It automates bill documentation and patient charting, saving hours of nurse time.
4. It is self-auditing. It continuously issues prompts and queries, while checking and validating entries. It is insists upon required documentation.
5. It eliminates the need for billing personnel to master the parsing of insurance codes. Changes to encoding procedures are implemented instantly, avoiding errors associated with going through a new learning curve and the breaking of obsolete billing habits. With the saved encoding time, the biller can spend more time reducing the outstanding accounts receivable.
6. It constructs insurance claim lines optimized to facilitate immediate approval by insurance adjudicators in order to expedite cash flow and to decelerate the growth of outstanding items in the accounts receivable.
7. It offers reimbursable items to the user on an insurance basis for charges not generally known to be reimbursable.
8. It builds an extremely robust superbill; such that, personnel with limited billing expertise can merely copy the claim lines into the doctor's billing software. Thus, it provides back up for the billing staff in order to facilitate vacation and sick time, without incurring an interruption in the billing pipeline. The application can greatly enhance billing software products that provide interfaces to accept the output of this application as direct input, eliminating manual data entry.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A computerized method for generating an electronic bill having optimized insurance claim items based on an insurance carrier of a patient, the method comprising:
    receiving via a user interface insurance carrier data which identifies a patient's insurance carrier and patient data which identifies a patient;
    receiving via the user interface treatment data which identifies at least one drug including a chemotherapy drug administered to the patient and at least one type of administration used to administer the at least one drug to the patient on a date of service;
    displaying via the user interface a prompt offering to bill an additional expense item eligible for reimbursement based on a comparison between the treatment data and eligible coverage defined by the insurance carrier identified by the insurance carrier data;
    receiving via the user interface a signal which represents user acceptance of the offering to bill the additional expense item;
    processing the treatment data by a computing device to obtain nurse documentation, including at least one of: treatment sheet, flow sheet, drug inventory form, and reorder form; and
    automatically generating by the computing device the electronic bill having optimized reimbursable insurance claim items including the additional expense item in response to the signal, the claim items having predetermined codes based on the treatment data and the insurance carrier data to facilitate approval of the bill and to maximize reimbursement by the insurance carrier.

2. The method as claimed in claim 1, wherein the treatment data also identifies at least one of: a drug dosage, time spent in administering the drug, and supplies used in administering the drug.

3. The method as claimed in claim 1, wherein the treatment sheet includes at least one of: a route taken to administer the drug, names of drugs in same concurrent infusion, and time spent to administer the drug.

4. The method as claimed in claim 1, further comprising applying an appropriate modifier to at least one claim item on the bill.

5. The method as claimed in claim 1, further comprising adding at least one predetermined code required for reimbursement of the drug or procedure.

6. The method as claimed in claim 1, further comprising verifying that an HCT level is recorded and meets a minimum level required for reimbursement of the drug by the insurance carrier.

7. The method as claimed in claim 1, further comprising generating remarks containing at least one of: a predetermined code, a drug name, a drug dosage, a drug waste, and a route taken in administering the drug.

8. The method as claimed in claim 1, further comprising generating remarks to document when the patient provides the administered drug to ensure reimbursement for administration of the patient-provided drug.

9. The method as claimed in claim 1, further comprising issuing an appropriate code for the administration of the at least one drug.

10. The method as claimed in claim 1, further comprising applying a predetermined code to distinguish between types of administrations and any concurrent infusions.

11. The method as claimed in claim 1, further comprising determining a correct set of codes and respective quantity fields to bill a correct representation of infusion times and drug quantities, including waste and administration counts.

12. The method as claimed in claim 1, further comprising disallowing multiple drug administrations unless a predetermined code is included on the bill.

13. The method as claimed in claim 12, further comprising generating a claim item with an associated predetermined code wherein a total dosage of the drug is substantially equal to a sum of the dosages of multiple drugs.

14. The method as claimed in claim 1, further comprising ordering and sequencing the claim items of claims in a manner to facilitate approval of the bill by the insurance carrier.

15. The method as claimed in claim 14, wherein related administered drugs and their respective predetermined codes are grouped together in a single claim.

16. The method as claimed in claim 1, further comprising issuing prompts for supplies by the insurance carrier, issuing prompts for office visits, and tracking of chemo follow-up visits.

17. The method as claimed in claim 1, further comprising precisely estimating drug waste.

18. The method as claimed in claim 1, further comprising collecting and generating documentation in the treatment sheet to corroborate a claim.

19. The method as claimed in claim 1, further comprising monitoring and issuing alerts pertaining to elapsed infusion times, supplies, drug package and vial sizes, and other services.

20. The method as claimed in claim 1, further comprising generating various reports with application of different fee schedules and usage of drugs by package and vial sizes.

21. The method as claimed in claim 1, further comprising generating various fee schedules to accommodate data entry into a billing software system and to facilitate financial analysis of patient encounters.

22. The method as claimed in claim 1, further comprising tracking of drug usage in order to maintain inventory and to activate ordering of drugs for practice.

23. A system for generating an electronic bill having optimized insurance claim items based on an insurance carrier of a patient, the system comprising:
 a processor configured to execute computer program instructions;
 a memory configured to store the computer program instructions executable by the processor; and
 the computer program instructions stored in the memory to perform the steps of:
  receiving via a user interface insurance carrier data which identifies a patient's insurance carrier and patient data which identifies a patient;
  receiving via the user interface treatment data which identifies at least one drug including a chemotherapy drug administered to the patient and at least one type of administration used to administer the at least one drug to the patient on a date of service;
  displaying via the user interface a prompt offering to bill an additional expense item eligible for reimbursement based on a comparison between the treatment data and eligible coverage defined by the insurance carrier identified by the insurance carrier data;
  receiving via the user interface a signal which represents user acceptance of the offering to bill the additional expense item;
  processing the treatment data to obtain nurse documentation, including at least one of: treatment sheet, flow sheet, drug inventory form, and reorder form; and
  automatically generating the electronic bill having optimized reimbursable insurance claim items including the additional expense item in response to the signal, the claim items having predetermined codes based on the treatment data and the insurance carrier data to facilitate approval of the bill and to maximize reimbursement by the insurance carrier.

24. The system as claimed in claim 23, wherein the treatment data also identifies at least one of: a drug dosage, time spent in administering the drug, and supplies used in administering the drug.

25. The system as claimed in claim 23, wherein the treatment sheet includes at least one of: a route taken to administer the drug, names of the drugs in the same concurrent infusion, and time spent to administer the drug.

26. The system as claimed in claim 23, wherein the instructions perform the step of applying an appropriate modifier to at least one claim item on the bill.

27. The system as claimed in claim 23, wherein the instructions perform the step of adding at least one predetermined code required for reimbursement of the drug or procedure.

28. The system as claimed in claim 23, wherein the instructions perform the step of verifying that an HCT level is recorded and meets a minimum level required for reimbursement of the drug by the insurance carrier.

29. The system as claimed in claim 23, wherein the instructions perform the step of generating remarks containing at least one of: a predetermined code, a drug name, a drug dosage, a drug waste, and a route taken in administering the drug.

30. The system as claimed in claim 23, wherein the instructions perform the step of generating remarks to document when the patient provides the administered drug to ensure reimbursement for administration of the patient-provided drug.

31. The system as claimed in claim 23, wherein the instructions perform the step of issuing an appropriate code for the administration of the at least one drug.

32. The system as claimed in claim 23, wherein the instructions perform the step of applying a predetermined code to distinguish between types of administrations and any concurrent infusions.

33. The system as claimed in claim 23, wherein the instructions perform the step of determining a correct set of codes and respective quantity fields to bill a correct representation of infusion times and drug quantities, including waste and administration counts.

34. The system as claimed in claim 23, wherein the instructions perform the step of disallowing multiple drug administrations unless a predetermined code is included on the bill.

35. The system as claimed in claim 34, wherein the instructions perform the step of generating a claim item with an associated predetermined code wherein a total dosage of the drug is substantially equal to a sum of dosages of multiple drugs.

36. The system as claimed in claim 23, wherein the instructions perform the step of ordering and sequencing the claim items of claims in a manner to facilitate approval of the bill by the insurance carrier.

37. The system as claimed in claim 36, wherein related administered drugs and their respective predetermined codes are grouped together by the instructions in a single claim.

38. The system as claimed in claim 23, wherein the instructions perform the steps of issuing prompts for supplies by the insurance carrier, issuing prompts for office visits, and tracking of chemo follow-up visits.

39. The system as claimed in claim 23, wherein the instructions perform the step of precisely estimating drug waste.

40. The system as claimed in claim 23, wherein the instructions perform the step of collecting and generating documentation in the treatment sheet to corroborate a claim.

41. The system as claimed in claim 23, wherein the instructions perform the steps of monitoring and issuing alerts pertaining to elapsed infusion times, supplies, drug package sizes, vial sizes, and other services.

42. The system as claimed in claim 23, wherein the instructions perform the step of generating various reports with application of different fee schedules and usage of drugs by package and vial sizes.

43. A computer readable non-transitory medium that when executed by a processor causes a computer to perform the steps of:
 receiving via a user interface insurance carrier data which identifies a patient's insurance carrier and patient data which identifies a patient;
 receiving via the user interface treatment data which identifies at least one drug including a chemotherapy drug administered to the patient and at least one type of administration used to administer the at least one drug to the patient on a date of service;
 displaying via the user interface a prompt offering to bill an additional expense item eligible for reimbursement based on a comparison between the treatment data and eligible coverage defined by the insurance carrier identified by the insurance carrier data;
 receiving via the user interface a signal which represents user acceptance of the offering to bill the additional expense item;

processing the treatment data to obtain nurse documentation, including at least one of: treatment sheet, flow sheet, drug inventory form, and reorder form; and automatically generating the electronic bill having optimized reimbursable insurance claim items including the additional expense item in response to the signal, the claim items having predetermined codes based on the treatment data and the insurance carrier data to facilitate approval of the bill and to maximize reimbursement by the insurance carrier.

44. The computer readable non-transitory medium as claimed in claim 43, wherein the step of automatically generating is performed at least in part via a computing device.

* * * * *